US010213380B2

(12) United States Patent
Morehouse

(10) Patent No.: US 10,213,380 B2
(45) Date of Patent: Feb. 26, 2019

(54) METHOD OF TREATING EAR PAIN

(71) Applicant: Try This First, Inc., Walnut Creek, CA (US)

(72) Inventor: Scott Morehouse, Berkeley, CA (US)

(73) Assignee: Try This First, Inc., Walnut Creek, CA (US)

( * ) Notice: Subject to any disclaimer, the term of this patent is extended or adjusted under 35 U.S.C. 154(b) by 351 days.

(21) Appl. No.: 15/162,116

(22) Filed: May 23, 2016

(65) Prior Publication Data

US 2016/0331680 A1 Nov. 17, 2016

Related U.S. Application Data

(62) Division of application No. 13/818,068, filed as application No. PCT/US2011/050211 on Sep. 1, 2011, now Pat. No. 10,080,718.

(60) Provisional application No. 61/379,240, filed on Sep. 1, 2010.

(51) Int. Cl.
| | |
|---|---|
| *A61K 31/07* | (2006.01) |
| *A61K 9/00* | (2006.01) |
| *A61K 31/045* | (2006.01) |
| *A61K 36/00* | (2006.01) |
| *A23G 3/56* | (2006.01) |
| *A61K 31/194* | (2006.01) |
| *A61K 36/808* | (2006.01) |
| *A61B 17/24* | (2006.01) |
| *A61K 31/047* | (2006.01) |
| *A61K 31/167* | (2006.01) |
| *A61K 31/192* | (2006.01) |
| *A61K 31/375* | (2006.01) |
| *A61K 31/616* | (2006.01) |
| *A61K 31/7032* | (2006.01) |
| *A61K 36/752* | (2006.01) |
| *A61K 45/06* | (2006.01) |
| *A61K 31/19* | (2006.01) |
| *A61K 31/197* | (2006.01) |
| *A61K 31/355* | (2006.01) |
| *A61K 31/4188* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/675* | (2006.01) |
| *A61K 33/00* | (2006.01) |
| *A61K 33/06* | (2006.01) |
| *A61K 36/28* | (2006.01) |
| *A61K 36/48* | (2006.01) |
| *A61K 36/534* | (2006.01) |
| *A61K 36/63* | (2006.01) |
| *A61K 36/71* | (2006.01) |

(52) U.S. Cl.
CPC ............ *A61K 9/0056* (2013.01); *A23G 3/563* (2013.01); *A61B 17/24* (2013.01); *A61K 31/045* (2013.01); *A61K 31/047* (2013.01); *A61K 31/07* (2013.01); *A61K 31/167* (2013.01); *A61K 31/19* (2013.01); *A61K 31/192* (2013.01); *A61K 31/194* (2013.01); *A61K 31/197* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/616* (2013.01); *A61K 31/675* (2013.01); *A61K 31/7032* (2013.01); *A61K 33/00* (2013.01); *A61K 33/06* (2013.01); *A61K 36/00* (2013.01); *A61K 36/28* (2013.01); *A61K 36/48* (2013.01); *A61K 36/534* (2013.01); *A61K 36/63* (2013.01); *A61K 36/71* (2013.01); *A61K 36/752* (2013.01); *A61K 36/808* (2013.01); *A61K 45/06* (2013.01)

(58) Field of Classification Search
None
See application file for complete search history.

(56) References Cited

U.S. PATENT DOCUMENTS

| | | |
|---|---|---|
| 5,176,151 A | 1/1993 | Harding |
| 5,922,346 A | 7/1999 | Hersh |
| 7,524,512 B2 | 4/2009 | Di Bartolomeo |
| 2004/0253307 A1 | 12/2004 | Hague et al. |
| 2005/0158252 A1 | 7/2005 | Romanowski et al. |
| 2006/0148726 A1 | 7/2006 | Berg |
| 2006/0205682 A1 | 9/2006 | Roberts et al. |
| 2007/0071824 A1 | 3/2007 | Rosenthal et al. |
| 2007/0178123 A1* | 8/2007 | Levenson ............ A61K 9/0053 424/400 |
| 2007/0274927 A1 | 11/2007 | Haley et al. |
| 2009/0232745 A1 | 9/2009 | Anderson |

FOREIGN PATENT DOCUMENTS

WO 2012031123 A2 3/2012

OTHER PUBLICATIONS

Beutel et al. (2007) "Oral Transmucosal Delivery of Fentanyl Citrate for Breakthrough Cancer Pain Relief" BEE 453 pp. 1-23.
(Continued)

*Primary Examiner* — Terry A McKelvey
*Assistant Examiner* — Catheryne Chen
(74) *Attorney, Agent, or Firm* — Patterson & Sheridan, LLP

(57) ABSTRACT

The present invention relates generally to a methods of treating ear infections and clearing excess fluid from Eustachian tubes.

20 Claims, 4 Drawing Sheets

(56) References Cited

OTHER PUBLICATIONS

Coconut Grove Pharmacy (2011) "Pediatric Formulation Suggestions—Cough 1 Cold" pp. 1-2 [retrieved on Jul. 1, 2011]. Retrieved from the Internet: http://www.coconutgrovepharmacy.com/home/pediatric-formulation.php.

Ear Candling (2005, http://www.audiologyonline.com/articles/ear-candling-fool-proof-method-1010).

Engelke et al. (2011) "Intra-oral compartment pressures: a biofunctional model and experimental measurements under different conditions of posture," Clin Oral Invest, 15:165-176.

Geddes et al. (2008) "Tongue movement and intra-oral vacuum in breastfeeding infants," Early Human Development, 84:471-477.

Hu et al. (2011) "Development and evaluation of a safe and effective sugar-free herbal lollipop that kills cavity-causing bacteria" Int J Oral Sci 3: 13-20.

Huang, et al. (2015) "Shape dynamics and scaling laws for a body dissolving in fluid flow," J. Fluid Mech., 765(R3): 1-10.

International Preliminary Report on Patentability and Written Opinion dated Mar. 14, 2013 issued in related Application No. PCT/US2011/050211 (WO/2012/031123), 7 pages.

International Search Report and Written Opinion dated Apr. 27, 2012 issued in related Application No. PCT/US2011/050211 (WO/2012/031123), 12 pages.

Knosel et al. (2010) "A controlled evaluation of oral screen effects on intra-oral pressure curve characteristics" European Journal of Orthodontics, 32:535-541.

Leaven 2000, http://www.llli.org/llleaderweb/lv/lvaugsep00p63.html.

Lin, et al. (2012) "Mucin Production andMucous CellMetaplasia in OtitisMedia," International Journal of Otolaryngology, 12 pages.

Maciel, Tamela (2015) "Physicists Ask: How Many Licks Does It Take to Get to the Center of a Lollipop?" Physics Central, Physics Buzz Blog, 4 pages.

Mamapedia (2008) "Earache Pain" pp. 1-4 [retrieved on Jul. 11, 2011]. Retrieved from the Internet: http://www.mamapedia.com/article/earache-pain.

Parent Hacks (2008) "Entice your sickie with a medicine-dipped lollipops" pp. 1-3 [retrieved on Jul. 10, 2011]. Retrieved from the Internet: http://www.parenthacks.com/2008/10/entice-your-sic.html.

\* cited by examiner

HUMAN ORAL CAVITY SHAPE

SIDE VIEW

FLAT SURFACE

BOTTOM VIEW

TOP VIEW

FLAT SHAPES

DISC

ELLIPTICAL

OBLONG

THREE-DIMENSIONAL SHAPES

CUBE

BRICK

CYLINDRICAL

THREE-DIMENSIONAL SHAPES

SPHERE

FOOTBALL-SHAPED

POLYHEDRON

METHOD OF TREATING EAR PAIN

CROSS-REFERENCE TO RELATED APPLICATIONS

This application is a divisional application of U.S. patent application Ser. No. 13/818,068, filed on May 10, 2013, which is a National Stage Entry of PCT/US2011/050211, filed on Sep. 1, 2011, which claims the benefit of U.S. Provisional Application No. 61/379,240, filed on Sep. 1, 2010. The related applications are hereby incorporated by reference in their entireties.

BACKGROUND OF THE INVENTION

The present invention relates generally to methods of treating ear infections and clearing excess fluid from Eustachian tubes.

There are four primary types of ear infections: acute otitis media (AOM); otitis media with effusion (OME); chronic otitis media (COM); and acute otitis externa (AOE).

AOM is a middle ear infection caused by bacteria that traveled to middle ear from fluid build-up in the Eustachian tube. AOM may develop during or after a cold or the flu. Middle ear infections are very common in children, but occur infrequently in adults. In children, ear infections often recur, particularly if they first develop in early infancy.

OME occurs when fluid (also referred to as an "effusion") becomes trapped behind the eardrum in one or both ears, even when there is no infection. In chronic and severe cases, the fluid may become sticky and may cause a condition commonly known as "glue ear." While OME or even glue ear is typically not painful, it frequently causes an uncomfortable feeling of stuffiness in the ears that is akin to a feeling of being under water. Children who are susceptible to OME can experience frequent episodes for up to half of their first three years of life. While most episodes of OME resolve within three months, 30-40% of children experience recurrent episodes. Chronic and severe OME may impair a child's hearing.

COM refers to persistent fluid behind the tympanic membrane without the presence of an infection. It is called suppurative chronic otitis when there is persistent inflammation in the middle ear or mastoids or if there is a chronic rupture of the eardrum with drainage.

AOE is an inflammation or infection of the outer ear and ear canal that is triggered by water that gets trapped in the ear. The trapped water can cause bacteria and fungi to breed. AOE can also be precipitated by overly aggressively scratching or cleaning of the ears or when an object gets stuck in the ears.

The standard of care for the treatment of ear infections is either to wait until the infection clears or to treat the infection with antibiotics. Typically, pain associated with the ear infection is treated with ibuprofen or acetaminophen. For patients that experience chronic ear infections, the repeated use of antibiotics poses risks that the bacterium or bacteria that are causing the infection will become resistant to the antibiotics. Once a patient becomes resistant to a particular antibiotic, the patient must require higher doses of the antibiotic and/or switch to a different antibiotic to treat the infection.

SUMMARY

In one aspect, the present invention provides a method of treating ear infections, and its associated pain, that does not require the administration of antibiotics.

In one aspect, there is provided a method of treating an ear infection comprising administering an antibiotic-free salivary-producing composition to an individual suffering from an ear infection.

In another aspect, there is provided a method of treating pain associated with an ear infection comprising administering to an individual suffering with pain from an ear infection an antibiotic-free salivary-producing composition comprising an internal analgesic.

In one embodiment, the salivary-producing composition is a solid. In one embodiment, the salivary-producing composition is a solid confection. In one embodiment, the salivary-producing composition is dissolvable. In one embodiment, the salivary-producing composition is a lollipop. In various embodiments, the salivary-producing composition (e.g., lollipop) may have any suitable shape, including without limitation, a shape selected from the group consisting of disc shaped, spherically shaped, elliptically shaped, oblong, cylindrical, cuboidal, and rectangular. In some embodiments, the salivary-producing composition (e.g., lollipop) may have a shape in the form of a human oral cavity, a polyhedron (e.g., an octahedron) or a pacifier (e.g., the shape of a NUK® pacifier). In some embodiments, the lollipop has a handle that is a stick or a loop.

In some embodiments, the internal analgesic is selected from sugar and/or a non-steroidal anti-inflammatory agent. In another embodiment, the internal analgesic is selected from ibuprofen and acetaminophen. In some embodiments, the non-steroidal anti-inflammatory agent is selected from the group consisting of acetaminophen, aspirin, choline and magnesium salicylates, choline salicylate, celecoxib, diclofenac, diclofenac potassium, diclofenac sodium, diclofenac sodium with misoprostol, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, and mixtures thereof.

In a further embodiment, the salivary-producing composition further comprises a sweetening agent selected from the group consisting of honey, maple syrup, evaporated cane juice, concentrated fruit juice, dextrose, fructose, sucrose, mannitol, sorbitol, xylitol, and mixtures thereof. In some embodiments, the salivary-producing composition further comprises a sweetening agent selected from the group consisting of honey, maple syrup, evaporated cane juice, concentrated fruit juice, dextrose, fructose, sucrose, mannitol, sorbitol, aspartame, cyclamate, saccharin, *stevia*, sucralose, xylitol, glucose, isomalt, arabitol, erythritol, glycerol, hydrogenated Starch Hydrosylate (HSH), lactitol, maltitol, and mixtures thereof. In some embodiments, the salivary-producing composition further comprises a sugar alcohol, e.g., selected from the group consisting of xylitol, mannitol, sorbitol, isomalt, arabitol, erythritol, glycerol, hydrogenated Starch Hydrosylate (HSH), lactitol, maltitol, and mixtures thereof.

In another embodiment, the salivary-producing composition further comprises a natural flavoring obtained from a source selected from the group consisting of acai berries, aloe vera, apples, bananas, blueberries, cantaloupe, caramel, carrots, cherries, chocolate, coconut, coffee, cranberries, grapefruits, grapes, guava, honeydew melons, kiwi, lemons, licorice, limes, lychee fruits, mango, nectarines, olallieberries, oranges, peaches, pears, pineapples, pomegranates, raspberries, strawberries, tangerines, vanilla, watermelon, wheat grass, and mixtures thereof. In another embodiment, the salivary-producing composition further comprises a natural flavoring obtained from a source selected from the group consisting of peppermint oil, spearmint oil, and mixtures thereof.

In a further embodiment, the salivary-producing composition further comprises citric acid.

In another embodiment, the salivary-producing composition further comprises one or more homeopathic medicines, including without limitation, Acontum Napellus, Allium Ceia, Arnica, Mullein, Belladona, Bellis Perennis, Calendula, Calcarea Carbonica, Chamomilla, Ferum Phosphorilum, Hamamelis, Hepar Sulphuris, Hypericum Perforatum (Saint John's Wort), Kau Bichromicum, Kau lodatum, Kau Muriaticum, Kau Sulphuricum, Lycopodium, Mercurius Solubilis, Mezereum, Millefolium, Natrum Sulphuricum, Phytolacca Decandra, Phosphorus, Pulsatilla, Sulphur, and Symphytum Officinale. In some embodiments, the salivary-producing composition comprises Mullein.

In a further embodiment, the salivary-producing composition further comprises one or more vitamin or dietary supplements selected from the group consisting of vitamin A, vitamin B1, vitamin B2, vitamin B3, vitamin B5, vitamin B6, vitamin B7, vitamin B8, vitamin B9, vitamin B12, a B complex vitamin, vitamin C, vitamin D, vitamin E, calcium, magnesium, manganese, potassium, selenium, and sodium bicarbonate. In some embodiments, the salivary-producing composition comprises one or more vitamin or dietary supplements selected from the group consisting of vitamin A, vitamin B1, vitamin B2, vitamin B3, vitamin B5, vitamin B6, vitamin B7, vitamin B8, vitamin B9, vitamin B12, a B complex vitamin, vitamin C, vitamin E, magnesium and selenium.

In another embodiment, the salivary-producing composition further comprises one or more extracts selected from the group consisting of bee propolis extract, chinese vitex, *echinacea*, elder, forsythia, garlic, ginger, goldenseal root extract, horehound, hyssop, isatis, lemon balm, lemon oil, linden flowers, *lonicera*, mallow, menthol, mineral oil, peppermint, sage, schizonepeta, slippery elm bark extract, and wild thyme. In some embodiments, the salivary producing composition comprises one or more extracts selected from the group consisting of *echinacea*, goldenseal root extract, and peppermint oil.

In a further embodiment, the salivary-producing composition further comprises an essential or non-essential amino acid.

In some embodiments, the salivary producing composition comprises one or more active ingredients selected from the group consisting of vitamin A, vitamin B1, vitamin B2, vitamin B3, vitamin B5, vitamin B6, vitamin B7, vitamin B8, vitamin B9, vitamin B12, a B complex vitamin, vitamin C, vitamin E, zinc, magnesium, selenium, *echinacea*, olive leaf (*olea europaea*), wild indigo (*baptisia tinctoria*), goldenseal (*hydrastis canadensis*), fenugreek (*trigonella foenum-graecum*), mullein (*verbascum olympicum* and *thapsus*), phenol, camphor, pectin, *eucalyptus* oil, peppermint oil, spearmint oil, and mixtures thereof.

In a related aspect, the invention provides a composition, wherein the composition is in the shape of a human oral cavity. In some embodiments, the composition includes (e.g., comprises, consists of, or consists essentially of) one or more active ingredients selected from the group consisting of vitamin A, vitamin B1, vitamin B2, vitamin B3, vitamin B5, vitamin B6, vitamin B7, vitamin B8, vitamin B9, vitamin B12, a B complex vitamin, vitamin C, vitamin E, zinc, magnesium, selenium, *echinacea*, olive leaf, wild indigo, goldenseal, fenugreek, mullein (*verbascum olympicum* and *thapsus*), phenol, camphor, pectin, *eucalyptus* oil, peppermint oil and spearmint oil.

In a further embodiment, the composition further comprises a sweetening agent selected from the group consisting of honey, maple syrup, evaporated cane juice, concentrated fruit juice, dextrose, fructose, sucrose, mannitol, sorbitol, xylitol, and mixtures thereof. In some embodiments, the composition further comprises a sweetening agent selected from the group consisting of honey, maple syrup, evaporated cane juice, concentrated fruit juice, dextrose, fructose, sucrose, mannitol, sorbitol, aspartame, cyclamate, saccharin, *stevia*, sucralose, xylitol, glucose, isomalt, arabitol, erythritol, glycerol, hydrogenated Starch Hydrosylate (HSH), lactitol, maltitol, and mixtures thereof. In some embodiments, the composition further comprises a sugar alcohol selected from the group consisting of xylitol, mannitol, sorbitol, isomalt, arabitol, erythritol, glycerol, hydrogenated Starch Hydrosylate (HSH), lactitol, maltitol, and mixtures thereof.

In another embodiment, the composition further comprises a natural flavoring obtained from a source selected from the group consisting of acai berries, aloe vera, apples, bananas, blueberries, cantaloupe, caramel, carrots, cherries, chocolate, coconut, coffee, cranberries, grapefruits, grapes, guava, honeydew melons, kiwi, lemons, licorice, limes, lychee fruits, mango, nectarines, olallieberries, oranges, peaches, pears, pineapples, pomegranates, raspberries, strawberries, tangerines, vanilla, watermelon, wheat grass, and mixtures thereof. In another embodiment, the composition further comprises a natural flavoring obtained from a source selected from the group consisting of peppermint oil, spearmint oil, and mixtures thereof.

In a further embodiment, the composition further comprises citric acid.

In a further embodiment, the composition further comprises an antibiotic.

In another embodiment, the composition further comprises one or more homeopathic medicines, including without limitation, Acontum Napellus, Allium Ceia, Arnica, Mullein, Belladona, Bellis Perennis, Calendula, Calcarea Carbonica, Chamomilla, Ferum Phosphorilum, Hamamelis, Hepar Sulphuris, Hypericum Perforatum (Saint John's Wort), Kau Bichromicum, Kau lodatum, Kau Muriaticum, Kau Sulphuricum, Lycopodium, Mercurius Solubilis, Mezereum, Millefolium, Natrum Sulphuricum, Phytolacca Decandra, Phosphorus, Pulsatilla, Sulphur, and Symphytum Officinale. In some embodiments, the composition comprises Mullein.

In a further embodiment, the composition further comprises one or more vitamin or dietary supplements selected from the group consisting of vitamin A, vitamin B1, vitamin B2, vitamin B3, vitamin B5, vitamin B6, vitamin B7, vitamin B8, vitamin B9, vitamin B12, a B complex vitamin, vitamin C, vitamin D, vitamin E, calcium, magnesium, manganese, potassium, selenium, and sodium bicarbonate. In some embodiments, the composition comprises one or more vitamin or dietary supplements selected from the group consisting of vitamin A, vitamin B1, vitamin B2, vitamin B3, vitamin B5, vitamin B6, vitamin B7, vitamin B8, vitamin B9, vitamin B12, a B complex vitamin, vitamin C, vitamin E, magnesium and selenium.

In another embodiment, the composition further comprises one or more extracts selected from the group consisting of bee propolis extract, chinese vitex, *echinacea*, elder, forsythia, garlic, ginger, goldenseal root extract, horehound, hyssop, isatis, lemon balm, lemon oil, linden flowers, *lonicera*, mallow, menthol, mineral oil, peppermint, sage, schizonepeta, slippery elm bark extract, and wild thyme. In some embodiments, the composition comprises one or more extracts selected from the group consisting of *echinacea*, goldenseal root extract, and peppermint oil.

In a further embodiment, the composition further comprises an essential or non-essential amino acid.

In one embodiment, the composition is a solid. In one embodiment, the composition is a solid confection. In one embodiment, the composition is dissolvable. In one embodiment, the composition is a lollipop. In various embodiments, the salivary-producing composition (e.g., lollipop) may have any suitable shape, including without limitation, a shape selected from the group consisting of disc shaped, spherically shaped, elliptically shaped, oblong, cylindrical, cuboidal, and rectangular. In some embodiments, the composition (e.g., lollipop) may have a shape in the form of a human oral cavity, a polyhedron (e.g., an octahedron) or a pacifier (e.g., the shape of a NUK® pacifier). In some embodiments, the lollipop has a handle that is a stick or a loop.

In another aspect, the invention provides a method of treating an ear infection comprising administering to an individual in need thereof a composition, wherein the composition is in the shape of a human oral cavity. In some embodiments, the composition comprises one or more active ingredients selected from the group consisting of vitamin A, vitamin B1, vitamin B2, vitamin B3, vitamin B5, vitamin B6, vitamin B7, vitamin B8, vitamin B9, vitamin B12, a B complex vitamin, vitamin C, vitamin E, zinc, magnesium, selenium, *echinacea*, olive leaf, wild indigo, goldenseal, fenugreek, mullein (*verbascum olympicum* and *thapsus*), phenol, camphor, pectin, *eucalyptus* oil, peppermint oil and spearmint oil. In some embodiments, the administering comprises the individual sucking on the composition while the individual is lying down with the infected ear facing upward, thereby forming a negative pressure in the oral cavity. Further embodiments of the compositions are described above and herein.

In a further aspect, the invention provides a method of clearing fluid from the Eustachian tubes of an individual in need thereof, comprising administering to the individual a composition, wherein the composition is in the shape of a human oral cavity, wherein said administering comprises the individual sucking on the composition while the individual is lying down with the affected ear facing upward, thereby forming a negative pressure within the oral cavity that promotes clearing of fluid from the Eustachian tubes.

In a further aspect, the invention provides a method of alleviating pain associated with an ear infection, comprising administering to an individual suffering from pain associated with an ear infection a composition comprising an internal analgesic, wherein the composition is in the shape of a human oral cavity, wherein said administering comprises the individual sucking on the composition while the individual is lying down with the infected ear facing upward, thereby forming a negative pressure within the oral cavity that promotes pressure equalization in the middle ear, thereby alleviating pain associated with the ear infection.

In a further aspect, the invention provides a method of alleviating pain associated with a clogged or blocked inner ear canal, comprising administering to an individual suffering from pain associated with clogged or blocked inner ear canal a composition comprising an internal analgesic, wherein the composition is in the shape of a human oral cavity, wherein said administering comprises the individual sucking on the composition while the individual is lying down with the infected ear facing upward, thereby forming a negative pressure within the oral cavity that promotes pressure equalization in the middle ear, thereby alleviating pain associated with the clogged or blocked inner ear canal.

In various embodiments, positioning the individual such that the affected ear is facing upward allows for gravity to assist in the draining of the infected Eustachian tube (ET).

In some embodiments, the internal analgesic is selected from sugar and/or a non-steroidal anti-inflammatory agent. In some embodiments, the non-steroidal anti-inflammatory agent is selected from ibuprofen and acetaminophen. In some embodiments, the non-steroidal anti-inflammatory agent is selected from the group consisting of acetaminophen, aspirin, choline and magnesium salicylates, choline salicylate, celecoxib, diclofenac, diclofenac potassium, diclofenac sodium, diclofenac sodium with misoprostol, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, and mixtures thereof.

In some embodiments, the composition includes (e.g., comprises, consists of, or consists essentially of) one or more active ingredients selected from the group consisting of vitamin A, vitamin B1, vitamin B2, vitamin B3, vitamin B5, vitamin B6, vitamin B7, vitamin B8, vitamin B9, vitamin B12, a B complex vitamin, vitamin C, vitamin E, zinc, magnesium, selenium, *echinacea*, olive leaf, wild indigo, goldenseal, fenugreek, mullein (*verbascum olympicum* and *thapsus*), phenol, camphor, pectin, *eucalyptus* oil, peppermint oil, spearmint oil, and mixtures thereof. In some embodiments, the composition is a lollipop. In some embodiments, the composition comprises a sweetening agent selected from the group consisting of aspartame, cyclamate, saccharin, *stevia*, sucralose, xylitol, glucose, isomalt, arabitol, erythritol, glycerol, hydrogenated Starch Hydrosylate (HSH), lactitol, and maltitol. Further embodiments of the compositions are described above and herein.

In some embodiments, the individual has an ear infection selected from the group consisting of acute otitis media (AOM); otitis media with effusion (OME); chronic otitis media (COM); and acute otitis externa (AOE).

In some embodiments, the composition is dissolvable.

In some embodiments, sucking on the composition causes saliva to be produced and negative pressure to be formed in the intraoral space, wherein swallowing the saliva promotes opening of the Eustachian tubes (ET), which combines with the formation of the negative pressure within the oral cavity to facilitate clearing of fluid from the Eustachian tubes.

In some embodiments, a negative pressure within the oral cavity is created when an individual sucks on the composition with a shape in the form of a human oral cavity, and said negative pressure exceeds any negative pressure created in the oral cavity when an individual sucks on a composition with a shape in the form other than a human oral cavity, e.g., a spherical or disc-shaped composition.

In some embodiments, the rate of saliva production is increased by at least about 10% percent over baseline when an individual sucks on the composition.

In some embodiments, the individual is not at an elevated altitude or in an airplane. In some embodiments of the methods, the individual is at normal atmospheric pressure.

Additional aspects and embodiments will be provided, without limitation, in the detailed description of the invention that is set forth below.

Definitions

As used in this specification and the appended claims, the singular forms "a," "an," and "the" include plural referents unless the context clearly dictates otherwise. The terms "comprises" and/or "comprising," as used in this specification and the appended claims, specify the presence of stated features, steps, components and/or groups, but do not preclude the presence or addition of one or more other features, steps, components, and/or groups.

Within the context of the present invention, the term "individual," "subject" or "patient" refers to a human afflicted with an ear infection. The individual will often be a child under the age of 10 years of age; however, the individual may also be an early adolescent (10 to 13 years of age), an adolescent (14-18 years of age), or an adult (over 18 years of age).

The term "treatment" or "alleviating" as used herein refers to reduction in severity and/or frequency of symptoms associated with ear infections, including pain.

The terms "active agent" and "drug" are used interchangeably to refer to a chemical material or compound which, when administered to a patient induces a desired pharmacologic effect. Included are derivatives that include pharmacologically acceptable and pharmacologically active salts, esters and amides, as well as prodrugs and conjugates. Analogs of those compounds or classes of compounds specifically mentioned that also induce the desired pharmacologic effect, are also included.

The term "effective amount" or "pharmaceutically effective amount" refer to the amount and/or dosage, and/or dosage regime of one or more compounds necessary to bring about the desired result e.g., an amount sufficient to mitigating in a subject the pain and/or discomfort associated with excess fluid in the inner ear canal, or clogged or blocked Eustachian tubes (ET).

The term "lollipop" refers to a piece of hard candy attached to a stick or "handle."

The term "shape of a human oral cavity" refers to a solid composition or solid confection that is substantially flat on a first side (e.g., for contacting the tongue) and rounded on the remainder of the composition, e.g., as in a half-spherical or half-oval shape (e.g., for contacting the roof of the mouth). A composition of the form or shape of a human oral cavity is of a size to comfortably fit within a human oral cavity of a subject.

The term "substantially flat" in the context of a surface of a solid composition or solid confection refers to a substantially smooth, level surface with little or no slope, tilt, or curvature. In some embodiments, a substantially flat surface may be slightly concave or convex. In some embodiments, the substantially flat surface is textured, e.g., with ridges or bumps.

The term "pacifier shape" refers to any conventional or commercially available shape of a mouthpiece of a pacifier. In various embodiments, pacifier shape refers to standard nipple shape or the orthodontic pacifier shape. In some embodiments, pacifier shape refers to the shape of a NUK® pacifier.

The term "polyhedron" refers to a three-dimensional a solid bounded by usually 4 or more plane faces (i.e., flat faces) and straight edges. In various embodiments, the polyhedron is a regular polyhedron.

The term "octahedron" refers to a three-dimensional shape having eight plane faces, for example, a regular solid figure with eight equal triangular faces.

The term "octagon" or "octagonal" refers to a disk shape having two substantially flat surfaces, eight straight sides and eight side angles.

The term "consisting essentially of" refers to the genera or species of active pharmaceutical agents recited in a method or composition, and further can include other agents that, on their own do not effect substantial activity for the recited indication or purpose. In some embodiments, the phrase "consisting essentially of" expressly excludes the inclusion of one or more additional active agents not specifically recited.

DETAILED DESCRIPTION OF CERTAIN INVENTIVE EMBODIMENTS

Introduction

Figure 1A:
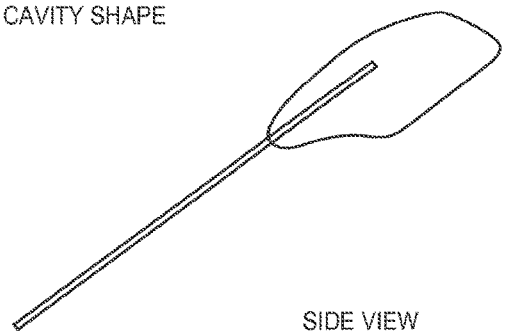
FIGS. 1A-C illustrate side (A), bottom (B) and top (C) views of a composition in the shape of a human oral cavity.
Figure 1B:
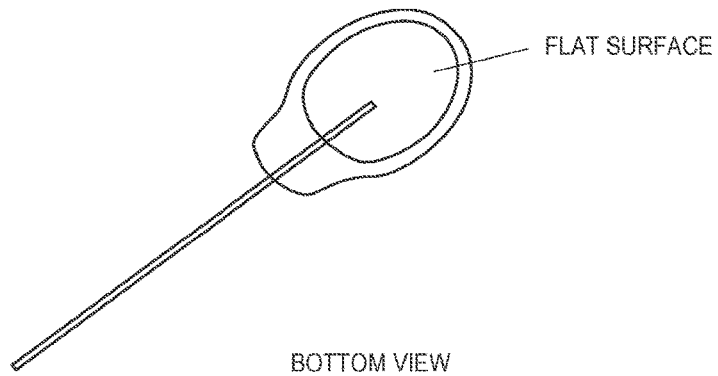
Figure 1C:
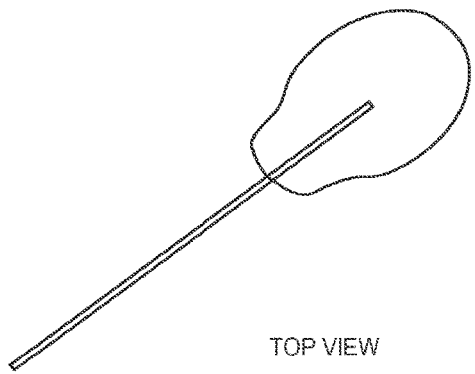
Figure 2A:
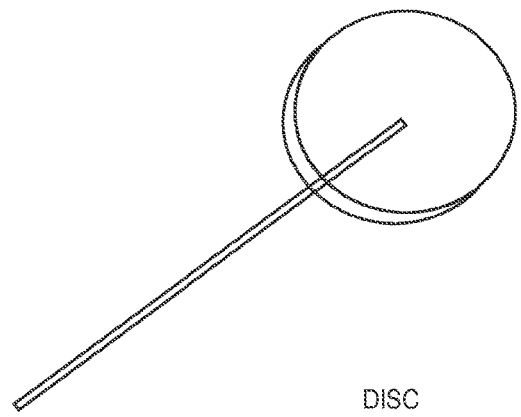
FIGS. 2A-C illustrate flat compositions shapes, including disc or round (A), elliptical or oval (B) and oblong (C).
Figure 2B:
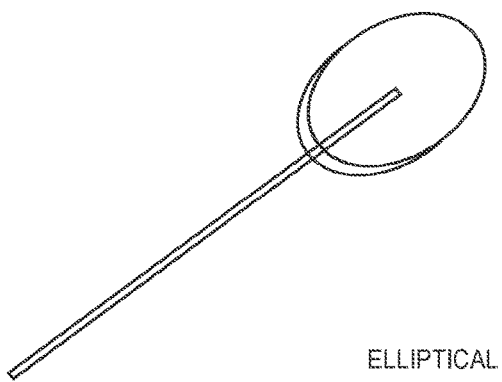
Figure 2C:
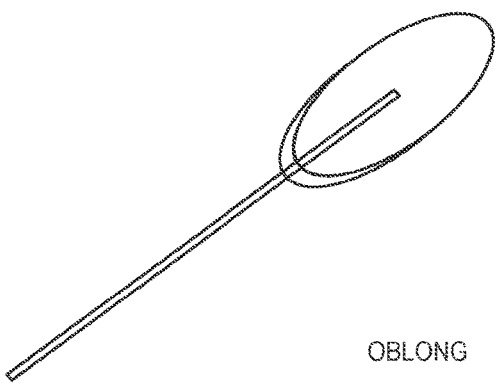
Figure 3A:
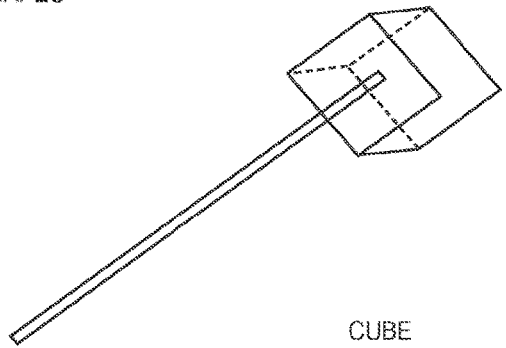
FIGS. 3A-C illustrate 3-dimensional shapes, including cube (A), brick (B) and cylindrical (C).
Figure 3B:
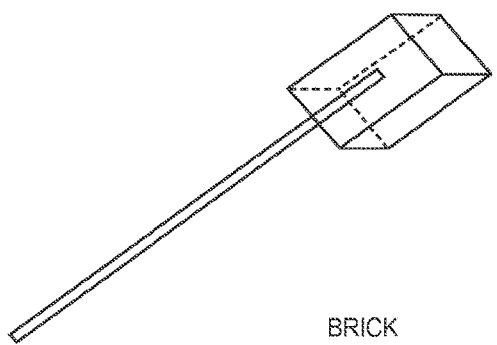
Figure 3C:
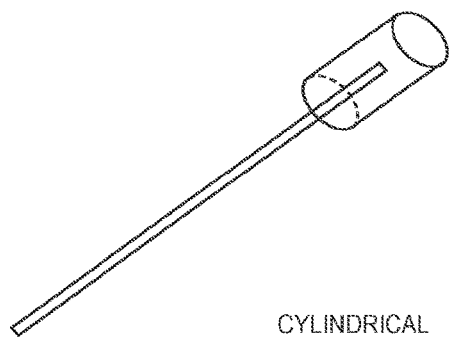
Figure 4A:
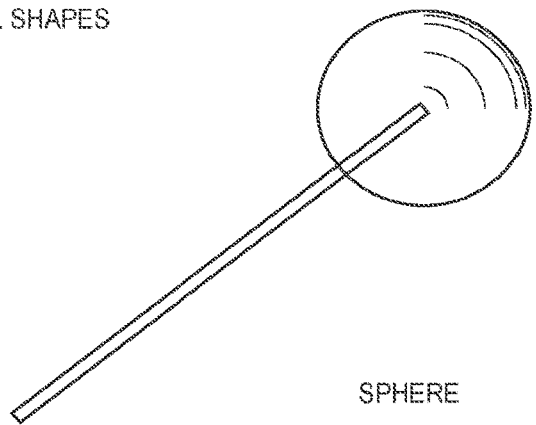
FIGS. 4A-C illustrate 3-dimensional shapes, including spherical (A), football-shaped (B) and polyhedron (C).
Figure 4B:
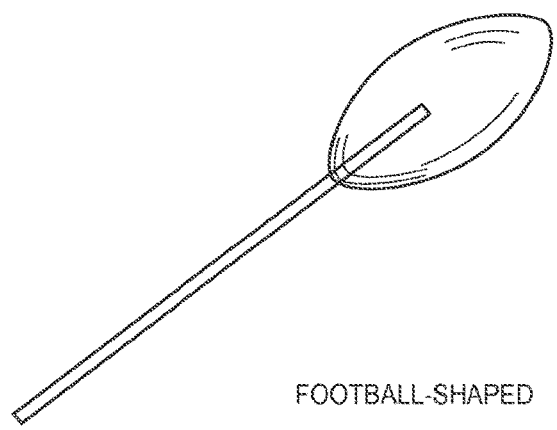
Figure 4C:
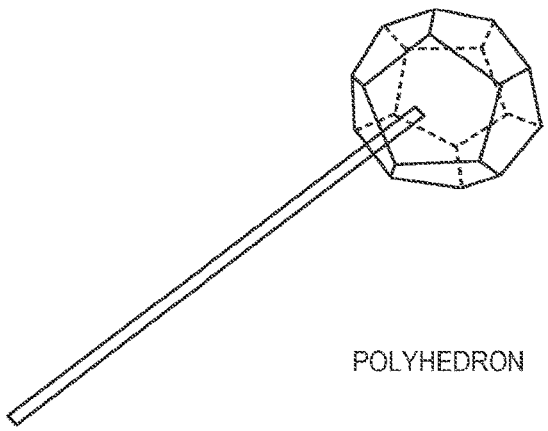

The present invention is directed to a method of treating ear infections, and its associated pain, that does not require the administration of antibiotics.

In one aspect of the invention, the present invention is directed to a method of treating an ear infection comprising administering an antibiotic-free salivary-producing composition to an individual suffering from an ear infection.

Without being bound by theory, it is believed that the method of the present invention is able to treat ear infections through the sucking and pulling action that accompanies the administration of the salivary-producing composition of the present invention.

Subjects Who May Benefit from the Present Methods

Generally, the subject is suffering ear pain or experiencing pressure within the inner ear. For example, the subject may have excess fluid in the inner ear canal or fluid that is clogging the Eustachian tubes or the inner ear canal. The subject may or may not have an ear infection. In various embodiments, the subject has, or has been diagnosed as having, acute otitis media (AOM); otitis media with effusion (OME); chronic otitis media (COM); or acute otitis externa (AOE). Usually, the subject, patient or individual is a human.

The present invention finds utility primarily in the treatment of AOM ear infections and the pain associated with AOM ear infections in human children. In order to ensure the effectiveness of the composition described herein to small children, the composition is intended to be as palatable as possible to small children in a mode of administration that is easily administrable to small children. It is to be understood; however, that the method of the present invention is not limited to the treatment of AOM in human children and that the method of the present invention may also find utility in the treatment of ear infections in adolescents and adults suffering from AOM. The method of the present invention is also intended to have utility in the treatment of ear infections other than AOM, such as for example, OME, COM, and AOE, in children, adolescents, and adults.

The methods are particularly effective in small children because the Eustachian tubes of small children are more horizontally positioned than those of adults. As a human individual ages, the position of the Eustachian tubes shifts from a horizontal position to a more vertical position. In this way, the effect of the sucking and pulling on the Eustachian tube (e.g., by sucking and swallowing) is more pronounced in small children than in adolescents and adults. Notwithstanding the foregoing, the inventor has found that the method of the present invention is capable of treating ear infections and its associated pain in adults.

Methods of Treating Ear Infections

In practicing the present methods, the individual sucks on the compositions described herein lying down with the affected ear facing up. Sucking on the compositions compels the production of saliva and the action of swallowing. It is believed that the present methods help clear the Eustachian tubes (ET) by the swallowing associated with sucking on the salivary producing composition because the swallowing motion contracts the muscles around the ET and causes opening of the ET. The negative pressure created by sucking coupled with the contraction of the muscles to cause opening of the tube by swallowing, assisted by gravity where the infected ear or ear with a clogged or blocked ET is facing up all combine to drain the tubes. In addition, in certain embodiments, i.e., where the composition includes one or more anti-inflammatory ingredients, the anti-inflammatory characteristics of the composition can help reduce the swelling around the opening of the ET thereby making it easier for the ET to open during swallowing.

The compositions can but need not be dissolvable. In one embodiment of the invention, the composition is in the form of a troche or lozenge on a stick, such as for example, a lollipop. The lollipops can have a handle that is a stick or a loop.

The composition (e.g., lollipop) may be in any suitable shape and is generally of a size to fit comfortably within the oral cavity of the subject. In various embodiments, the composition (e.g., lollipop) is disc shaped, spherically shaped, elliptically shaped, oblong, polyhedral (e.g., octahedral) or octagonal. In various embodiments, the composition (e.g., lollipop) is in the shape of the oral cavity, e.g., flat on the surface that contacts the tongue, convex on the surface that contacts the roof of the mouth, and of a size that fits comfortably within the oral cavity of the subject. In various embodiments, the composition (e.g., lollipop) is in the shape of a mouth piece of a pacifier, e.g., in the shape of a nipple or a NUK®.

The shape of the composition can influence the strength of the negative pressure achieved within the oral cavity. In addition, sucking on a composition in the form or shape of a human oral cavity can increase the amount of saliva production in the oral cavity, thereby facilitating the effectiveness of clearing blocked fluid from the inner ear canal or ET. Determination of the amount of saliva production can be measured using any method known in the art. In one embodiment, saliva production can be measured with the Saxon test, a simple gauze-chewing procedure. See, e.g., Kohler and Winter, *Arthritis Rheum*. (1985) 28(10):1128-32; and Stevens, et al., *Am J Dis Child*. (1990) 144(5):570-1. In some embodiments, sucking on a composition described herein can increase the amount of saliva production in the oral cavity by at least about 5%, 10%, 15%, 20% or 25%, e.g., in comparison to a baseline, e.g., the amount of saliva produced when the subject is not sucking on anything. Including ingredients such as sugar, peppermint oil and/or citric acid can facilitate production of saliva. Determination of negative pressure within the oral cavity can also be measured using any method known in the art. In one embodiment, negative pressure within the oral cavity is measured by atmospheric pressure monitoring simultaneously carried out with a digital manometer in the vestibular inter-occlusal space (IOS) and at the palatal vault (sub-palatal space, SPS). See, e.g., Engelke, et al., *Clin Oral Investig*. (2011) 15(2):165-76. Intra-oral pressure can also be measured using oral end fittings connected to a piezo-resistive relative pressure sensor. See, e.g., Knösel, et al., *Eur J Orthod*. (2010) 32(5):535-41. In some embodiments, sucking on a composition described herein can increase the amount of negative pressure in the oral cavity by at least about 5%, 10%, 15%, 20% or 25%, e.g., in comparison to a baseline, e.g., the amount of negative pressure formed in the oral cavity when the subject is sucking on a composition that is not in the shape of a human oral cavity.

With respect to the posture and position of the subject for practicing the methods, in various embodiments, the subject is lying down with the affected ear facing up. The subject may be lying horizontally or substantially horizontally sufficient to allow gravity to facilitate clearing of the inner ear canal, or clogged or blocked ET, with formation of negative pressure in the oral cavity. For example, in some embodiments, the subject may be lying down but have their upper body slightly elevated, e.g., lying on a pillow or a lap. In some embodiments, it can be sufficient for the subject to tilt their head sufficiently horizontally to allow gravity to facilitate clearing of the inner ear canal, or clogged or blocked ET, with formation of negative pressure in the oral cavity. In this case, the subject may be standing or seated. In various embodiments, the affected ear is held 180° in relation to the ground, where the position of the ear on a head held upright is defined as 0 degrees in relation to the ground. In some embodiments, the affected ear is held about 135-180° in relation to the ground. As long as the position of the head and the affected ear is held sufficiently horizontally, facing up, to allow gravity to facilitate clearing of the inner ear canal, or clogged or blocked ET, with formation of negative pressure in the oral cavity, the rest of the subject's body can be in any position, including standing, seated or lying down.

In various embodiments, the compositions are dissolvable. The subject can suck on one or more of the compositions, described herein, for a time sufficient for clearing of the inner ear canal, or clogged or blocked ET, with formation of negative pressure in the oral cavity. In some embodiments, sucking on and consuming one composition will be sufficient to clear fluid from the ET or inner ear canal. In other instances, successful clearing of fluid from the ET or inner ear canal will require sucking on and consuming two or more compositions. Should the ET or inner ear canal again become clogged or blocked with excess fluid, the subject can suck on and consume further compositions, as needed, to again clear fluid from the ET or inner ear canal.

In another aspect of the invention, the present invention is directed to a method of treating pain associated with an ear infection comprising administering to an individual suffering with pain from an ear infection an antibiotic-free salivary-producing composition comprising an internal analgesic. Generally, the subject's posture and duration of performing this embodiment of the method are as described above. The internal analgesic may be any pain reliever or non-steroidal anti-inflammatory drug (NSAID). Pain relievers include without limitation, paracetamol, also known as acetaminophen. NSAIDs include without limitation, acetaminophen, aspirin, choline and magnesium salicylates, choline salicylate, celecoxib, diclofenac, diclofenac potassium, diclofenac sodium, diclofenac sodium with misoprostol, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, and mixtures thereof.

NSAIDs generally are known agents, and their appropriate dosages are known in the art. Appropriate dosage can depend on various factors, including without limitation, the level of pain, age, weight and general health condition of the subject. In various embodiments, the present methods and compositions deliver a dose of active agent that is equivalent or less than the recommended daily dose provided in standard texts, e.g., Brunton, et al., *Goodman and Gilman's The Pharmacological Basis of Therapeutics*, Twelfth Edition, 2010, McGraw-Hill Professional; or Physicians' Desk Reference 2011, 65th Edition, PDR Network. Dosages may also be determined by routine experimentation. For example, in determining an appropriate dosage, a lower dose can first be administered and then incrementally increased until an efficacious effect is observed with minimal or no undesirable side effects. Such known or determined dosages of NSAIDs may be used as a guideline for determining the amount of NSAID, or a pharmaceutically acceptable salt thereof, to include in the lollipop, typically taking into account various patient characteristics (e.g., level of pain, age, weight, and overall health) in a manner known to those skilled in the medical arts, as well as the characteristics of the lollipop (e.g., rate of dissolution) and the transmucosal delivery characteristics of the NSAID, or a pharmaceutically acceptable salt thereof.

Where the internal analgesic is acetaminophen, the dosage may be up to 150 mg for children and up to 300 mg for adults. Where the internal analgesic is ibuprofen, the dosage may be up to 100 mg for children and up to 200 mg for adults.

Compositions

Methods of preparing lollipops are known in the art. Typically lollipops are prepared by mixing one or more sweeteners with water in a non-stick or enameled saucepan, preferably with a spout, and heating the mixture with stirring until boiling. Examples of sweeteners that may be used to prepare lollipops are set forth in Table 1 and the accompanying text. Where the sweetener is prone to crystallization (such as with table sugar, i.e., sucrose), one or more interfering agents are necessary in order to ensure that the sweetener does not crystallize during the heating process. For example, where table sugar is used to prepare the lollipops, the corn syrup and cream of tartar are suitable interfering agents. The long glucose chains in the corn syrup prevent the sucrose from crystallizing and the cream of tartar prevents the crystallization of sucrose by converting the sucrose to fructose and glucose. In order to prevent the recrystallization of the sugar, the mixture should not be stirred after it has started to boil and the sides of the pan should be free of any sucrose crystals that could reseed the sucrose crystallization process. Once the mixture has boiled, the mixture should continue to heat, without stirring, until it has reached a temperature of 300-310° F.; this temperature range is known as the hard crack stage where there is almost no water left in the mixture and the sugar concentration of the mixture is approximately 99%. Once the syrup has reached the hard crack stage, the heat should be turned off and the mixture should be allowed to cool to 275° F. at which time the lollipop flavorings and colorings should be added to the mixture; adding the flavorings and colorings prior to this stage may result in the flavorings and colorings burning off during the cooking process. Once the mixture has cooled to 275° F., the mixture is poured into the lollipop molds, allowed to cool for 10 minutes, and wrapped in appropriate wrapping, such as cellophane or waxed paper. To preserve freshness, the finished lollipops should be stored in a cool, dry place.

Within the context of the present invention, where the composition is a lollipop as described above, any additional ingredients and/or active agents should be added to the lollipop along with the flavorings and colorings when the mixture is at 275° F.

Sweeteners that may be used with the present invention may be selected from a wide range of materials including water-soluble natural sweeteners, water-soluble artificial sweeteners, water-soluble sweeteners derived from naturally occurring water-soluble sweeteners, and mixtures thereof. Without being limited to particular sweeteners, representative categories and examples of sweeteners are shown in Table 1.

TABLE 1

| Water-soluble Natural Sweeteners (monosaccharides, disaccharides, and polysaccharides) | Water-soluble Artificial Sweeteners | Water-soluble Sweeteners Derived from Natural Substances |
| --- | --- | --- |
| Dextrose (D-glucose); fructose (levulose); galactose; maltose; mannose; sucrose (table sugar); ribulose; xylose; inverted sugar (a mixture of fructose and glucose derived from sucrose); glycyrrhizin (a natural sweetener derived from licorice root); steviosides (a natural sweetener derived from the leaves of the stevia plant); and naturally-occurring sweet proteins derived from plants, such as monellin, thaumatin, pentadin, mabinlin, and brazzein. | Soluble saccharine salts (e.g., sodium or calcium saccharine salts); aspartame; sodium cyclamate, and acesulfame potassium. | Sugar alcohols (polyols), such as erythritol, lacititol, maltitol, mannitol, sorbitol and xylitol; isomalt (a sugar alcohol derived from glucose and mannitol); hydrogenated starch hydrosylates (a mixture of sugar alcohols derived from corn starch, potato starch, or wheat starch) dihydrochalcones (an artificial sweetener derived from citrus); chlorinated derivatives of sucrose (sucralose); and corn syrup. |

Additional natural sweeteners that may be used in the preparation of the compositions of the present invention include, without limitation honey, maple syrup, evaporated cane juice, and one or more concentrated fruit juices. Honey gets its sweetness from a combination of the monosaccharides fructose and glucose and has the same relative sweetness level as the disaccharide sucrose (table sugar). Maple syrup consists primarily of sucrose and water, with small amounts of the fructose and glucose; the presence of malic acid makes maple syrup slightly acidic. Evaporated cane juice and concentrated fruit juices may include combinations of sugars, including fructose, glucose and sucrose.

Preferably, the composition of the present invention is prepared using one or more natural sweeteners, one or more sugar alcohols as set forth in Table 1, or a combination of one or more natural sweeteners and one or more sugar alcohols. Preferred water-soluble sugar-based sweeteners from Table 1 that may be used for the preparation of the compositions of the invention are dextrose, fructose, sucrose, mannitol, sorbitol, xylitol, and mixtures thereof. In some embodiments, the sweetening agent is selected from the group consisting of aspartame, cyclamate, saccharin, *stevia*, sucralose, xylitol, glucose, isomalt, arabitol, erythritol, glycerol, hydrogenated Starch Hydrosylate (HSH), lactitol, maltitol, and mixtures thereof.

As noted in Table 1, water-soluble sweeteners derived from natural substances include sugar alcohols, also referred to as "polyols." Polyols contribute between 0.2 and 3.0 calories per gram as opposed to sucrose, which contributes four calories per gram, and contribute not only to sweetness but also to bulk; accordingly, the use of polyols may be preferable in some formulations of the composition of the invention. Further, it is to be understood that compositions that are to be administered to diabetic patients should be prepared with non-natural sugars, such sucralose, isomalt, or the sugar alcohols and artificial sweeteners set forth in Table 1. In some embodiments, the sweetening agent is a sugar alcohol, e.g., selected from the group consisting of xylitol, mannitol, sorbitol, isomalt, arabitol, erythritol, glycerol, hydrogenated Starch Hydrolysate (HSH), lactitol, maltitol, and mixtures thereof.

The natural sweeteners may be present in the compositions of the present invention a range of about 2% w/w to about 95% w/w, preferably with a range of about 50% w/w to about 95% w/w. Because sweeteners derived from natural sources and artificial sweeteners tend to be much sweeter than natural sugars, such non-natural sugars may be present in a range of about 0.01% w/w to about 2% w/w, with a range of about 0.05% w/w to about 1% w/w preferred.

Any flavoring agent or combinations of flavoring agents may be used in the compositions of the present invention. Examples of flavoring agents that may be used in the invention are natural flavors and artificial flavors, and mixtures thereof. One example of flavoring agents that may be used to prepare the compositions of the present invention is OTTENS® flavorings (Philadelphia, Pa., USA). Natural flavoring agents include extracts and juices obtained from natural sources. Examples of sources to obtain the natural flavors for use in the compositions of the present invention include, without limitation, acai berries, aloe vera, apples, bananas, blueberries, cantaloupe, caramel, carrots, cherries, chocolate, coconut, coffee, cranberries, grapefruits, grapes, guava, honeydew melons, kiwi, lemons, licorice, limes, lychee fruits, mango, nectarines, olallieberries, oranges, peaches, pears, pineapples, pomegranates, raspberries, strawberries, tangerines, vanilla, watermelon, wheat grass, peppermint oil and spearmint oil.

The natural or artificial flavorings may be present in the compositions of the present invention in the range of about 0.005% w/w to about 5% w/w, with a range of about 0.05% w/w to about 3% w/w preferred.

It is to be understood that citric acid may be a suitable natural alternative to lemon and lime fruit flavorings. The chelating properties of citric acid have the additional benefit of acting as a natural antimicrobial preservative (discussed below). Further, citric acid may also be used to adjust the pH of the compositions of the present invention (discussed below).

In one embodiment of the invention, the composition includes a homeopathic agent. Examples of homeopathic agents that may be included in the composition of the present invention include, without limitation, Acontum Napellus, Allium Ceia, Arnica, Mullein, Belladona, Bellis Perennis, Calendula, Calcarea Carbonica, Chamomilla, Ferum Phosphorilum, Hamamelis, Hepar Sulphuris, Hypericum Perforatum (Saint John's Wort), Kau Bichromicum, Kau lodatum, Kau Muriaticum, Kau Sulphuricum, Lycopodium, Mercurius Solubilis, Mezereum, Millefolium, Natrum Sulphuricum, Phytolacca Decandra, Phosphorus, Pulsatilla, Sulphur, and Symphytum Officinale. The amount of homeopathic agents to be incorporated into the compositions of the present invention will range from 1c to 30c depending on the particular homeopathic agent, with each "c" value representing a 1/100 dilution (e.g., 1c is 0.01 of the original tincture, 2c is 0.0001 of the original tincture, etc.).

In another embodiment of the invention, the composition may include a vitamin and/or dietary supplement. Examples of vitamins and/or dietary supplements that may be included in the composition of the present invention include, without limitation, vitamin A (retinyl palmitate, retinol, and/or retinoic acid), vitamin B1 (thiamine), vitamin B2 (riboflavin), vitamin B3 (niacin and/or niacinamide), vitamin B5 (pantothenic acid), vitamin B6 (pyridoxine, pyridoxal, pyridoxamine, and/or pyridoxine hydrochloride), vitamin B7 (biotin), vitamin B8 (inositol), vitamin B9 (folic acid), vitamin B12 (cobalamins), a B complex vitamin, vitamin C, vitamin D (ergocalciferol—vitamin D2 and/or cholecalciferol—vitamin D3), vitamin E (tocopherols and/or tocotrienols), calcium, magnesium, manganese, potassium, selenium, and sodium bicarbonate. The amount of vitamins and/or dietary supplements to be incorporated into the composition of the present invention is the standard recommended daily intake (RDI) set by the Food and Drug Administration (FDA).

In a further embodiment of the invention, the composition may include an herb, oil, or flower extract. Examples of such extracts include, without limitation, bee propolis extract, chinese vitex, *echinacea*, elder, forsythia, garlic, ginger, goldenseal root extract, horehound, hyssop, isatis, lemon balm, lemon oil, linden flowers, *lonicera*, mallow, menthol, mineral oil, peppermint oil, spearmint oil, sage, schizonepeta, slippery elm bark extract, and wild thyme.

In another embodiment of the invention, the composition may include an essential or non-essential amino acid. As is known to those of skill in the art, the essential amino acids are isoleucine, leucine, lysine, methionine, phenylalanine, threonine, and tryptophan. The non-essential amino acids are alanine, arginine, asparagines, aspartic acid, cysteine, glutamic acid, glycine, histidine, ornithine, proline, selenocysteine, serine, taurine, and tyrosine.

Where appropriate, the compositions of the present invention may contain natural antimicrobial preservatives, such as for example, citric acid and its mineral salts and/or sorbic acid and its mineral salts. Mineral salts of citric acid that may be used as preservatives include sodium citrate (monosodium citrate, disodium citrate, and trisodium citrate) and calcium citrate. Mineral salts of sorbic acid that may be used as preservatives include sodium sorbate, potassium sorbate, and calcium sorbate. The optimal pH for the antimicrobial activity of the citric acid and sorbic acid mineral salts is typically below pH 6.5 and the mineral salts are generally used at concentrations of 0.025% to 0.10% w/w. Because adding mineral salts to food may raise the pH of the food slightly, the pH of the compositions of the present invention may need to be adjusted subsequent to the addition of the mineral salts in order to ensure that the mineral salts are capable of maintaining their antimicrobial activity. In various embodiments, the composition further comprises an antibiotic.

The compositions of the invention can also optionally include pharmaceutically acceptable buffering agents sufficient to adjust and maintain the pH of the composition of the present invention in the range of about 3.0 to about 6.5, preferably about 5.0 to about 6.5. Suitable buffering agents include, without limitation, citrate, phosphate, borate, or acetate salts, which can be derived from substances, such as citric acid, primary or secondary sodium phosphate, boric acid, sodium tetraborate, acetic acid, and sodium acetate, respectively. Other suitable buffering agents are tromethamine and glycine. Where appropriate, the pH of the composition of the present invention may be adjusted with the addition of a suitable acid such as citric acid, phosphoric acid, succinic acid, or tartaric acid in a quantity suitable to achieve a pH in the range of 4.0 to 8.0. Hydrochloric acid or sodium hydroxide can also be used for pH adjustment.

In some embodiments, the composition comprises 1, 2, 3, 4, 5, or more, active ingredients selected from the group consisting of vitamin A, vitamin B1, vitamin B2, vitamin B3, vitamin B5, vitamin B6, vitamin B7, vitamin B8, vitamin B9, vitamin B12, a B complex vitamin, vitamin C, vitamin E, zinc, magnesium, selenium, *echinacea*, olive leaf, wild indigo, goldenseal, fenugreek, mullein (*verbascum olympicum* and *thapsus*), phenol, camphor, pectin, *eucalyptus* oil, peppermint oil, spearmint oil, and mixtures thereof.

For example, in some embodiments, the composition includes (e.g., comprises, consists of, or consists essentially of) 2 or more ingredients selected from the combinations listed in Table 2.

TABLE 2

Two Ingredient Combinations

| First Ingredient | Second Ingredient |
| --- | --- |
| Vitamin A | Vitamin B1 |
| Vitamin A | Vitamin B2 |
| Vitamin A | Vitamin B3 |
| Vitamin A | Vitamin B5 |
| Vitamin A | Vitamin B6 |
| Vitamin A | Vitamin B7 |
| Vitamin A | Vitamin B8 |
| Vitamin A | Vitamin B9 |
| Vitamin A | Vitamin B12 |
| Vitamin A | Vitamin C |
| Vitamin A | Vitamin E |
| Vitamin A | Zinc |
| Vitamin A | Magnesium |
| Vitamin A | Selenium |
| Vitamin A | Echinacea |
| Vitamin A | Olive leaf |
| Vitamin A | Wild indigo |
| Vitamin A | Goldenseal |
| Vitamin A | Fenugreek |
| Vitamin A | Mullein |
| Vitamin A | Phenol |
| Vitamin A | Camphor |
| Vitamin A | Pectin |
| Vitamin A | Eucalyptus Oil |
| Vitamin A | Peppermint Oil |
| Vitamin A | Spearmint Oil |
| Vitamin B1 | Vitamin B2 |
| Vitamin B1 | Vitamin B3 |
| Vitamin B1 | Vitamin B5 |
| Vitamin B1 | Vitamin B6 |
| Vitamin B1 | Vitamin B7 |
| Vitamin B1 | Vitamin B8 |
| Vitamin B1 | Vitamin B9 |
| Vitamin B1 | Vitamin B12 |
| Vitamin B1 | Vitamin C |
| Vitamin B1 | Vitamin E |
| Vitamin B1 | Zinc |
| Vitamin B1 | Magnesium |
| Vitamin B1 | Selenium |
| Vitamin B1 | Echinacea |
| Vitamin B1 | Olive leaf |
| Vitamin B1 | Wild indigo |
| Vitamin B1 | Goldenseal |
| Vitamin B1 | Fenugreek |
| Vitamin B1 | Mullein |
| Vitamin B1 | Phenol |
| Vitamin B1 | Camphor |
| Vitamin B1 | Pectin |
| Vitamin B1 | Eucalyptus Oil |
| Vitamin B1 | Peppermint Oil |
| Vitamin B1 | Spearmint Oil |
| Vitamin B2 | Vitamin B3 |
| Vitamin B2 | Vitamin B5 |
| Vitamin B2 | Vitamin B6 |
| Vitamin B2 | Vitamin B7 |
| Vitamin B2 | Vitamin B8 |
| Vitamin B2 | Vitamin B9 |
| Vitamin B2 | Vitamin B12 |
| Vitamin B2 | Vitamin C |
| Vitamin B2 | Vitamin E |
| Vitamin B2 | Zinc |
| Vitamin B2 | Magnesium |
| Vitamin B2 | Selenium |
| Vitamin B2 | Echinacea |
| Vitamin B2 | Olive leaf |
| Vitamin B2 | Wild indigo |
| Vitamin B2 | Goldenseal |
| Vitamin B2 | Fenugreek |
| Vitamin B2 | Mullein |
| Vitamin B2 | Phenol |
| Vitamin B2 | Camphor |
| Vitamin B2 | Pectin |
| Vitamin B2 | Eucalyptus Oil |
| Vitamin B2 | Peppermint Oil |
| Vitamin B2 | Spearmint Oil |
| Vitamin B3 | Vitamin B5 |
| Vitamin B3 | Vitamin B6 |
| Vitamin B3 | Vitamin B7 |
| Vitamin B3 | Vitamin B8 |
| Vitamin B3 | Vitamin B9 |
| Vitamin B3 | Vitamin B12 |
| Vitamin B3 | Vitamin C |
| Vitamin B3 | Vitamin E |
| Vitamin B3 | Zinc |
| Vitamin B3 | Magnesium |
| Vitamin B3 | Selenium |
| Vitamin B3 | Echinacea |
| Vitamin B3 | Olive leaf |
| Vitamin B3 | Wild indigo |
| Vitamin B3 | Goldenseal |
| Vitamin B3 | Fenugreek |
| Vitamin B3 | Mullein |
| Vitamin B3 | Phenol |
| Vitamin B3 | Camphor |
| Vitamin B3 | Pectin |
| Vitamin B3 | Eucalyptus Oil |
| Vitamin B3 | Peppermint Oil |
| Vitamin B3 | Spearmint Oil |
| Vitamin B5 | Vitamin B6 |
| Vitamin B5 | Vitamin B7 |
| Vitamin B5 | Vitamin B8 |
| Vitamin B5 | Vitamin B9 |
| Vitamin B5 | Vitamin B12 |
| Vitamin B5 | Vitamin C |
| Vitamin B5 | Vitamin E |
| Vitamin B5 | Zinc |
| Vitamin B5 | Magnesium |
| Vitamin B5 | Selenium |
| Vitamin B5 | Echinacea |
| Vitamin B5 | Olive leaf |
| Vitamin B5 | Wild indigo |
| Vitamin B5 | Goldenseal |
| Vitamin B5 | Fenugreek |
| Vitamin B5 | Mullein |
| Vitamin B5 | Phenol |
| Vitamin B5 | Camphor |
| Vitamin B5 | Pectin |
| Vitamin B5 | Eucalyptus Oil |
| Vitamin B5 | Peppermint Oil |
| Vitamin B5 | Spearmint Oil |
| Vitamin B6 | Vitamin B7 |
| Vitamin B6 | Vitamin B8 |
| Vitamin B6 | Vitamin B9 |

TABLE 2-continued

Two Ingredient Combinations

| First Ingredient | Second Ingredient |
|---|---|
| Vitamin B6 | Vitamin B12 |
| Vitamin B6 | Vitamin C |
| Vitamin B6 | Vitamin E |
| Vitamin B6 | Zinc |
| Vitamin B6 | Magnesium |
| Vitamin B6 | Selenium |
| Vitamin B6 | Echinacea |
| Vitamin B6 | Olive leaf |
| Vitamin B6 | Wild indigo |
| Vitamin B6 | Goldenseal |
| Vitamin B6 | Fenugreek |
| Vitamin B6 | Mullein |
| Vitamin B6 | Phenol |
| Vitamin B6 | Camphor |
| Vitamin B6 | Pectin |
| Vitamin B6 | Eucalyptus Oil |
| Vitamin B6 | Peppermint Oil |
| Vitamin B6 | Spearmint Oil |
| Vitamin B7 | Vitamin B8 |
| Vitamin B7 | Vitamin B9 |
| Vitamin B7 | Vitamin B12 |
| Vitamin B7 | Vitamin C |
| Vitamin B7 | Vitamin E |
| Vitamin B7 | Zinc |
| Vitamin B7 | Magnesium |
| Vitamin B7 | Selenium |
| Vitamin B7 | Echinacea |
| Vitamin B7 | Olive leaf |
| Vitamin B7 | Wild indigo |
| Vitamin B7 | Goldenseal |
| Vitamin B7 | Fenugreek |
| Vitamin B7 | Mullein |
| Vitamin B7 | Phenol |
| Vitamin B7 | Camphor |
| Vitamin B7 | Pectin |
| Vitamin B7 | Eucalyptus Oil |
| Vitamin B7 | Peppermint Oil |
| Vitamin B7 | Spearmint Oil |
| Vitamin B8 | Vitamin B9 |
| Vitamin B8 | Vitamin B12 |
| Vitamin B8 | Vitamin C |
| Vitamin B8 | Vitamin E |
| Vitamin B8 | Zinc |
| Vitamin B8 | Magnesium |
| Vitamin B8 | Selenium |
| Vitamin B8 | Echinacea |
| Vitamin B8 | Olive leaf |
| Vitamin B8 | Wild indigo |
| Vitamin B8 | Goldenseal |
| Vitamin B8 | Fenugreek |
| Vitamin B8 | Mullein |
| Vitamin B8 | Phenol |
| Vitamin B8 | Camphor |
| Vitamin B8 | Pectin |
| Vitamin B8 | Eucalyptus Oil |
| Vitamin B8 | Peppermint Oil |
| Vitamin B8 | Spearmint Oil |
| Vitamin B9 | Vitamin B12 |
| Vitamin B9 | Vitamin C |
| Vitamin B9 | Vitamin E |
| Vitamin B9 | Zinc |
| Vitamin B9 | Magnesium |
| Vitamin B9 | Selenium |
| Vitamin B9 | Echinacea |
| Vitamin B9 | Olive leaf |
| Vitamin B9 | Wild indigo |
| Vitamin B9 | Goldenseal |
| Vitamin B9 | Fenugreek |
| Vitamin B9 | Mullein |
| Vitamin B9 | Phenol |
| Vitamin B9 | Camphor |
| Vitamin B9 | Pectin |
| Vitamin B9 | Eucalyptus Oil |
| Vitamin B9 | Peppermint Oil |
| Vitamin B9 | Spearmint Oil |
| Vitamin B12 | Vitamin C |
| Vitamin B12 | Vitamin E |
| Vitamin B12 | Zinc |
| Vitamin B12 | Magnesium |
| Vitamin B12 | Selenium |
| Vitamin B12 | Echinacea |
| Vitamin B12 | Olive leaf |
| Vitamin B12 | Wild indigo |
| Vitamin B12 | Goldenseal |
| Vitamin B12 | Fenugreek |
| Vitamin B12 | Mullein |
| Vitamin B12 | Phenol |
| Vitamin B12 | Camphor |
| Vitamin B12 | Pectin |
| Vitamin B12 | Eucalyptus Oil |
| Vitamin B12 | Peppermint Oil |
| Vitamin B12 | Spearmint Oil |
| Vitamin C | Vitamin E |
| Vitamin C | Zinc |
| Vitamin C | Magnesium |
| Vitamin C | Selenium |
| Vitamin C | Echinacea |
| Vitamin C | Olive leaf |
| Vitamin C | Wild indigo |
| Vitamin C | Goldenseal |
| Vitamin C | Fenugreek |
| Vitamin C | Mullein |
| Vitamin C | Phenol |
| Vitamin C | Camphor |
| Vitamin C | Pectin |
| Vitamin C | Eucalyptus Oil |
| Vitamin C | Peppermint Oil |
| Vitamin C | Spearmint Oil |
| Vitamin E | Zinc |
| Vitamin E | Magnesium |
| Vitamin E | Selenium |
| Vitamin E | Echinacea |
| Vitamin E | Olive leaf |
| Vitamin E | Wild indigo |
| Vitamin E | Goldenseal |
| Vitamin E | Fenugreek |
| Vitamin E | Mullein |
| Vitamin E | Phenol |
| Vitamin E | Camphor |
| Vitamin E | Pectin |
| Vitamin E | Eucalyptus Oil |
| Vitamin E | Peppermint Oil |
| Vitamin E | Spearmint Oil |
| Zinc | Magnesium |
| Zinc | Selenium |
| Zinc | Echinacea |
| Zinc | Olive leaf |
| Zinc | Wild indigo |
| Zinc | Goldenseal |
| Zinc | Fenugreek |
| Zinc | Mullein |
| Zinc | Phenol |
| Zinc | Camphor |
| Zinc | Pectin |
| Zinc | Eucalyptus Oil |
| Zinc | Peppermint Oil |
| Zinc | Spearmint Oil |
| Magnesium | Selenium |
| Magnesium | Echinacea |
| Magnesium | Olive leaf |
| Magnesium | Wild indigo |
| Magnesium | Goldenseal |
| Magnesium | Fenugreek |
| Magnesium | Mullein |
| Magnesium | Phenol |
| Magnesium | Camphor |
| Magnesium | Pectin |
| Magnesium | Eucalyptus Oil |
| Magnesium | Peppermint Oil |
| Magnesium | Spearmint Oil |
| Selenium | Echinacea |
| Selenium | Olive leaf |

TABLE 2-continued

Two Ingredient Combinations

| First Ingredient | Second Ingredient |
| --- | --- |
| Selenium | Wild indigo |
| Selenium | Goldenseal |
| Selenium | Fenugreek |
| Selenium | Mullein |
| Selenium | Phenol |
| Selenium | Camphor |
| Selenium | Pectin |
| Selenium | Eucalyptus Oil |
| Selenium | Peppermint Oil |
| Selenium | Spearmint Oil |
| *Echinacea* | Olive leaf |
| *Echinacea* | Wild indigo |
| *Echinacea* | Goldenseal |
| *Echinacea* | Fenugreek |
| *Echinacea* | Mullein |
| *Echinacea* | Phenol |
| *Echinacea* | Camphor |
| *Echinacea* | Pectin |
| *Echinacea* | Eucalyptus Oil |
| *Echinacea* | Peppermint Oil |
| *Echinacea* | Spearmint Oil |
| Olive leaf | Wild indigo |
| Olive leaf | Goldenseal |
| Olive leaf | Fenugreek |
| Olive leaf | Mullein |
| Olive leaf | Phenol |
| Olive leaf | Camphor |
| Olive leaf | Pectin |
| Olive leaf | Eucalyptus Oil |
| Olive leaf | Peppermint Oil |
| Olive leaf | Spearmint Oil |
| Wild indigo | Goldenseal |
| Wild indigo | Fenugreek |
| Wild indigo | Mullein |
| Wild indigo | Phenol |
| Wild indigo | Camphor |
| Wild indigo | Pectin |
| Wild indigo | Eucalyptus Oil |
| Wild indigo | Peppermint Oil |
| Wild indigo | Spearmint Oil |
| Goldenseal | Fenugreek |
| Goldenseal | Mullein |
| Goldenseal | Phenol |
| Goldenseal | Camphor |
| Goldenseal | Pectin |
| Goldenseal | Eucalyptus Oil |
| Goldenseal | Peppermint Oil |
| Goldenseal | Spearmint Oil |
| Fenugreek | Mullein |
| Fenugreek | Phenol |
| Fenugreek | Camphor |
| Fenugreek | Pectin |
| Fenugreek | Eucalyptus Oil |
| Fenugreek | Peppermint Oil |
| Fenugreek | Spearmint Oil |
| Mullein | Phenol |
| Mullein | Camphor |
| Mullein | Pectin |
| Mullein | Eucalyptus Oil |
| Mullein | Peppermint Oil |
| Mullein | Spearmint Oil |
| Phenol | Camphor |
| Phenol | Pectin |
| Phenol | Eucalyptus Oil |
| Phenol | Peppermint Oil |
| Phenol | Spearmint Oil |
| Camphor | Pectin |
| Camphor | Eucalyptus Oil |
| Camphor | Peppermint Oil |
| Camphor | Spearmint Oil |
| Pectin | Eucalyptus Oil |
| Pectin | Peppermint Oil |
| Pectin | Spearmint Oil |
| Eucalyptus Oil | Peppermint Oil |
| Eucalyptus Oil | Spearmint Oil |
| Peppermint Oil | Spearmint Oil |

For example, in some embodiments, the composition includes (e.g., comprises, consists of, or consists essentially of) 3 or more ingredients selected from the combinations listed in Table 3.

TABLE 3

Three Ingredient Combinations

| First Ingredient | Second Ingredient | Third Ingredient |
| --- | --- | --- |
| Vitamin A | Vitamin B1 | Vitamin B2 |
| Vitamin A | Vitamin B1 | Vitamin B3 |
| Vitamin A | Vitamin B1 | Vitamin B5 |
| Vitamin A | Vitamin B1 | Vitamin B6 |
| Vitamin A | Vitamin B1 | Vitamin B7 |
| Vitamin A | Vitamin B1 | Vitamin B8 |
| Vitamin A | Vitamin B1 | Vitamin B9 |
| Vitamin A | Vitamin B1 | Vitamin B12 |
| Vitamin A | Vitamin B1 | Vitamin C |
| Vitamin A | Vitamin B1 | Vitamin E |
| Vitamin A | Vitamin B1 | Zinc |
| Vitamin A | Vitamin B1 | Magnesium |
| Vitamin A | Vitamin B1 | Selenium |
| Vitamin A | Vitamin B1 | Echinacea |
| Vitamin A | Vitamin B1 | Olive leaf |
| Vitamin A | Vitamin B1 | Wild indigo |
| Vitamin A | Vitamin B1 | Goldenseal |
| Vitamin A | Vitamin B1 | Fenugreek |
| Vitamin A | Vitamin B1 | Mullein |
| Vitamin A | Vitamin B1 | Phenol |
| Vitamin A | Vitamin B1 | Camphor |
| Vitamin A | Vitamin B1 | Pectin |
| Vitamin A | Vitamin B1 | Eucalyptus Oil |
| Vitamin A | Vitamin B1 | Peppermint Oil |
| Vitamin A | Vitamin B1 | Spearmint Oil |
| Vitamin A | Vitamin B2 | Vitamin B3 |
| Vitamin A | Vitamin B2 | Vitamin B5 |
| Vitamin A | Vitamin B2 | Vitamin B6 |
| Vitamin A | Vitamin B2 | Vitamin B7 |
| Vitamin A | Vitamin B2 | Vitamin B8 |
| Vitamin A | Vitamin B2 | Vitamin B9 |
| Vitamin A | Vitamin B2 | Vitamin B12 |
| Vitamin A | Vitamin B2 | Vitamin C |
| Vitamin A | Vitamin B2 | Vitamin E |
| Vitamin A | Vitamin B2 | Zinc |
| Vitamin A | Vitamin B2 | Magnesium |
| Vitamin A | Vitamin B2 | Selenium |
| Vitamin A | Vitamin B2 | Echinacea |
| Vitamin A | Vitamin B2 | Olive leaf |
| Vitamin A | Vitamin B2 | Wild indigo |
| Vitamin A | Vitamin B2 | Goldenseal |
| Vitamin A | Vitamin B2 | Fenugreek |
| Vitamin A | Vitamin B2 | Mullein |
| Vitamin A | Vitamin B2 | Phenol |
| Vitamin A | Vitamin B2 | Camphor |
| Vitamin A | Vitamin B2 | Pectin |
| Vitamin A | Vitamin B2 | Eucalyptus Oil |
| Vitamin A | Vitamin B2 | Peppermint Oil |
| Vitamin A | Vitamin B2 | Spearmint Oil |
| Vitamin A | Vitamin B3 | Vitamin B5 |
| Vitamin A | Vitamin B3 | Vitamin B6 |
| Vitamin A | Vitamin B3 | Vitamin B7 |
| Vitamin A | Vitamin B3 | Vitamin B8 |
| Vitamin A | Vitamin B3 | Vitamin B9 |
| Vitamin A | Vitamin B3 | Vitamin B12 |
| Vitamin A | Vitamin B3 | Vitamin C |
| Vitamin A | Vitamin B3 | Vitamin E |
| Vitamin A | Vitamin B3 | Zinc |
| Vitamin A | Vitamin B3 | Magnesium |
| Vitamin A | Vitamin B3 | Selenium |

TABLE 3-continued

Three Ingredient Combinations

| First Ingredient | Second Ingredient | Third Ingredient |
|---|---|---|
| Vitamin A | Vitamin B3 | Echinacea |
| Vitamin A | Vitamin B3 | Olive leaf |
| Vitamin A | Vitamin B3 | Wild indigo |
| Vitamin A | Vitamin B3 | Goldenseal |
| Vitamin A | Vitamin B3 | Fenugreek |
| Vitamin A | Vitamin B3 | Mullein |
| Vitamin A | Vitamin B3 | Phenol |
| Vitamin A | Vitamin B3 | Camphor |
| Vitamin A | Vitamin B3 | Pectin |
| Vitamin A | Vitamin B3 | Eucalyptus Oil |
| Vitamin A | Vitamin B3 | Peppermint Oil |
| Vitamin A | Vitamin B3 | Spearmint Oil |
| Vitamin A | Vitamin B5 | Vitamin B6 |
| Vitamin A | Vitamin B5 | Vitamin B7 |
| Vitamin A | Vitamin B5 | Vitamin B8 |
| Vitamin A | Vitamin B5 | Vitamin B9 |
| Vitamin A | Vitamin B5 | Vitamin B12 |
| Vitamin A | Vitamin B5 | Vitamin C |
| Vitamin A | Vitamin B5 | Vitamin E |
| Vitamin A | Vitamin B5 | Zinc |
| Vitamin A | Vitamin B5 | Magnesium |
| Vitamin A | Vitamin B5 | Selenium |
| Vitamin A | Vitamin B5 | Echinacea |
| Vitamin A | Vitamin B5 | Olive leaf |
| Vitamin A | Vitamin B5 | Wild indigo |
| Vitamin A | Vitamin B5 | Goldenseal |
| Vitamin A | Vitamin B5 | Fenugreek |
| Vitamin A | Vitamin B5 | Mullein |
| Vitamin A | Vitamin B5 | Phenol |
| Vitamin A | Vitamin B5 | Camphor |
| Vitamin A | Vitamin B5 | Pectin |
| Vitamin A | Vitamin B5 | Eucalyptus Oil |
| Vitamin A | Vitamin B5 | Peppermint Oil |
| Vitamin A | Vitamin B5 | Spearmint Oil |
| Vitamin A | Vitamin B6 | Vitamin B7 |
| Vitamin A | Vitamin B6 | Vitamin B8 |
| Vitamin A | Vitamin B6 | Vitamin B9 |
| Vitamin A | Vitamin B6 | Vitamin B12 |
| Vitamin A | Vitamin B6 | Vitamin C |
| Vitamin A | Vitamin B6 | Vitamin E |
| Vitamin A | Vitamin B6 | Zinc |
| Vitamin A | Vitamin B6 | Magnesium |
| Vitamin A | Vitamin B6 | Selenium |
| Vitamin A | Vitamin B6 | Echinacea |
| Vitamin A | Vitamin B6 | Olive leaf |
| Vitamin A | Vitamin B6 | Wild indigo |
| Vitamin A | Vitamin B6 | Goldenseal |
| Vitamin A | Vitamin B6 | Fenugreek |
| Vitamin A | Vitamin B6 | Mullein |
| Vitamin A | Vitamin B6 | Phenol |
| Vitamin A | Vitamin B6 | Camphor |
| Vitamin A | Vitamin B6 | Pectin |
| Vitamin A | Vitamin B6 | Eucalyptus Oil |
| Vitamin A | Vitamin B6 | Peppermint Oil |
| Vitamin A | Vitamin B6 | Spearmint Oil |
| Vitamin A | Vitamin B7 | Vitamin B8 |
| Vitamin A | Vitamin B7 | Vitamin B9 |
| Vitamin A | Vitamin B7 | Vitamin B12 |
| Vitamin A | Vitamin B7 | Vitamin C |
| Vitamin A | Vitamin B7 | Vitamin E |
| Vitamin A | Vitamin B7 | Zinc |
| Vitamin A | Vitamin B7 | Magnesium |
| Vitamin A | Vitamin B7 | Selenium |
| Vitamin A | Vitamin B7 | Echinacea |
| Vitamin A | Vitamin B7 | Olive leaf |
| Vitamin A | Vitamin B7 | Wild indigo |
| Vitamin A | Vitamin B7 | Goldenseal |
| Vitamin A | Vitamin B7 | Fenugreek |
| Vitamin A | Vitamin B7 | Mullein |
| Vitamin A | Vitamin B7 | Phenol |
| Vitamin A | Vitamin B7 | Camphor |
| Vitamin A | Vitamin B7 | Pectin |
| Vitamin A | Vitamin B7 | Eucalyptus Oil |
| Vitamin A | Vitamin B7 | Peppermint Oil |
| Vitamin A | Vitamin B7 | Spearmint Oil |
| Vitamin A | Vitamin B8 | Vitamin B9 |
| Vitamin A | Vitamin B8 | Vitamin B12 |
| Vitamin A | Vitamin B8 | Vitamin C |
| Vitamin A | Vitamin B8 | Vitamin E |
| Vitamin A | Vitamin B8 | Zinc |
| Vitamin A | Vitamin B8 | Magnesium |
| Vitamin A | Vitamin B8 | Selenium |
| Vitamin A | Vitamin B8 | Echinacea |
| Vitamin A | Vitamin B8 | Olive leaf |
| Vitamin A | Vitamin B8 | Wild indigo |
| Vitamin A | Vitamin B8 | Goldenseal |
| Vitamin A | Vitamin B8 | Fenugreek |
| Vitamin A | Vitamin B8 | Mullein |
| Vitamin A | Vitamin B8 | Phenol |
| Vitamin A | Vitamin B8 | Camphor |
| Vitamin A | Vitamin B8 | Pectin |
| Vitamin A | Vitamin B8 | Eucalyptus Oil |
| Vitamin A | Vitamin B8 | Peppermint Oil |
| Vitamin A | Vitamin B8 | Spearmint Oil |
| Vitamin A | Vitamin B9 | Vitamin B12 |
| Vitamin A | Vitamin B9 | Vitamin C |
| Vitamin A | Vitamin B9 | Vitamin E |
| Vitamin A | Vitamin B9 | Zinc |
| Vitamin A | Vitamin B9 | Magnesium |
| Vitamin A | Vitamin B9 | Selenium |
| Vitamin A | Vitamin B9 | Echinacea |
| Vitamin A | Vitamin B9 | Olive leaf |
| Vitamin A | Vitamin B9 | Wild indigo |
| Vitamin A | Vitamin B9 | Goldenseal |
| Vitamin A | Vitamin B9 | Fenugreek |
| Vitamin A | Vitamin B9 | Mullein |
| Vitamin A | Vitamin B9 | Phenol |
| Vitamin A | Vitamin B9 | Camphor |
| Vitamin A | Vitamin B9 | Pectin |
| Vitamin A | Vitamin B9 | Eucalyptus Oil |
| Vitamin A | Vitamin B9 | Peppermint Oil |
| Vitamin A | Vitamin B9 | Spearmint Oil |
| Vitamin A | Vitamin B12 | Vitamin C |
| Vitamin A | Vitamin B12 | Vitamin E |
| Vitamin A | Vitamin B12 | Zinc |
| Vitamin A | Vitamin B12 | Magnesium |
| Vitamin A | Vitamin B12 | Selenium |
| Vitamin A | Vitamin B12 | Echinacea |
| Vitamin A | Vitamin B12 | Olive leaf |
| Vitamin A | Vitamin B12 | Wild indigo |
| Vitamin A | Vitamin B12 | Goldenseal |
| Vitamin A | Vitamin B12 | Fenugreek |
| Vitamin A | Vitamin B12 | Mullein |
| Vitamin A | Vitamin B12 | Phenol |
| Vitamin A | Vitamin B12 | Camphor |
| Vitamin A | Vitamin B12 | Pectin |
| Vitamin A | Vitamin B12 | Eucalyptus Oil |
| Vitamin A | Vitamin B12 | Peppermint Oil |
| Vitamin A | Vitamin B12 | Spearmint Oil |
| Vitamin A | Vitamin C | Vitamin E |
| Vitamin A | Vitamin C | Zinc |
| Vitamin A | Vitamin C | Magnesium |
| Vitamin A | Vitamin C | Selenium |
| Vitamin A | Vitamin C | Echinacea |
| Vitamin A | Vitamin C | Olive leaf |
| Vitamin A | Vitamin C | Wild indigo |
| Vitamin A | Vitamin C | Goldenseal |
| Vitamin A | Vitamin C | Fenugreek |
| Vitamin A | Vitamin C | Mullein |
| Vitamin A | Vitamin C | Phenol |
| Vitamin A | Vitamin C | Camphor |
| Vitamin A | Vitamin C | Pectin |
| Vitamin A | Vitamin C | Eucalyptus Oil |
| Vitamin A | Vitamin C | Peppermint Oil |
| Vitamin A | Vitamin C | Spearmint Oil |
| Vitamin A | Vitamin E | Zinc |
| Vitamin A | Vitamin E | Magnesium |
| Vitamin A | Vitamin E | Selenium |
| Vitamin A | Vitamin E | Echinacea |
| Vitamin A | Vitamin E | Olive leaf |
| Vitamin A | Vitamin E | Wild indigo |
| Vitamin A | Vitamin E | Goldenseal |

TABLE 3-continued

Three Ingredient Combinations

| First Ingredient | Second Ingredient | Third Ingredient |
|---|---|---|
| Vitamin A | Vitamin E | Fenugreek |
| Vitamin A | Vitamin E | Mullein |
| Vitamin A | Vitamin E | Phenol |
| Vitamin A | Vitamin E | Camphor |
| Vitamin A | Vitamin E | Pectin |
| Vitamin A | Vitamin E | Eucalyptus Oil |
| Vitamin A | Vitamin E | Peppermint Oil |
| Vitamin A | Vitamin E | Spearmint Oil |
| Vitamin A | Zinc | Magnesium |
| Vitamin A | Zinc | Selenium |
| Vitamin A | Zinc | Echinacea |
| Vitamin A | Zinc | Olive leaf |
| Vitamin A | Zinc | Wild indigo |
| Vitamin A | Zinc | Goldenseal |
| Vitamin A | Zinc | Fenugreek |
| Vitamin A | Zinc | Mullein |
| Vitamin A | Zinc | Phenol |
| Vitamin A | Zinc | Camphor |
| Vitamin A | Zinc | Pectin |
| Vitamin A | Zinc | Eucalyptus Oil |
| Vitamin A | Zinc | Peppermint Oil |
| Vitamin A | Zinc | Spearmint Oil |
| Vitamin A | Magnesium | Selenium |
| Vitamin A | Magnesium | Echinacea |
| Vitamin A | Magnesium | Olive leaf |
| Vitamin A | Magnesium | Wild indigo |
| Vitamin A | Magnesium | Goldenseal |
| Vitamin A | Magnesium | Fenugreek |
| Vitamin A | Magnesium | Mullein |
| Vitamin A | Magnesium | Phenol |
| Vitamin A | Magnesium | Camphor |
| Vitamin A | Magnesium | Pectin |
| Vitamin A | Magnesium | Eucalyptus Oil |
| Vitamin A | Magnesium | Peppermint Oil |
| Vitamin A | Magnesium | Spearmint Oil |
| Vitamin A | Selenium | Echinacea |
| Vitamin A | Selenium | Olive leaf |
| Vitamin A | Selenium | Wild indigo |
| Vitamin A | Selenium | Goldenseal |
| Vitamin A | Selenium | Fenugreek |
| Vitamin A | Selenium | Mullein |
| Vitamin A | Selenium | Phenol |
| Vitamin A | Selenium | Camphor |
| Vitamin A | Selenium | Pectin |
| Vitamin A | Selenium | Eucalyptus Oil |
| Vitamin A | Selenium | Peppermint Oil |
| Vitamin A | Selenium | Spearmint Oil |
| Vitamin A | Echinacea | Olive leaf |
| Vitamin A | Echinacea | Wild indigo |
| Vitamin A | Echinacea | Goldenseal |
| Vitamin A | Echinacea | Fenugreek |
| Vitamin A | Echinacea | Mullein |
| Vitamin A | Echinacea | Phenol |
| Vitamin A | Echinacea | Camphor |
| Vitamin A | Echinacea | Pectin |
| Vitamin A | Echinacea | Eucalyptus Oil |
| Vitamin A | Echinacea | Peppermint Oil |
| Vitamin A | Echinacea | Spearmint Oil |
| Vitamin A | Olive leaf | Wild indigo |
| Vitamin A | Olive leaf | Goldenseal |
| Vitamin A | Olive leaf | Fenugreek |
| Vitamin A | Olive leaf | Mullein |
| Vitamin A | Olive leaf | Phenol |
| Vitamin A | Olive leaf | Camphor |
| Vitamin A | Olive leaf | Pectin |
| Vitamin A | Olive leaf | Eucalyptus Oil |
| Vitamin A | Olive leaf | Peppermint Oil |
| Vitamin A | Olive leaf | Spearmint Oil |
| Vitamin A | Wild indigo | Goldenseal |
| Vitamin A | Wild indigo | Fenugreek |
| Vitamin A | Wild indigo | Mullein |
| Vitamin A | Wild indigo | Phenol |
| Vitamin A | Wild indigo | Camphor |
| Vitamin A | Wild indigo | Pectin |
| Vitamin A | Wild indigo | Eucalyptus Oil |
| Vitamin A | Wild indigo | Peppermint Oil |
| Vitamin A | Wild indigo | Spearmint Oil |
| Vitamin A | Goldenseal | Fenugreek |
| Vitamin A | Goldenseal | Mullein |
| Vitamin A | Goldenseal | Phenol |
| Vitamin A | Goldenseal | Camphor |
| Vitamin A | Goldenseal | Pectin |
| Vitamin A | Goldenseal | Eucalyptus Oil |
| Vitamin A | Goldenseal | Peppermint Oil |
| Vitamin A | Goldenseal | Spearmint Oil |
| Vitamin A | Fenugreek | Mullein |
| Vitamin A | Fenugreek | Phenol |
| Vitamin A | Fenugreek | Camphor |
| Vitamin A | Fenugreek | Pectin |
| Vitamin A | Fenugreek | Eucalyptus Oil |
| Vitamin A | Fenugreek | Peppermint Oil |
| Vitamin A | Fenugreek | Spearmint Oil |
| Vitamin A | Mullein | Phenol |
| Vitamin A | Mullein | Camphor |
| Vitamin A | Mullein | Pectin |
| Vitamin A | Mullein | Eucalyptus Oil |
| Vitamin A | Mullein | Peppermint Oil |
| Vitamin A | Mullein | Spearmint Oil |
| Vitamin A | Phenol | Camphor |
| Vitamin A | Phenol | Pectin |
| Vitamin A | Phenol | Eucalyptus Oil |
| Vitamin A | Phenol | Peppermint Oil |
| Vitamin A | Phenol | Spearmint Oil |
| Vitamin A | Camphor | Pectin |
| Vitamin A | Camphor | Eucalyptus Oil |
| Vitamin A | Camphor | Peppermint Oil |
| Vitamin A | Camphor | Spearmint Oil |
| Vitamin A | Pectin | Eucalyptus Oil |
| Vitamin A | Pectin | Peppermint Oil |
| Vitamin A | Pectin | Spearmint Oil |
| Vitamin A | Eucalyptus Oil | Peppermint Oil |
| Vitamin A | Eucalyptus Oil | Spearmint Oil |
| Vitamin A | Peppermint Oil | Spearmint Oil |
| Vitamin B1 | Vitamin B2 | Vitamin B3 |
| Vitamin B1 | Vitamin B2 | Vitamin B5 |
| Vitamin B1 | Vitamin B2 | Vitamin B6 |
| Vitamin B1 | Vitamin B2 | Vitamin B7 |
| Vitamin B1 | Vitamin B2 | Vitamin B8 |
| Vitamin B1 | Vitamin B2 | Vitamin B9 |
| Vitamin B1 | Vitamin B2 | Vitamin B12 |
| Vitamin B1 | Vitamin B2 | Vitamin C |
| Vitamin B1 | Vitamin B2 | Vitamin E |
| Vitamin B1 | Vitamin B2 | Zinc |
| Vitamin B1 | Vitamin B2 | Magnesium |
| Vitamin B1 | Vitamin B2 | Selenium |
| Vitamin B1 | Vitamin B2 | Echinacea |
| Vitamin B1 | Vitamin B2 | Olive leaf |
| Vitamin B1 | Vitamin B2 | Wild indigo |
| Vitamin B1 | Vitamin B2 | Goldenseal |
| Vitamin B1 | Vitamin B2 | Fenugreek |
| Vitamin B1 | Vitamin B2 | Mullein |
| Vitamin B1 | Vitamin B2 | Phenol |
| Vitamin B1 | Vitamin B2 | Camphor |
| Vitamin B1 | Vitamin B2 | Pectin |
| Vitamin B1 | Vitamin B2 | Eucalyptus Oil |
| Vitamin B1 | Vitamin B2 | Peppermint Oil |
| Vitamin B1 | Vitamin B2 | Spearmint Oil |
| Vitamin B1 | Vitamin B3 | Vitamin B5 |
| Vitamin B1 | Vitamin B3 | Vitamin B6 |
| Vitamin B1 | Vitamin B3 | Vitamin B7 |
| Vitamin B1 | Vitamin B3 | Vitamin B8 |
| Vitamin B1 | Vitamin B3 | Vitamin B9 |
| Vitamin B1 | Vitamin B3 | Vitamin B12 |
| Vitamin B1 | Vitamin B3 | Vitamin C |
| Vitamin B1 | Vitamin B3 | Vitamin E |
| Vitamin B1 | Vitamin B3 | Zinc |
| Vitamin B1 | Vitamin B3 | Magnesium |
| Vitamin B1 | Vitamin B3 | Selenium |
| Vitamin B1 | Vitamin B3 | Echinacea |
| Vitamin B1 | Vitamin B3 | Olive leaf |
| Vitamin B1 | Vitamin B3 | Wild indigo |
| Vitamin B1 | Vitamin B3 | Goldenseal |

TABLE 3-continued

Three Ingredient Combinations

| First Ingredient | Second Ingredient | Third Ingredient |
|---|---|---|
| Vitamin B1 | Vitamin B3 | Fenugreek |
| Vitamin B1 | Vitamin B3 | Mullein |
| Vitamin B1 | Vitamin B3 | Phenol |
| Vitamin B1 | Vitamin B3 | Camphor |
| Vitamin B1 | Vitamin B3 | Pectin |
| Vitamin B1 | Vitamin B3 | Eucalyptus Oil |
| Vitamin B1 | Vitamin B3 | Peppermint Oil |
| Vitamin B1 | Vitamin B3 | Spearmint Oil |
| Vitamin B1 | Vitamin B5 | Vitamin B6 |
| Vitamin B1 | Vitamin B5 | Vitamin B7 |
| Vitamin B1 | Vitamin B5 | Vitamin B8 |
| Vitamin B1 | Vitamin B5 | Vitamin B9 |
| Vitamin B1 | Vitamin B5 | Vitamin B12 |
| Vitamin B1 | Vitamin B5 | Vitamin C |
| Vitamin B1 | Vitamin B5 | Vitamin E |
| Vitamin B1 | Vitamin B5 | Zinc |
| Vitamin B1 | Vitamin B5 | Magnesium |
| Vitamin B1 | Vitamin B5 | Selenium |
| Vitamin B1 | Vitamin B5 | Echinacea |
| Vitamin B1 | Vitamin B5 | Olive leaf |
| Vitamin B1 | Vitamin B5 | Wild indigo |
| Vitamin B1 | Vitamin B5 | Goldenseal |
| Vitamin B1 | Vitamin B5 | Fenugreek |
| Vitamin B1 | Vitamin B5 | Mullein |
| Vitamin B1 | Vitamin B5 | Phenol |
| Vitamin B1 | Vitamin B5 | Camphor |
| Vitamin B1 | Vitamin B5 | Pectin |
| Vitamin B1 | Vitamin B5 | Eucalyptus Oil |
| Vitamin B1 | Vitamin B5 | Peppermint Oil |
| Vitamin B1 | Vitamin B5 | Spearmint Oil |
| Vitamin B1 | Vitamin B6 | Vitamin B7 |
| Vitamin B1 | Vitamin B6 | Vitamin B8 |
| Vitamin B1 | Vitamin B6 | Vitamin B9 |
| Vitamin B1 | Vitamin B6 | Vitamin B12 |
| Vitamin B1 | Vitamin B6 | Vitamin C |
| Vitamin B1 | Vitamin B6 | Vitamin E |
| Vitamin B1 | Vitamin B6 | Zinc |
| Vitamin B1 | Vitamin B6 | Magnesium |
| Vitamin B1 | Vitamin B6 | Selenium |
| Vitamin B1 | Vitamin B6 | Echinacea |
| Vitamin B1 | Vitamin B6 | Olive leaf |
| Vitamin B1 | Vitamin B6 | Wild indigo |
| Vitamin B1 | Vitamin B6 | Goldenseal |
| Vitamin B1 | Vitamin B6 | Fenugreek |
| Vitamin B1 | Vitamin B6 | Mullein |
| Vitamin B1 | Vitamin B6 | Phenol |
| Vitamin B1 | Vitamin B6 | Camphor |
| Vitamin B1 | Vitamin B6 | Pectin |
| Vitamin B1 | Vitamin B6 | Eucalyptus Oil |
| Vitamin B1 | Vitamin B6 | Peppermint Oil |
| Vitamin B1 | Vitamin B6 | Spearmint Oil |
| Vitamin B1 | Vitamin B7 | Vitamin B8 |
| Vitamin B1 | Vitamin B7 | Vitamin B9 |
| Vitamin B1 | Vitamin B7 | Vitamin B12 |
| Vitamin B1 | Vitamin B7 | Vitamin C |
| Vitamin B1 | Vitamin B7 | Vitamin E |
| Vitamin B1 | Vitamin B7 | Zinc |
| Vitamin B1 | Vitamin B7 | Magnesium |
| Vitamin B1 | Vitamin B7 | Selenium |
| Vitamin B1 | Vitamin B7 | Echinacea |
| Vitamin B1 | Vitamin B7 | Olive leaf |
| Vitamin B1 | Vitamin B7 | Wild indigo |
| Vitamin B1 | Vitamin B7 | Goldenseal |
| Vitamin B1 | Vitamin B7 | Fenugreek |
| Vitamin B1 | Vitamin B7 | Mullein |
| Vitamin B1 | Vitamin B7 | Phenol |
| Vitamin B1 | Vitamin B7 | Camphor |
| Vitamin B1 | Vitamin B7 | Pectin |
| Vitamin B1 | Vitamin B7 | Eucalyptus Oil |
| Vitamin B1 | Vitamin B7 | Peppermint Oil |
| Vitamin B1 | Vitamin B7 | Spearmint Oil |
| Vitamin B1 | Vitamin B8 | Vitamin B9 |
| Vitamin B1 | Vitamin B8 | Vitamin B12 |
| Vitamin B1 | Vitamin B8 | Vitamin C |
| Vitamin B1 | Vitamin B8 | Vitamin E |
| Vitamin B1 | Vitamin B8 | Zinc |
| Vitamin B1 | Vitamin B8 | Magnesium |
| Vitamin B1 | Vitamin B8 | Selenium |
| Vitamin B1 | Vitamin B8 | Echinacea |
| Vitamin B1 | Vitamin B8 | Olive leaf |
| Vitamin B1 | Vitamin B8 | Wild indigo |
| Vitamin B1 | Vitamin B8 | Goldenseal |
| Vitamin B1 | Vitamin B8 | Fenugreek |
| Vitamin B1 | Vitamin B8 | Mullein |
| Vitamin B1 | Vitamin B8 | Phenol |
| Vitamin B1 | Vitamin B8 | Camphor |
| Vitamin B1 | Vitamin B8 | Pectin |
| Vitamin B1 | Vitamin B8 | Eucalyptus Oil |
| Vitamin B1 | Vitamin B8 | Peppermint Oil |
| Vitamin B1 | Vitamin B8 | Spearmint Oil |
| Vitamin B1 | Vitamin B9 | Vitamin B12 |
| Vitamin B1 | Vitamin B9 | Vitamin C |
| Vitamin B1 | Vitamin B9 | Vitamin E |
| Vitamin B1 | Vitamin B9 | Zinc |
| Vitamin B1 | Vitamin B9 | Magnesium |
| Vitamin B1 | Vitamin B9 | Selenium |
| Vitamin B1 | Vitamin B9 | Echinacea |
| Vitamin B1 | Vitamin B9 | Olive leaf |
| Vitamin B1 | Vitamin B9 | Wild indigo |
| Vitamin B1 | Vitamin B9 | Goldenseal |
| Vitamin B1 | Vitamin B9 | Fenugreek |
| Vitamin B1 | Vitamin B9 | Mullein |
| Vitamin B1 | Vitamin B9 | Phenol |
| Vitamin B1 | Vitamin B9 | Camphor |
| Vitamin B1 | Vitamin B9 | Pectin |
| Vitamin B1 | Vitamin B9 | Eucalyptus Oil |
| Vitamin B1 | Vitamin B9 | Peppermint Oil |
| Vitamin B1 | Vitamin B9 | Spearmint Oil |
| Vitamin B1 | Vitamin B12 | Vitamin C |
| Vitamin B1 | Vitamin B12 | Vitamin E |
| Vitamin B1 | Vitamin B12 | Zinc |
| Vitamin B1 | Vitamin B12 | Magnesium |
| Vitamin B1 | Vitamin B12 | Selenium |
| Vitamin B1 | Vitamin B12 | Echinacea |
| Vitamin B1 | Vitamin B12 | Olive leaf |
| Vitamin B1 | Vitamin B12 | Wild indigo |
| Vitamin B1 | Vitamin B12 | Goldenseal |
| Vitamin B1 | Vitamin B12 | Fenugreek |
| Vitamin B1 | Vitamin B12 | Mullein |
| Vitamin B1 | Vitamin B12 | Phenol |
| Vitamin B1 | Vitamin B12 | Camphor |
| Vitamin B1 | Vitamin B12 | Pectin |
| Vitamin B1 | Vitamin B12 | Eucalyptus Oil |
| Vitamin B1 | Vitamin B12 | Peppermint Oil |
| Vitamin B1 | Vitamin B12 | Spearmint Oil |
| Vitamin B1 | Vitamin C | Vitamin E |
| Vitamin B1 | Vitamin C | Zinc |
| Vitamin B1 | Vitamin C | Magnesium |
| Vitamin B1 | Vitamin C | Selenium |
| Vitamin B1 | Vitamin C | Echinacea |
| Vitamin B1 | Vitamin C | Olive leaf |
| Vitamin B1 | Vitamin C | Wild indigo |
| Vitamin B1 | Vitamin C | Goldenseal |
| Vitamin B1 | Vitamin C | Fenugreek |
| Vitamin B1 | Vitamin C | Mullein |
| Vitamin B1 | Vitamin C | Phenol |
| Vitamin B1 | Vitamin C | Camphor |
| Vitamin B1 | Vitamin C | Pectin |
| Vitamin B1 | Vitamin C | Eucalyptus Oil |
| Vitamin B1 | Vitamin C | Peppermint Oil |
| Vitamin B1 | Vitamin C | Spearmint Oil |
| Vitamin B1 | Vitamin E | Zinc |
| Vitamin B1 | Vitamin E | Magnesium |
| Vitamin B1 | Vitamin E | Selenium |
| Vitamin B1 | Vitamin E | Echinacea |
| Vitamin B1 | Vitamin E | Olive leaf |
| Vitamin B1 | Vitamin E | Wild indigo |
| Vitamin B1 | Vitamin E | Goldenseal |
| Vitamin B1 | Vitamin E | Fenugreek |
| Vitamin B1 | Vitamin E | Mullein |
| Vitamin B1 | Vitamin E | Phenol |
| Vitamin B1 | Vitamin E | Camphor |

TABLE 3-continued

Three Ingredient Combinations

| First Ingredient | Second Ingredient | Third Ingredient |
|---|---|---|
| Vitamin B1 | Vitamin E | Pectin |
| Vitamin B1 | Vitamin E | Eucalyptus Oil |
| Vitamin B1 | Vitamin E | Peppermint Oil |
| Vitamin B1 | Vitamin E | Spearmint Oil |
| Vitamin B1 | Zinc | Magnesium |
| Vitamin B1 | Zinc | Selenium |
| Vitamin B1 | Zinc | Echinacea |
| Vitamin B1 | Zinc | Olive leaf |
| Vitamin B1 | Zinc | Wild indigo |
| Vitamin B1 | Zinc | Goldenseal |
| Vitamin B1 | Zinc | Fenugreek |
| Vitamin B1 | Zinc | Mullein |
| Vitamin B1 | Zinc | Phenol |
| Vitamin B1 | Zinc | Camphor |
| Vitamin B1 | Zinc | Pectin |
| Vitamin B1 | Zinc | Eucalyptus Oil |
| Vitamin B1 | Zinc | Peppermint Oil |
| Vitamin B1 | Zinc | Spearmint Oil |
| Vitamin B1 | Magnesium | Selenium |
| Vitamin B1 | Magnesium | Echinacea |
| Vitamin B1 | Magnesium | Olive leaf |
| Vitamin B1 | Magnesium | Wild indigo |
| Vitamin B1 | Magnesium | Goldenseal |
| Vitamin B1 | Magnesium | Fenugreek |
| Vitamin B1 | Magnesium | Mullein |
| Vitamin B1 | Magnesium | Phenol |
| Vitamin B1 | Magnesium | Camphor |
| Vitamin B1 | Magnesium | Pectin |
| Vitamin B1 | Magnesium | Eucalyptus Oil |
| Vitamin B1 | Magnesium | Peppermint Oil |
| Vitamin B1 | Magnesium | Spearmint Oil |
| Vitamin B1 | Selenium | Echinacea |
| Vitamin B1 | Selenium | Olive leaf |
| Vitamin B1 | Selenium | Wild indigo |
| Vitamin B1 | Selenium | Goldenseal |
| Vitamin B1 | Selenium | Fenugreek |
| Vitamin B1 | Selenium | Mullein |
| Vitamin B1 | Selenium | Phenol |
| Vitamin B1 | Selenium | Camphor |
| Vitamin B1 | Selenium | Pectin |
| Vitamin B1 | Selenium | Eucalyptus Oil |
| Vitamin B1 | Selenium | Peppermint Oil |
| Vitamin B1 | Selenium | Spearmint Oil |
| Vitamin B1 | Echinacea | Olive leaf |
| Vitamin B1 | Echinacea | Wild indigo |
| Vitamin B1 | Echinacea | Goldenseal |
| Vitamin B1 | Echinacea | Fenugreek |
| Vitamin B1 | Echinacea | Mullein |
| Vitamin B1 | Echinacea | Phenol |
| Vitamin B1 | Echinacea | Camphor |
| Vitamin B1 | Echinacea | Pectin |
| Vitamin B1 | Echinacea | Eucalyptus Oil |
| Vitamin B1 | Echinacea | Peppermint Oil |
| Vitamin B1 | Echinacea | Spearmint Oil |
| Vitamin B1 | Olive leaf | Wild indigo |
| Vitamin B1 | Olive leaf | Goldenseal |
| Vitamin B1 | Olive leaf | Fenugreek |
| Vitamin B1 | Olive leaf | Mullein |
| Vitamin B1 | Olive leaf | Phenol |
| Vitamin B1 | Olive leaf | Camphor |
| Vitamin B1 | Olive leaf | Pectin |
| Vitamin B1 | Olive leaf | Eucalyptus Oil |
| Vitamin B1 | Olive leaf | Peppermint Oil |
| Vitamin B1 | Olive leaf | Spearmint Oil |
| Vitamin B1 | Wild indigo | Goldenseal |
| Vitamin B1 | Wild indigo | Fenugreek |
| Vitamin B1 | Wild indigo | Mullein |
| Vitamin B1 | Wild indigo | Phenol |
| Vitamin B1 | Wild indigo | Camphor |
| Vitamin B1 | Wild indigo | Pectin |
| Vitamin B1 | Wild indigo | Eucalyptus Oil |
| Vitamin B1 | Wild indigo | Peppermint Oil |
| Vitamin B1 | Wild indigo | Spearmint Oil |
| Vitamin B1 | Goldenseal | Fenugreek |
| Vitamin B1 | Goldenseal | Mullein |
| Vitamin B1 | Goldenseal | Phenol |
| Vitamin B1 | Goldenseal | Camphor |
| Vitamin B1 | Goldenseal | Pectin |
| Vitamin B1 | Goldenseal | Eucalyptus Oil |
| Vitamin B1 | Goldenseal | Peppermint Oil |
| Vitamin B1 | Goldenseal | Spearmint Oil |
| Vitamin B1 | Fenugreek | Mullein |
| Vitamin B1 | Fenugreek | Phenol |
| Vitamin B1 | Fenugreek | Camphor |
| Vitamin B1 | Fenugreek | Pectin |
| Vitamin B1 | Fenugreek | Eucalyptus Oil |
| Vitamin B1 | Fenugreek | Peppermint Oil |
| Vitamin B1 | Fenugreek | Spearmint Oil |
| Vitamin B1 | Mullein | Phenol |
| Vitamin B1 | Mullein | Camphor |
| Vitamin B1 | Mullein | Pectin |
| Vitamin B1 | Mullein | Eucalyptus Oil |
| Vitamin B1 | Mullein | Peppermint Oil |
| Vitamin B1 | Mullein | Spearmint Oil |
| Vitamin B1 | Phenol | Camphor |
| Vitamin B1 | Phenol | Pectin |
| Vitamin B1 | Phenol | Eucalyptus Oil |
| Vitamin B1 | Phenol | Peppermint Oil |
| Vitamin B1 | Phenol | Spearmint Oil |
| Vitamin B1 | Camphor | Pectin |
| Vitamin B1 | Camphor | Eucalyptus Oil |
| Vitamin B1 | Camphor | Peppermint Oil |
| Vitamin B1 | Camphor | Spearmint Oil |
| Vitamin B1 | Pectin | Eucalyptus Oil |
| Vitamin B1 | Pectin | Peppermint Oil |
| Vitamin B1 | Pectin | Spearmint Oil |
| Vitamin B1 | Eucalyptus Oil | Peppermint Oil |
| Vitamin B1 | Eucalyptus Oil | Spearmint Oil |
| Vitamin B1 | Peppermint Oil | Spearmint Oil |
| Vitamin B2 | Vitamin B3 | Vitamin B5 |
| Vitamin B2 | Vitamin B3 | Vitamin B6 |
| Vitamin B2 | Vitamin B3 | Vitamin B7 |
| Vitamin B2 | Vitamin B3 | Vitamin B8 |
| Vitamin B2 | Vitamin B3 | Vitamin B9 |
| Vitamin B2 | Vitamin B3 | Vitamin B12 |
| Vitamin B2 | Vitamin B3 | Vitamin C |
| Vitamin B2 | Vitamin B3 | Vitamin E |
| Vitamin B2 | Vitamin B3 | Zinc |
| Vitamin B2 | Vitamin B3 | Magnesium |
| Vitamin B2 | Vitamin B3 | Selenium |
| Vitamin B2 | Vitamin B3 | Echinacea |
| Vitamin B2 | Vitamin B3 | Olive leaf |
| Vitamin B2 | Vitamin B3 | Wild indigo |
| Vitamin B2 | Vitamin B3 | Goldenseal |
| Vitamin B2 | Vitamin B3 | Fenugreek |
| Vitamin B2 | Vitamin B3 | Mullein |
| Vitamin B2 | Vitamin B3 | Phenol |
| Vitamin B2 | Vitamin B3 | Camphor |
| Vitamin B2 | Vitamin B3 | Pectin |
| Vitamin B2 | Vitamin B3 | Eucalyptus Oil |
| Vitamin B2 | Vitamin B3 | Peppermint Oil |
| Vitamin B2 | Vitamin B3 | Spearmint Oil |
| Vitamin B2 | Vitamin B5 | Vitamin B6 |
| Vitamin B2 | Vitamin B5 | Vitamin B7 |
| Vitamin B2 | Vitamin B5 | Vitamin B8 |
| Vitamin B2 | Vitamin B5 | Vitamin B9 |
| Vitamin B2 | Vitamin B5 | Vitamin B12 |
| Vitamin B2 | Vitamin B5 | Vitamin C |
| Vitamin B2 | Vitamin B5 | Vitamin E |
| Vitamin B2 | Vitamin B5 | Zinc |
| Vitamin B2 | Vitamin B5 | Magnesium |
| Vitamin B2 | Vitamin B5 | Selenium |
| Vitamin B2 | Vitamin B5 | Echinacea |
| Vitamin B2 | Vitamin B5 | Olive leaf |
| Vitamin B2 | Vitamin B5 | Wild indigo |
| Vitamin B2 | Vitamin B5 | Goldenseal |
| Vitamin B2 | Vitamin B5 | Fenugreek |
| Vitamin B2 | Vitamin B5 | Mullein |
| Vitamin B2 | Vitamin B5 | Phenol |
| Vitamin B2 | Vitamin B5 | Camphor |
| Vitamin B2 | Vitamin B5 | Pectin |
| Vitamin B2 | Vitamin B5 | Eucalyptus Oil |

TABLE 3-continued

Three Ingredient Combinations

| First Ingredient | Second Ingredient | Third Ingredient |
|---|---|---|
| Vitamin B2 | Vitamin B5 | Peppermint Oil |
| Vitamin B2 | Vitamin B5 | Spearmint Oil |
| Vitamin B2 | Vitamin B6 | Vitamin B7 |
| Vitamin B2 | Vitamin B6 | Vitamin B8 |
| Vitamin B2 | Vitamin B6 | Vitamin B9 |
| Vitamin B2 | Vitamin B6 | Vitamin B12 |
| Vitamin B2 | Vitamin B6 | Vitamin C |
| Vitamin B2 | Vitamin B6 | Vitamin E |
| Vitamin B2 | Vitamin B6 | Zinc |
| Vitamin B2 | Vitamin B6 | Magnesium |
| Vitamin B2 | Vitamin B6 | Selenium |
| Vitamin B2 | Vitamin B6 | Echinacea |
| Vitamin B2 | Vitamin B6 | Olive leaf |
| Vitamin B2 | Vitamin B6 | Wild indigo |
| Vitamin B2 | Vitamin B6 | Goldenseal |
| Vitamin B2 | Vitamin B6 | Fenugreek |
| Vitamin B2 | Vitamin B6 | Mullein |
| Vitamin B2 | Vitamin B6 | Phenol |
| Vitamin B2 | Vitamin B6 | Camphor |
| Vitamin B2 | Vitamin B6 | Pectin |
| Vitamin B2 | Vitamin B6 | Eucalyptus Oil |
| Vitamin B2 | Vitamin B6 | Peppermint Oil |
| Vitamin B2 | Vitamin B6 | Spearmint Oil |
| Vitamin B2 | Vitamin B7 | Vitamin B8 |
| Vitamin B2 | Vitamin B7 | Vitamin B9 |
| Vitamin B2 | Vitamin B7 | Vitamin B12 |
| Vitamin B2 | Vitamin B7 | Vitamin C |
| Vitamin B2 | Vitamin B7 | Vitamin E |
| Vitamin B2 | Vitamin B7 | Zinc |
| Vitamin B2 | Vitamin B7 | Magnesium |
| Vitamin B2 | Vitamin B7 | Selenium |
| Vitamin B2 | Vitamin B7 | Echinacea |
| Vitamin B2 | Vitamin B7 | Olive leaf |
| Vitamin B2 | Vitamin B7 | Wild indigo |
| Vitamin B2 | Vitamin B7 | Goldenseal |
| Vitamin B2 | Vitamin B7 | Fenugreek |
| Vitamin B2 | Vitamin B7 | Mullein |
| Vitamin B2 | Vitamin B7 | Phenol |
| Vitamin B2 | Vitamin B7 | Camphor |
| Vitamin B2 | Vitamin B7 | Pectin |
| Vitamin B2 | Vitamin B7 | Eucalyptus Oil |
| Vitamin B2 | Vitamin B7 | Peppermint Oil |
| Vitamin B2 | Vitamin B7 | Spearmint Oil |
| Vitamin B2 | Vitamin B8 | Vitamin B9 |
| Vitamin B2 | Vitamin B8 | Vitamin B12 |
| Vitamin B2 | Vitamin B8 | Vitamin C |
| Vitamin B2 | Vitamin B8 | Vitamin E |
| Vitamin B2 | Vitamin B8 | Zinc |
| Vitamin B2 | Vitamin B8 | Magnesium |
| Vitamin B2 | Vitamin B8 | Selenium |
| Vitamin B2 | Vitamin B8 | Echinacea |
| Vitamin B2 | Vitamin B8 | Olive leaf |
| Vitamin B2 | Vitamin B8 | Wild indigo |
| Vitamin B2 | Vitamin B8 | Goldenseal |
| Vitamin B2 | Vitamin B8 | Fenugreek |
| Vitamin B2 | Vitamin B8 | Mullein |
| Vitamin B2 | Vitamin B8 | Phenol |
| Vitamin B2 | Vitamin B8 | Camphor |
| Vitamin B2 | Vitamin B8 | Pectin |
| Vitamin B2 | Vitamin B8 | Eucalyptus Oil |
| Vitamin B2 | Vitamin B8 | Peppermint Oil |
| Vitamin B2 | Vitamin B8 | Spearmint Oil |
| Vitamin B2 | Vitamin B9 | Vitamin B12 |
| Vitamin B2 | Vitamin B9 | Vitamin C |
| Vitamin B2 | Vitamin B9 | Vitamin E |
| Vitamin B2 | Vitamin B9 | Zinc |
| Vitamin B2 | Vitamin B9 | Magnesium |
| Vitamin B2 | Vitamin B9 | Selenium |
| Vitamin B2 | Vitamin B9 | Echinacea |
| Vitamin B2 | Vitamin B9 | Olive leaf |
| Vitamin B2 | Vitamin B9 | Wild indigo |
| Vitamin B2 | Vitamin B9 | Goldenseal |
| Vitamin B2 | Vitamin B9 | Fenugreek |
| Vitamin B2 | Vitamin B9 | Mullein |
| Vitamin B2 | Vitamin B9 | Phenol |
| Vitamin B2 | Vitamin B9 | Camphor |
| Vitamin B2 | Vitamin B9 | Pectin |
| Vitamin B2 | Vitamin B9 | Eucalyptus Oil |
| Vitamin B2 | Vitamin B9 | Peppermint Oil |
| Vitamin B2 | Vitamin B9 | Spearmint Oil |
| Vitamin B2 | Vitamin B12 | Vitamin C |
| Vitamin B2 | Vitamin B12 | Vitamin E |
| Vitamin B2 | Vitamin B12 | Zinc |
| Vitamin B2 | Vitamin B12 | Magnesium |
| Vitamin B2 | Vitamin B12 | Selenium |
| Vitamin B2 | Vitamin B12 | Echinacea |
| Vitamin B2 | Vitamin B12 | Olive leaf |
| Vitamin B2 | Vitamin B12 | Wild indigo |
| Vitamin B2 | Vitamin B12 | Goldenseal |
| Vitamin B2 | Vitamin B12 | Fenugreek |
| Vitamin B2 | Vitamin B12 | Mullein |
| Vitamin B2 | Vitamin B12 | Phenol |
| Vitamin B2 | Vitamin B12 | Camphor |
| Vitamin B2 | Vitamin B12 | Pectin |
| Vitamin B2 | Vitamin B12 | Eucalyptus Oil |
| Vitamin B2 | Vitamin B12 | Peppermint Oil |
| Vitamin B2 | Vitamin B12 | Spearmint Oil |
| Vitamin B2 | Vitamin C | Vitamin E |
| Vitamin B2 | Vitamin C | Zinc |
| Vitamin B2 | Vitamin C | Magnesium |
| Vitamin B2 | Vitamin C | Selenium |
| Vitamin B2 | Vitamin C | Echinacea |
| Vitamin B2 | Vitamin C | Olive leaf |
| Vitamin B2 | Vitamin C | Wild indigo |
| Vitamin B2 | Vitamin C | Goldenseal |
| Vitamin B2 | Vitamin C | Fenugreek |
| Vitamin B2 | Vitamin C | Mullein |
| Vitamin B2 | Vitamin C | Phenol |
| Vitamin B2 | Vitamin C | Camphor |
| Vitamin B2 | Vitamin C | Pectin |
| Vitamin B2 | Vitamin C | Eucalyptus Oil |
| Vitamin B2 | Vitamin C | Peppermint Oil |
| Vitamin B2 | Vitamin C | Spearmint Oil |
| Vitamin B2 | Vitamin E | Zinc |
| Vitamin B2 | Vitamin E | Magnesium |
| Vitamin B2 | Vitamin E | Selenium |
| Vitamin B2 | Vitamin E | Echinacea |
| Vitamin B2 | Vitamin E | Olive leaf |
| Vitamin B2 | Vitamin E | Wild indigo |
| Vitamin B2 | Vitamin E | Goldenseal |
| Vitamin B2 | Vitamin E | Fenugreek |
| Vitamin B2 | Vitamin E | Mullein |
| Vitamin B2 | Vitamin E | Phenol |
| Vitamin B2 | Vitamin E | Camphor |
| Vitamin B2 | Vitamin E | Pectin |
| Vitamin B2 | Vitamin E | Eucalyptus Oil |
| Vitamin B2 | Vitamin E | Peppermint Oil |
| Vitamin B2 | Vitamin E | Spearmint Oil |
| Vitamin B2 | Zinc | Magnesium |
| Vitamin B2 | Zinc | Selenium |
| Vitamin B2 | Zinc | Echinacea |
| Vitamin B2 | Zinc | Olive leaf |
| Vitamin B2 | Zinc | Wild indigo |
| Vitamin B2 | Zinc | Goldenseal |
| Vitamin B2 | Zinc | Fenugreek |
| Vitamin B2 | Zinc | Mullein |
| Vitamin B2 | Zinc | Phenol |
| Vitamin B2 | Zinc | Camphor |
| Vitamin B2 | Zinc | Pectin |
| Vitamin B2 | Zinc | Eucalyptus Oil |
| Vitamin B2 | Zinc | Peppermint Oil |
| Vitamin B2 | Zinc | Spearmint Oil |
| Vitamin B2 | Magnesium | Selenium |
| Vitamin B2 | Magnesium | Echinacea |
| Vitamin B2 | Magnesium | Olive leaf |
| Vitamin B2 | Magnesium | Wild indigo |
| Vitamin B2 | Magnesium | Goldenseal |
| Vitamin B2 | Magnesium | Fenugreek |
| Vitamin B2 | Magnesium | Mullein |
| Vitamin B2 | Magnesium | Phenol |
| Vitamin B2 | Magnesium | Camphor |
| Vitamin B2 | Magnesium | Pectin |

TABLE 3-continued

Three Ingredient Combinations

| First Ingredient | Second Ingredient | Third Ingredient |
|---|---|---|
| Vitamin B2 | Magnesium | Eucalyptus Oil |
| Vitamin B2 | Magnesium | Peppermint Oil |
| Vitamin B2 | Magnesium | Spearmint Oil |
| Vitamin B2 | Selenium | Echinacea |
| Vitamin B2 | Selenium | Olive leaf |
| Vitamin B2 | Selenium | Wild indigo |
| Vitamin B2 | Selenium | Goldenseal |
| Vitamin B2 | Selenium | Fenugreek |
| Vitamin B2 | Selenium | Mullein |
| Vitamin B2 | Selenium | Phenol |
| Vitamin B2 | Selenium | Camphor |
| Vitamin B2 | Selenium | Pectin |
| Vitamin B2 | Selenium | Eucalyptus Oil |
| Vitamin B2 | Selenium | Peppermint Oil |
| Vitamin B2 | Selenium | Spearmint Oil |
| Vitamin B2 | Echinacea | Olive leaf |
| Vitamin B2 | Echinacea | Wild indigo |
| Vitamin B2 | Echinacea | Goldenseal |
| Vitamin B2 | Echinacea | Fenugreek |
| Vitamin B2 | Echinacea | Mullein |
| Vitamin B2 | Echinacea | Phenol |
| Vitamin B2 | Echinacea | Camphor |
| Vitamin B2 | Echinacea | Pectin |
| Vitamin B2 | Echinacea | Eucalyptus Oil |
| Vitamin B2 | Echinacea | Peppermint Oil |
| Vitamin B2 | Echinacea | Spearmint Oil |
| Vitamin B2 | Olive leaf | Wild indigo |
| Vitamin B2 | Olive leaf | Goldenseal |
| Vitamin B2 | Olive leaf | Fenugreek |
| Vitamin B2 | Olive leaf | Mullein |
| Vitamin B2 | Olive leaf | Phenol |
| Vitamin B2 | Olive leaf | Camphor |
| Vitamin B2 | Olive leaf | Pectin |
| Vitamin B2 | Olive leaf | Eucalyptus Oil |
| Vitamin B2 | Olive leaf | Peppermint Oil |
| Vitamin B2 | Olive leaf | Spearmint Oil |
| Vitamin B2 | Wild indigo | Goldenseal |
| Vitamin B2 | Wild indigo | Fenugreek |
| Vitamin B2 | Wild indigo | Mullein |
| Vitamin B2 | Wild indigo | Phenol |
| Vitamin B2 | Wild indigo | Camphor |
| Vitamin B2 | Wild indigo | Pectin |
| Vitamin B2 | Wild indigo | Eucalyptus Oil |
| Vitamin B2 | Wild indigo | Peppermint Oil |
| Vitamin B2 | Wild indigo | Spearmint Oil |
| Vitamin B2 | Goldenseal | Fenugreek |
| Vitamin B2 | Goldenseal | Mullein |
| Vitamin B2 | Goldenseal | Phenol |
| Vitamin B2 | Goldenseal | Camphor |
| Vitamin B2 | Goldenseal | Pectin |
| Vitamin B2 | Goldenseal | Eucalyptus Oil |
| Vitamin B2 | Goldenseal | Peppermint Oil |
| Vitamin B2 | Goldenseal | Spearmint Oil |
| Vitamin B2 | Fenugreek | Mullein |
| Vitamin B2 | Fenugreek | Phenol |
| Vitamin B2 | Fenugreek | Camphor |
| Vitamin B2 | Fenugreek | Pectin |
| Vitamin B2 | Fenugreek | Eucalyptus Oil |
| Vitamin B2 | Fenugreek | Peppermint Oil |
| Vitamin B2 | Fenugreek | Spearmint Oil |
| Vitamin B2 | Mullein | Phenol |
| Vitamin B2 | Mullein | Camphor |
| Vitamin B2 | Mullein | Pectin |
| Vitamin B2 | Mullein | Eucalyptus Oil |
| Vitamin B2 | Mullein | Peppermint Oil |
| Vitamin B2 | Mullein | Spearmint Oil |
| Vitamin B2 | Phenol | Camphor |
| Vitamin B2 | Phenol | Pectin |
| Vitamin B2 | Phenol | Eucalyptus Oil |
| Vitamin B2 | Phenol | Peppermint Oil |
| Vitamin B2 | Phenol | Spearmint Oil |
| Vitamin B2 | Camphor | Pectin |
| Vitamin B2 | Camphor | Eucalyptus Oil |
| Vitamin B2 | Camphor | Peppermint Oil |
| Vitamin B2 | Camphor | Spearmint Oil |
| Vitamin B2 | Pectin | Eucalyptus Oil |
| Vitamin B2 | Pectin | Peppermint Oil |
| Vitamin B2 | Pectin | Spearmint Oil |
| Vitamin B2 | Eucalyptus Oil | Peppermint Oil |
| Vitamin B2 | Eucalyptus Oil | Spearmint Oil |
| Vitamin B2 | Peppermint Oil | Spearmint Oil |
| Vitamin B3 | Vitamin B5 | Vitamin B6 |
| Vitamin B3 | Vitamin B5 | Vitamin B7 |
| Vitamin B3 | Vitamin B5 | Vitamin B8 |
| Vitamin B3 | Vitamin B5 | Vitamin B9 |
| Vitamin B3 | Vitamin B5 | Vitamin B12 |
| Vitamin B3 | Vitamin B5 | Vitamin C |
| Vitamin B3 | Vitamin B5 | Vitamin E |
| Vitamin B3 | Vitamin B5 | Zinc |
| Vitamin B3 | Vitamin B5 | Magnesium |
| Vitamin B3 | Vitamin B5 | Selenium |
| Vitamin B3 | Vitamin B5 | Echinacea |
| Vitamin B3 | Vitamin B5 | Olive leaf |
| Vitamin B3 | Vitamin B5 | Wild indigo |
| Vitamin B3 | Vitamin B5 | Goldenseal |
| Vitamin B3 | Vitamin B5 | Fenugreek |
| Vitamin B3 | Vitamin B5 | Mullein |
| Vitamin B3 | Vitamin B5 | Phenol |
| Vitamin B3 | Vitamin B5 | Camphor |
| Vitamin B3 | Vitamin B5 | Pectin |
| Vitamin B3 | Vitamin B5 | Eucalyptus Oil |
| Vitamin B3 | Vitamin B5 | Peppermint Oil |
| Vitamin B3 | Vitamin B5 | Spearmint Oil |
| Vitamin B3 | Vitamin B6 | Vitamin B7 |
| Vitamin B3 | Vitamin B6 | Vitamin B8 |
| Vitamin B3 | Vitamin B6 | Vitamin B9 |
| Vitamin B3 | Vitamin B6 | Vitamin B12 |
| Vitamin B3 | Vitamin B6 | Vitamin C |
| Vitamin B3 | Vitamin B6 | Vitamin E |
| Vitamin B3 | Vitamin B6 | Zinc |
| Vitamin B3 | Vitamin B6 | Magnesium |
| Vitamin B3 | Vitamin B6 | Selenium |
| Vitamin B3 | Vitamin B6 | Echinacea |
| Vitamin B3 | Vitamin B6 | Olive leaf |
| Vitamin B3 | Vitamin B6 | Wild indigo |
| Vitamin B3 | Vitamin B6 | Goldenseal |
| Vitamin B3 | Vitamin B6 | Fenugreek |
| Vitamin B3 | Vitamin B6 | Mullein |
| Vitamin B3 | Vitamin B6 | Phenol |
| Vitamin B3 | Vitamin B6 | Camphor |
| Vitamin B3 | Vitamin B6 | Pectin |
| Vitamin B3 | Vitamin B6 | Eucalyptus Oil |
| Vitamin B3 | Vitamin B6 | Peppermint Oil |
| Vitamin B3 | Vitamin B6 | Spearmint Oil |
| Vitamin B3 | Vitamin B7 | Vitamin B8 |
| Vitamin B3 | Vitamin B7 | Vitamin B9 |
| Vitamin B3 | Vitamin B7 | Vitamin B12 |
| Vitamin B3 | Vitamin B7 | Vitamin C |
| Vitamin B3 | Vitamin B7 | Vitamin E |
| Vitamin B3 | Vitamin B7 | Zinc |
| Vitamin B3 | Vitamin B7 | Magnesium |
| Vitamin B3 | Vitamin B7 | Selenium |
| Vitamin B3 | Vitamin B7 | Echinacea |
| Vitamin B3 | Vitamin B7 | Olive leaf |
| Vitamin B3 | Vitamin B7 | Wild indigo |
| Vitamin B3 | Vitamin B7 | Goldenseal |
| Vitamin B3 | Vitamin B7 | Fenugreek |
| Vitamin B3 | Vitamin B7 | Mullein |
| Vitamin B3 | Vitamin B7 | Phenol |
| Vitamin B3 | Vitamin B7 | Camphor |
| Vitamin B3 | Vitamin B7 | Pectin |
| Vitamin B3 | Vitamin B7 | Eucalyptus Oil |
| Vitamin B3 | Vitamin B7 | Peppermint Oil |
| Vitamin B3 | Vitamin B7 | Spearmint Oil |
| Vitamin B3 | Vitamin B8 | Vitamin B9 |
| Vitamin B3 | Vitamin B8 | Vitamin B12 |
| Vitamin B3 | Vitamin B8 | Vitamin C |
| Vitamin B3 | Vitamin B8 | Vitamin E |
| Vitamin B3 | Vitamin B8 | Zinc |
| Vitamin B3 | Vitamin B8 | Magnesium |
| Vitamin B3 | Vitamin B8 | Selenium |
| Vitamin B3 | Vitamin B8 | Echinacea |

TABLE 3-continued

Three Ingredient Combinations

| First Ingredient | Second Ingredient | Third Ingredient |
|---|---|---|
| Vitamin B3 | Vitamin B8 | Olive leaf |
| Vitamin B3 | Vitamin B8 | Wild indigo |
| Vitamin B3 | Vitamin B8 | Goldenseal |
| Vitamin B3 | Vitamin B8 | Fenugreek |
| Vitamin B3 | Vitamin B8 | Mullein |
| Vitamin B3 | Vitamin B8 | Phenol |
| Vitamin B3 | Vitamin B8 | Camphor |
| Vitamin B3 | Vitamin B8 | Pectin |
| Vitamin B3 | Vitamin B8 | Eucalyptus Oil |
| Vitamin B3 | Vitamin B8 | Peppermint Oil |
| Vitamin B3 | Vitamin B8 | Spearmint Oil |
| Vitamin B3 | Vitamin B9 | Vitamin B12 |
| Vitamin B3 | Vitamin B9 | Vitamin C |
| Vitamin B3 | Vitamin B9 | Vitamin E |
| Vitamin B3 | Vitamin B9 | Zinc |
| Vitamin B3 | Vitamin B9 | Magnesium |
| Vitamin B3 | Vitamin B9 | Selenium |
| Vitamin B3 | Vitamin B9 | Echinacea |
| Vitamin B3 | Vitamin B9 | Olive leaf |
| Vitamin B3 | Vitamin B9 | Wild indigo |
| Vitamin B3 | Vitamin B9 | Goldenseal |
| Vitamin B3 | Vitamin B9 | Fenugreek |
| Vitamin B3 | Vitamin B9 | Mullein |
| Vitamin B3 | Vitamin B9 | Phenol |
| Vitamin B3 | Vitamin B9 | Camphor |
| Vitamin B3 | Vitamin B9 | Pectin |
| Vitamin B3 | Vitamin B9 | Eucalyptus Oil |
| Vitamin B3 | Vitamin B9 | Peppermint Oil |
| Vitamin B3 | Vitamin B9 | Spearmint Oil |
| Vitamin B3 | Vitamin B12 | Vitamin C |
| Vitamin B3 | Vitamin B12 | Vitamin E |
| Vitamin B3 | Vitamin B12 | Zinc |
| Vitamin B3 | Vitamin B12 | Magnesium |
| Vitamin B3 | Vitamin B12 | Selenium |
| Vitamin B3 | Vitamin B12 | Echinacea |
| Vitamin B3 | Vitamin B12 | Olive leaf |
| Vitamin B3 | Vitamin B12 | Wild indigo |
| Vitamin B3 | Vitamin B12 | Goldenseal |
| Vitamin B3 | Vitamin B12 | Fenugreek |
| Vitamin B3 | Vitamin B12 | Mullein |
| Vitamin B3 | Vitamin B12 | Phenol |
| Vitamin B3 | Vitamin B12 | Camphor |
| Vitamin B3 | Vitamin B12 | Pectin |
| Vitamin B3 | Vitamin B12 | Eucalyptus Oil |
| Vitamin B3 | Vitamin B12 | Peppermint Oil |
| Vitamin B3 | Vitamin B12 | Spearmint Oil |
| Vitamin B3 | Vitamin C | Vitamin E |
| Vitamin B3 | Vitamin C | Zinc |
| Vitamin B3 | Vitamin C | Magnesium |
| Vitamin B3 | Vitamin C | Selenium |
| Vitamin B3 | Vitamin C | Echinacea |
| Vitamin B3 | Vitamin C | Olive leaf |
| Vitamin B3 | Vitamin C | Wild indigo |
| Vitamin B3 | Vitamin C | Goldenseal |
| Vitamin B3 | Vitamin C | Fenugreek |
| Vitamin B3 | Vitamin C | Mullein |
| Vitamin B3 | Vitamin C | Phenol |
| Vitamin B3 | Vitamin C | Camphor |
| Vitamin B3 | Vitamin C | Pectin |
| Vitamin B3 | Vitamin C | Eucalyptus Oil |
| Vitamin B3 | Vitamin C | Peppermint Oil |
| Vitamin B3 | Vitamin C | Spearmint Oil |
| Vitamin B3 | Vitamin E | Zinc |
| Vitamin B3 | Vitamin E | Magnesium |
| Vitamin B3 | Vitamin E | Selenium |
| Vitamin B3 | Vitamin E | Echinacea |
| Vitamin B3 | Vitamin E | Olive leaf |
| Vitamin B3 | Vitamin E | Wild indigo |
| Vitamin B3 | Vitamin E | Goldenseal |
| Vitamin B3 | Vitamin E | Fenugreek |
| Vitamin B3 | Vitamin E | Mullein |
| Vitamin B3 | Vitamin E | Phenol |
| Vitamin B3 | Vitamin E | Camphor |
| Vitamin B3 | Vitamin E | Pectin |
| Vitamin B3 | Vitamin E | Eucalyptus Oil |
| Vitamin B3 | Vitamin E | Peppermint Oil |
| Vitamin B3 | Vitamin E | Spearmint Oil |
| Vitamin B3 | Zinc | Magnesium |
| Vitamin B3 | Zinc | Selenium |
| Vitamin B3 | Zinc | Echinacea |
| Vitamin B3 | Zinc | Olive leaf |
| Vitamin B3 | Zinc | Wild indigo |
| Vitamin B3 | Zinc | Goldenseal |
| Vitamin B3 | Zinc | Fenugreek |
| Vitamin B3 | Zinc | Mullein |
| Vitamin B3 | Zinc | Phenol |
| Vitamin B3 | Zinc | Camphor |
| Vitamin B3 | Zinc | Pectin |
| Vitamin B3 | Zinc | Eucalyptus Oil |
| Vitamin B3 | Zinc | Peppermint Oil |
| Vitamin B3 | Zinc | Spearmint Oil |
| Vitamin B3 | Magnesium | Selenium |
| Vitamin B3 | Magnesium | Echinacea |
| Vitamin B3 | Magnesium | Olive leaf |
| Vitamin B3 | Magnesium | Wild indigo |
| Vitamin B3 | Magnesium | Goldenseal |
| Vitamin B3 | Magnesium | Fenugreek |
| Vitamin B3 | Magnesium | Mullein |
| Vitamin B3 | Magnesium | Phenol |
| Vitamin B3 | Magnesium | Camphor |
| Vitamin B3 | Magnesium | Pectin |
| Vitamin B3 | Magnesium | Eucalyptus Oil |
| Vitamin B3 | Magnesium | Peppermint Oil |
| Vitamin B3 | Magnesium | Spearmint Oil |
| Vitamin B3 | Selenium | Echinacea |
| Vitamin B3 | Selenium | Olive leaf |
| Vitamin B3 | Selenium | Wild indigo |
| Vitamin B3 | Selenium | Goldenseal |
| Vitamin B3 | Selenium | Fenugreek |
| Vitamin B3 | Selenium | Mullein |
| Vitamin B3 | Selenium | Phenol |
| Vitamin B3 | Selenium | Camphor |
| Vitamin B3 | Selenium | Pectin |
| Vitamin B3 | Selenium | Eucalyptus Oil |
| Vitamin B3 | Selenium | Peppermint Oil |
| Vitamin B3 | Selenium | Spearmint Oil |
| Vitamin B3 | Echinacea | Olive leaf |
| Vitamin B3 | Echinacea | Wild indigo |
| Vitamin B3 | Echinacea | Goldenseal |
| Vitamin B3 | Echinacea | Fenugreek |
| Vitamin B3 | Echinacea | Mullein |
| Vitamin B3 | Echinacea | Phenol |
| Vitamin B3 | Echinacea | Camphor |
| Vitamin B3 | Echinacea | Pectin |
| Vitamin B3 | Echinacea | Eucalyptus Oil |
| Vitamin B3 | Echinacea | Peppermint Oil |
| Vitamin B3 | Echinacea | Spearmint Oil |
| Vitamin B3 | Olive leaf | Wild indigo |
| Vitamin B3 | Olive leaf | Goldenseal |
| Vitamin B3 | Olive leaf | Fenugreek |
| Vitamin B3 | Olive leaf | Mullein |
| Vitamin B3 | Olive leaf | Phenol |
| Vitamin B3 | Olive leaf | Camphor |
| Vitamin B3 | Olive leaf | Pectin |
| Vitamin B3 | Olive leaf | Eucalyptus Oil |
| Vitamin B3 | Olive leaf | Peppermint Oil |
| Vitamin B3 | Olive leaf | Spearmint Oil |
| Vitamin B3 | Wild indigo | Goldenseal |
| Vitamin B3 | Wild indigo | Fenugreek |
| Vitamin B3 | Wild indigo | Mullein |
| Vitamin B3 | Wild indigo | Phenol |
| Vitamin B3 | Wild indigo | Camphor |
| Vitamin B3 | Wild indigo | Pectin |
| Vitamin B3 | Wild indigo | Eucalyptus Oil |
| Vitamin B3 | Wild indigo | Peppermint Oil |
| Vitamin B3 | Wild indigo | Spearmint Oil |
| Vitamin B3 | Goldenseal | Fenugreek |
| Vitamin B3 | Goldenseal | Mullein |
| Vitamin B3 | Goldenseal | Phenol |
| Vitamin B3 | Goldenseal | Camphor |
| Vitamin B3 | Goldenseal | Pectin |
| Vitamin B3 | Goldenseal | Eucalyptus Oil |

TABLE 3-continued

Three Ingredient Combinations

| First Ingredient | Second Ingredient | Third Ingredient |
|---|---|---|
| Vitamin B3 | Goldenseal | Peppermint Oil |
| Vitamin B3 | Goldenseal | Spearmint Oil |
| Vitamin B3 | Fenugreek | Mullein |
| Vitamin B3 | Fenugreek | Phenol |
| Vitamin B3 | Fenugreek | Camphor |
| Vitamin B3 | Fenugreek | Pectin |
| Vitamin B3 | Fenugreek | Eucalyptus Oil |
| Vitamin B3 | Fenugreek | Peppermint Oil |
| Vitamin B3 | Fenugreek | Spearmint Oil |
| Vitamin B3 | Mullein | Phenol |
| Vitamin B3 | Mullein | Camphor |
| Vitamin B3 | Mullein | Pectin |
| Vitamin B3 | Mullein | Eucalyptus Oil |
| Vitamin B3 | Mullein | Peppermint Oil |
| Vitamin B3 | Mullein | Spearmint Oil |
| Vitamin B3 | Phenol | Camphor |
| Vitamin B3 | Phenol | Pectin |
| Vitamin B3 | Phenol | Eucalyptus Oil |
| Vitamin B3 | Phenol | Peppermint Oil |
| Vitamin B3 | Phenol | Spearmint Oil |
| Vitamin B3 | Camphor | Pectin |
| Vitamin B3 | Camphor | Eucalyptus Oil |
| Vitamin B3 | Camphor | Peppermint Oil |
| Vitamin B3 | Camphor | Spearmint Oil |
| Vitamin B3 | Pectin | Eucalyptus Oil |
| Vitamin B3 | Pectin | Peppermint Oil |
| Vitamin B3 | Pectin | Spearmint Oil |
| Vitamin B3 | Eucalyptus Oil | Peppermint Oil |
| Vitamin B3 | Eucalyptus Oil | Spearmint Oil |
| Vitamin B3 | Peppermint Oil | Spearmint Oil |
| Vitamin B5 | Vitamin B6 | Vitamin B7 |
| Vitamin B5 | Vitamin B6 | Vitamin B8 |
| Vitamin B5 | Vitamin B6 | Vitamin B9 |
| Vitamin B5 | Vitamin B6 | Vitamin B12 |
| Vitamin B5 | Vitamin B6 | Vitamin C |
| Vitamin B5 | Vitamin B6 | Vitamin E |
| Vitamin B5 | Vitamin B6 | Zinc |
| Vitamin B5 | Vitamin B6 | Magnesium |
| Vitamin B5 | Vitamin B6 | Selenium |
| Vitamin B5 | Vitamin B6 | Echinacea |
| Vitamin B5 | Vitamin B6 | Olive leaf |
| Vitamin B5 | Vitamin B6 | Wild indigo |
| Vitamin B5 | Vitamin B6 | Goldenseal |
| Vitamin B5 | Vitamin B6 | Fenugreek |
| Vitamin B5 | Vitamin B6 | Mullein |
| Vitamin B5 | Vitamin B6 | Phenol |
| Vitamin B5 | Vitamin B6 | Camphor |
| Vitamin B5 | Vitamin B6 | Pectin |
| Vitamin B5 | Vitamin B6 | Eucalyptus Oil |
| Vitamin B5 | Vitamin B6 | Peppermint Oil |
| Vitamin B5 | Vitamin B6 | Spearmint Oil |
| Vitamin B5 | Vitamin B7 | Vitamin B8 |
| Vitamin B5 | Vitamin B7 | Vitamin B9 |
| Vitamin B5 | Vitamin B7 | Vitamin B12 |
| Vitamin B5 | Vitamin B7 | Vitamin C |
| Vitamin B5 | Vitamin B7 | Vitamin E |
| Vitamin B5 | Vitamin B7 | Zinc |
| Vitamin B5 | Vitamin B7 | Magnesium |
| Vitamin B5 | Vitamin B7 | Selenium |
| Vitamin B5 | Vitamin B7 | Echinacea |
| Vitamin B5 | Vitamin B7 | Olive leaf |
| Vitamin B5 | Vitamin B7 | Wild indigo |
| Vitamin B5 | Vitamin B7 | Goldenseal |
| Vitamin B5 | Vitamin B7 | Fenugreek |
| Vitamin B5 | Vitamin B7 | Mullein |
| Vitamin B5 | Vitamin B7 | Phenol |
| Vitamin B5 | Vitamin B7 | Camphor |
| Vitamin B5 | Vitamin B7 | Pectin |
| Vitamin B5 | Vitamin B7 | Eucalyptus Oil |
| Vitamin B5 | Vitamin B7 | Peppermint Oil |
| Vitamin B5 | Vitamin B7 | Spearmint Oil |
| Vitamin B5 | Vitamin B8 | Vitamin B9 |
| Vitamin B5 | Vitamin B8 | Vitamin B12 |
| Vitamin B5 | Vitamin B8 | Vitamin C |
| Vitamin B5 | Vitamin B8 | Vitamin E |
| Vitamin B5 | Vitamin B8 | Zinc |
| Vitamin B5 | Vitamin B8 | Magnesium |
| Vitamin B5 | Vitamin B8 | Selenium |
| Vitamin B5 | Vitamin B8 | Echinacea |
| Vitamin B5 | Vitamin B8 | Olive leaf |
| Vitamin B5 | Vitamin B8 | Wild indigo |
| Vitamin B5 | Vitamin B8 | Goldenseal |
| Vitamin B5 | Vitamin B8 | Fenugreek |
| Vitamin B5 | Vitamin B8 | Mullein |
| Vitamin B5 | Vitamin B8 | Phenol |
| Vitamin B5 | Vitamin B8 | Camphor |
| Vitamin B5 | Vitamin B8 | Pectin |
| Vitamin B5 | Vitamin B8 | Eucalyptus Oil |
| Vitamin B5 | Vitamin B8 | Peppermint Oil |
| Vitamin B5 | Vitamin B8 | Spearmint Oil |
| Vitamin B5 | Vitamin B9 | Vitamin B12 |
| Vitamin B5 | Vitamin B9 | Vitamin C |
| Vitamin B5 | Vitamin B9 | Vitamin E |
| Vitamin B5 | Vitamin B9 | Zinc |
| Vitamin B5 | Vitamin B9 | Magnesium |
| Vitamin B5 | Vitamin B9 | Selenium |
| Vitamin B5 | Vitamin B9 | Echinacea |
| Vitamin B5 | Vitamin B9 | Olive leaf |
| Vitamin B5 | Vitamin B9 | Wild indigo |
| Vitamin B5 | Vitamin B9 | Goldenseal |
| Vitamin B5 | Vitamin B9 | Fenugreek |
| Vitamin B5 | Vitamin B9 | Mullein |
| Vitamin B5 | Vitamin B9 | Phenol |
| Vitamin B5 | Vitamin B9 | Camphor |
| Vitamin B5 | Vitamin B9 | Pectin |
| Vitamin B5 | Vitamin B9 | Eucalyptus Oil |
| Vitamin B5 | Vitamin B9 | Peppermint Oil |
| Vitamin B5 | Vitamin B9 | Spearmint Oil |
| Vitamin B5 | Vitamin B12 | Vitamin C |
| Vitamin B5 | Vitamin B12 | Vitamin E |
| Vitamin B5 | Vitamin B12 | Zinc |
| Vitamin B5 | Vitamin B12 | Magnesium |
| Vitamin B5 | Vitamin B12 | Selenium |
| Vitamin B5 | Vitamin B12 | Echinacea |
| Vitamin B5 | Vitamin B12 | Olive leaf |
| Vitamin B5 | Vitamin B12 | Wild indigo |
| Vitamin B5 | Vitamin B12 | Goldenseal |
| Vitamin B5 | Vitamin B12 | Fenugreek |
| Vitamin B5 | Vitamin B12 | Mullein |
| Vitamin B5 | Vitamin B12 | Phenol |
| Vitamin B5 | Vitamin B12 | Camphor |
| Vitamin B5 | Vitamin B12 | Pectin |
| Vitamin B5 | Vitamin B12 | Eucalyptus Oil |
| Vitamin B5 | Vitamin B12 | Peppermint Oil |
| Vitamin B5 | Vitamin B12 | Spearmint Oil |
| Vitamin B5 | Vitamin C | Vitamin E |
| Vitamin B5 | Vitamin C | Zinc |
| Vitamin B5 | Vitamin C | Magnesium |
| Vitamin B5 | Vitamin C | Selenium |
| Vitamin B5 | Vitamin C | Echinacea |
| Vitamin B5 | Vitamin C | Olive leaf |
| Vitamin B5 | Vitamin C | Wild indigo |
| Vitamin B5 | Vitamin C | Goldenseal |
| Vitamin B5 | Vitamin C | Fenugreek |
| Vitamin B5 | Vitamin C | Mullein |
| Vitamin B5 | Vitamin C | Phenol |
| Vitamin B5 | Vitamin C | Camphor |
| Vitamin B5 | Vitamin C | Pectin |
| Vitamin B5 | Vitamin C | Eucalyptus Oil |
| Vitamin B5 | Vitamin C | Peppermint Oil |
| Vitamin B5 | Vitamin C | Spearmint Oil |
| Vitamin B5 | Vitamin E | Zinc |
| Vitamin B5 | Vitamin E | Magnesium |
| Vitamin B5 | Vitamin E | Selenium |
| Vitamin B5 | Vitamin E | Echinacea |
| Vitamin B5 | Vitamin E | Olive leaf |
| Vitamin B5 | Vitamin E | Wild indigo |
| Vitamin B5 | Vitamin E | Goldenseal |
| Vitamin B5 | Vitamin E | Fenugreek |
| Vitamin B5 | Vitamin E | Mullein |
| Vitamin B5 | Vitamin E | Phenol |
| Vitamin B5 | Vitamin E | Camphor |

TABLE 3-continued

Three Ingredient Combinations

| First Ingredient | Second Ingredient | Third Ingredient |
|---|---|---|
| Vitamin B5 | Vitamin E | Pectin |
| Vitamin B5 | Vitamin E | Eucalyptus Oil |
| Vitamin B5 | Vitamin E | Peppermint Oil |
| Vitamin B5 | Vitamin E | Spearmint Oil |
| Vitamin B5 | Zinc | Magnesium |
| Vitamin B5 | Zinc | Selenium |
| Vitamin B5 | Zinc | Echinacea |
| Vitamin B5 | Zinc | Olive leaf |
| Vitamin B5 | Zinc | Wild indigo |
| Vitamin B5 | Zinc | Goldenseal |
| Vitamin B5 | Zinc | Fenugreek |
| Vitamin B5 | Zinc | Mullein |
| Vitamin B5 | Zinc | Phenol |
| Vitamin B5 | Zinc | Camphor |
| Vitamin B5 | Zinc | Pectin |
| Vitamin B5 | Zinc | Eucalyptus Oil |
| Vitamin B5 | Zinc | Peppermint Oil |
| Vitamin B5 | Zinc | Spearmint Oil |
| Vitamin B5 | Magnesium | Selenium |
| Vitamin B5 | Magnesium | Echinacea |
| Vitamin B5 | Magnesium | Olive leaf |
| Vitamin B5 | Magnesium | Wild indigo |
| Vitamin B5 | Magnesium | Goldenseal |
| Vitamin B5 | Magnesium | Fenugreek |
| Vitamin B5 | Magnesium | Mullein |
| Vitamin B5 | Magnesium | Phenol |
| Vitamin B5 | Magnesium | Camphor |
| Vitamin B5 | Magnesium | Pectin |
| Vitamin B5 | Magnesium | Eucalyptus Oil |
| Vitamin B5 | Magnesium | Peppermint Oil |
| Vitamin B5 | Magnesium | Spearmint Oil |
| Vitamin B5 | Selenium | Echinacea |
| Vitamin B5 | Selenium | Olive leaf |
| Vitamin B5 | Selenium | Wild indigo |
| Vitamin B5 | Selenium | Goldenseal |
| Vitamin B5 | Selenium | Fenugreek |
| Vitamin B5 | Selenium | Mullein |
| Vitamin B5 | Selenium | Phenol |
| Vitamin B5 | Selenium | Camphor |
| Vitamin B5 | Selenium | Pectin |
| Vitamin B5 | Selenium | Eucalyptus Oil |
| Vitamin B5 | Selenium | Peppermint Oil |
| Vitamin B5 | Selenium | Spearmint Oil |
| Vitamin B5 | Echinacea | Olive leaf |
| Vitamin B5 | Echinacea | Wild indigo |
| Vitamin B5 | Echinacea | Goldenseal |
| Vitamin B5 | Echinacea | Fenugreek |
| Vitamin B5 | Echinacea | Mullein |
| Vitamin B5 | Echinacea | Phenol |
| Vitamin B5 | Echinacea | Camphor |
| Vitamin B5 | Echinacea | Pectin |
| Vitamin B5 | Echinacea | Eucalyptus Oil |
| Vitamin B5 | Echinacea | Peppermint Oil |
| Vitamin B5 | Echinacea | Spearmint Oil |
| Vitamin B5 | Olive leaf | Wild indigo |
| Vitamin B5 | Olive leaf | Goldenseal |
| Vitamin B5 | Olive leaf | Fenugreek |
| Vitamin B5 | Olive leaf | Mullein |
| Vitamin B5 | Olive leaf | Phenol |
| Vitamin B5 | Olive leaf | Camphor |
| Vitamin B5 | Olive leaf | Pectin |
| Vitamin B5 | Olive leaf | Eucalyptus Oil |
| Vitamin B5 | Olive leaf | Peppermint Oil |
| Vitamin B5 | Olive leaf | Spearmint Oil |
| Vitamin B5 | Wild indigo | Goldenseal |
| Vitamin B5 | Wild indigo | Fenugreek |
| Vitamin B5 | Wild indigo | Mullein |
| Vitamin B5 | Wild indigo | Phenol |
| Vitamin B5 | Wild indigo | Camphor |
| Vitamin B5 | Wild indigo | Pectin |
| Vitamin B5 | Wild indigo | Eucalyptus Oil |
| Vitamin B5 | Wild indigo | Peppermint Oil |
| Vitamin B5 | Wild indigo | Spearmint Oil |
| Vitamin B5 | Goldenseal | Fenugreek |
| Vitamin B5 | Goldenseal | Mullein |
| Vitamin B5 | Goldenseal | Phenol |
| Vitamin B5 | Goldenseal | Camphor |
| Vitamin B5 | Goldenseal | Pectin |
| Vitamin B5 | Goldenseal | Eucalyptus Oil |
| Vitamin B5 | Goldenseal | Peppermint Oil |
| Vitamin B5 | Goldenseal | Spearmint Oil |
| Vitamin B5 | Fenugreek | Mullein |
| Vitamin B5 | Fenugreek | Phenol |
| Vitamin B5 | Fenugreek | Camphor |
| Vitamin B5 | Fenugreek | Pectin |
| Vitamin B5 | Fenugreek | Eucalyptus Oil |
| Vitamin B5 | Fenugreek | Peppermint Oil |
| Vitamin B5 | Fenugreek | Spearmint Oil |
| Vitamin B5 | Mullein | Phenol |
| Vitamin B5 | Mullein | Camphor |
| Vitamin B5 | Mullein | Pectin |
| Vitamin B5 | Mullein | Eucalyptus Oil |
| Vitamin B5 | Mullein | Peppermint Oil |
| Vitamin B5 | Mullein | Spearmint Oil |
| Vitamin B5 | Phenol | Camphor |
| Vitamin B5 | Phenol | Pectin |
| Vitamin B5 | Phenol | Eucalyptus Oil |
| Vitamin B5 | Phenol | Peppermint Oil |
| Vitamin B5 | Phenol | Spearmint Oil |
| Vitamin B5 | Camphor | Pectin |
| Vitamin B5 | Camphor | Eucalyptus Oil |
| Vitamin B5 | Camphor | Peppermint Oil |
| Vitamin B5 | Camphor | Spearmint Oil |
| Vitamin B5 | Pectin | Eucalyptus Oil |
| Vitamin B5 | Pectin | Peppermint Oil |
| Vitamin B5 | Pectin | Spearmint Oil |
| Vitamin B5 | Eucalyptus Oil | Peppermint Oil |
| Vitamin B5 | Eucalyptus Oil | Spearmint Oil |
| Vitamin B5 | Peppermint Oil | Spearmint Oil |
| Vitamin B6 | Vitamin B7 | Vitamin B8 |
| Vitamin B6 | Vitamin B7 | Vitamin B9 |
| Vitamin B6 | Vitamin B7 | Vitamin B12 |
| Vitamin B6 | Vitamin B7 | Vitamin C |
| Vitamin B6 | Vitamin B7 | Vitamin E |
| Vitamin B6 | Vitamin B7 | Zinc |
| Vitamin B6 | Vitamin B7 | Magnesium |
| Vitamin B6 | Vitamin B7 | Selenium |
| Vitamin B6 | Vitamin B7 | Echinacea |
| Vitamin B6 | Vitamin B7 | Olive leaf |
| Vitamin B6 | Vitamin B7 | Wild indigo |
| Vitamin B6 | Vitamin B7 | Goldenseal |
| Vitamin B6 | Vitamin B7 | Fenugreek |
| Vitamin B6 | Vitamin B7 | Mullein |
| Vitamin B6 | Vitamin B7 | Phenol |
| Vitamin B6 | Vitamin B7 | Camphor |
| Vitamin B6 | Vitamin B7 | Pectin |
| Vitamin B6 | Vitamin B7 | Eucalyptus Oil |
| Vitamin B6 | Vitamin B7 | Peppermint Oil |
| Vitamin B6 | Vitamin B7 | Spearmint Oil |
| Vitamin B6 | Vitamin B8 | Vitamin B9 |
| Vitamin B6 | Vitamin B8 | Vitamin B12 |
| Vitamin B6 | Vitamin B8 | Vitamin C |
| Vitamin B6 | Vitamin B8 | Vitamin E |
| Vitamin B6 | Vitamin B8 | Zinc |
| Vitamin B6 | Vitamin B8 | Magnesium |
| Vitamin B6 | Vitamin B8 | Selenium |
| Vitamin B6 | Vitamin B8 | Echinacea |
| Vitamin B6 | Vitamin B8 | Olive leaf |
| Vitamin B6 | Vitamin B8 | Wild indigo |
| Vitamin B6 | Vitamin B8 | Goldenseal |
| Vitamin B6 | Vitamin B8 | Fenugreek |
| Vitamin B6 | Vitamin B8 | Mullein |
| Vitamin B6 | Vitamin B8 | Phenol |
| Vitamin B6 | Vitamin B8 | Camphor |
| Vitamin B6 | Vitamin B8 | Pectin |
| Vitamin B6 | Vitamin B8 | Eucalyptus Oil |
| Vitamin B6 | Vitamin B8 | Peppermint Oil |
| Vitamin B6 | Vitamin B8 | Spearmint Oil |
| Vitamin B6 | Vitamin B9 | Vitamin B12 |
| Vitamin B6 | Vitamin B9 | Vitamin C |
| Vitamin B6 | Vitamin B9 | Vitamin E |
| Vitamin B6 | Vitamin B9 | Zinc |

TABLE 3-continued

Three Ingredient Combinations

| First Ingredient | Second Ingredient | Third Ingredient |
|---|---|---|
| Vitamin B6 | Vitamin B9 | Magnesium |
| Vitamin B6 | Vitamin B9 | Selenium |
| Vitamin B6 | Vitamin B9 | Echinacea |
| Vitamin B6 | Vitamin B9 | Olive leaf |
| Vitamin B6 | Vitamin B9 | Wild indigo |
| Vitamin B6 | Vitamin B9 | Goldenseal |
| Vitamin B6 | Vitamin B9 | Fenugreek |
| Vitamin B6 | Vitamin B9 | Mullein |
| Vitamin B6 | Vitamin B9 | Phenol |
| Vitamin B6 | Vitamin B9 | Camphor |
| Vitamin B6 | Vitamin B9 | Pectin |
| Vitamin B6 | Vitamin B9 | Eucalyptus Oil |
| Vitamin B6 | Vitamin B9 | Peppermint Oil |
| Vitamin B6 | Vitamin B9 | Spearmint Oil |
| Vitamin B6 | Vitamin B12 | Vitamin C |
| Vitamin B6 | Vitamin B12 | Vitamin E |
| Vitamin B6 | Vitamin B12 | Zinc |
| Vitamin B6 | Vitamin B12 | Magnesium |
| Vitamin B6 | Vitamin B12 | Selenium |
| Vitamin B6 | Vitamin B12 | Echinacea |
| Vitamin B6 | Vitamin B12 | Olive leaf |
| Vitamin B6 | Vitamin B12 | Wild indigo |
| Vitamin B6 | Vitamin B12 | Goldenseal |
| Vitamin B6 | Vitamin B12 | Fenugreek |
| Vitamin B6 | Vitamin B12 | Mullein |
| Vitamin B6 | Vitamin B12 | Phenol |
| Vitamin B6 | Vitamin B12 | Camphor |
| Vitamin B6 | Vitamin B12 | Pectin |
| Vitamin B6 | Vitamin B12 | Eucalyptus Oil |
| Vitamin B6 | Vitamin B12 | Peppermint Oil |
| Vitamin B6 | Vitamin B12 | Spearmint Oil |
| Vitamin B6 | Vitamin C | Vitamin E |
| Vitamin B6 | Vitamin C | Zinc |
| Vitamin B6 | Vitamin C | Magnesium |
| Vitamin B6 | Vitamin C | Selenium |
| Vitamin B6 | Vitamin C | Echinacea |
| Vitamin B6 | Vitamin C | Olive leaf |
| Vitamin B6 | Vitamin C | Wild indigo |
| Vitamin B6 | Vitamin C | Goldenseal |
| Vitamin B6 | Vitamin C | Fenugreek |
| Vitamin B6 | Vitamin C | Mullein |
| Vitamin B6 | Vitamin C | Phenol |
| Vitamin B6 | Vitamin C | Camphor |
| Vitamin B6 | Vitamin C | Pectin |
| Vitamin B6 | Vitamin C | Eucalyptus Oil |
| Vitamin B6 | Vitamin C | Peppermint Oil |
| Vitamin B6 | Vitamin C | Spearmint Oil |
| Vitamin B6 | Vitamin E | Zinc |
| Vitamin B6 | Vitamin E | Magnesium |
| Vitamin B6 | Vitamin E | Selenium |
| Vitamin B6 | Vitamin E | Echinacea |
| Vitamin B6 | Vitamin E | Olive leaf |
| Vitamin B6 | Vitamin E | Wild indigo |
| Vitamin B6 | Vitamin E | Goldenseal |
| Vitamin B6 | Vitamin E | Fenugreek |
| Vitamin B6 | Vitamin E | Mullein |
| Vitamin B6 | Vitamin E | Phenol |
| Vitamin B6 | Vitamin E | Camphor |
| Vitamin B6 | Vitamin E | Pectin |
| Vitamin B6 | Vitamin E | Eucalyptus Oil |
| Vitamin B6 | Vitamin E | Peppermint Oil |
| Vitamin B6 | Vitamin E | Spearmint Oil |
| Vitamin B6 | Zinc | Magnesium |
| Vitamin B6 | Zinc | Selenium |
| Vitamin B6 | Zinc | Echinacea |
| Vitamin B6 | Zinc | Olive leaf |
| Vitamin B6 | Zinc | Wild indigo |
| Vitamin B6 | Zinc | Goldenseal |
| Vitamin B6 | Zinc | Fenugreek |
| Vitamin B6 | Zinc | Mullein |
| Vitamin B6 | Zinc | Phenol |
| Vitamin B6 | Zinc | Camphor |
| Vitamin B6 | Zinc | Pectin |
| Vitamin B6 | Zinc | Eucalyptus Oil |
| Vitamin B6 | Zinc | Peppermint Oil |
| Vitamin B6 | Zinc | Spearmint Oil |
| Vitamin B6 | Magnesium | Selenium |
| Vitamin B6 | Magnesium | Echinacea |
| Vitamin B6 | Magnesium | Olive leaf |
| Vitamin B6 | Magnesium | Wild indigo |
| Vitamin B6 | Magnesium | Goldenseal |
| Vitamin B6 | Magnesium | Fenugreek |
| Vitamin B6 | Magnesium | Mullein |
| Vitamin B6 | Magnesium | Phenol |
| Vitamin B6 | Magnesium | Camphor |
| Vitamin B6 | Magnesium | Pectin |
| Vitamin B6 | Magnesium | Eucalyptus Oil |
| Vitamin B6 | Magnesium | Peppermint Oil |
| Vitamin B6 | Magnesium | Spearmint Oil |
| Vitamin B6 | Selenium | Echinacea |
| Vitamin B6 | Selenium | Olive leaf |
| Vitamin B6 | Selenium | Wild indigo |
| Vitamin B6 | Selenium | Goldenseal |
| Vitamin B6 | Selenium | Fenugreek |
| Vitamin B6 | Selenium | Mullein |
| Vitamin B6 | Selenium | Phenol |
| Vitamin B6 | Selenium | Camphor |
| Vitamin B6 | Selenium | Pectin |
| Vitamin B6 | Selenium | Eucalyptus Oil |
| Vitamin B6 | Selenium | Peppermint Oil |
| Vitamin B6 | Selenium | Spearmint Oil |
| Vitamin B6 | Echinacea | Olive leaf |
| Vitamin B6 | Echinacea | Wild indigo |
| Vitamin B6 | Echinacea | Goldenseal |
| Vitamin B6 | Echinacea | Fenugreek |
| Vitamin B6 | Echinacea | Mullein |
| Vitamin B6 | Echinacea | Phenol |
| Vitamin B6 | Echinacea | Camphor |
| Vitamin B6 | Echinacea | Pectin |
| Vitamin B6 | Echinacea | Eucalyptus Oil |
| Vitamin B6 | Echinacea | Peppermint Oil |
| Vitamin B6 | Echinacea | Spearmint Oil |
| Vitamin B6 | Olive leaf | Wild indigo |
| Vitamin B6 | Olive leaf | Goldenseal |
| Vitamin B6 | Olive leaf | Fenugreek |
| Vitamin B6 | Olive leaf | Mullein |
| Vitamin B6 | Olive leaf | Phenol |
| Vitamin B6 | Olive leaf | Camphor |
| Vitamin B6 | Olive leaf | Pectin |
| Vitamin B6 | Olive leaf | Eucalyptus Oil |
| Vitamin B6 | Olive leaf | Peppermint Oil |
| Vitamin B6 | Olive leaf | Spearmint Oil |
| Vitamin B6 | Wild indigo | Goldenseal |
| Vitamin B6 | Wild indigo | Fenugreek |
| Vitamin B6 | Wild indigo | Mullein |
| Vitamin B6 | Wild indigo | Phenol |
| Vitamin B6 | Wild indigo | Camphor |
| Vitamin B6 | Wild indigo | Pectin |
| Vitamin B6 | Wild indigo | Eucalyptus Oil |
| Vitamin B6 | Wild indigo | Peppermint Oil |
| Vitamin B6 | Wild indigo | Spearmint Oil |
| Vitamin B6 | Goldenseal | Fenugreek |
| Vitamin B6 | Goldenseal | Mullein |
| Vitamin B6 | Goldenseal | Phenol |
| Vitamin B6 | Goldenseal | Camphor |
| Vitamin B6 | Goldenseal | Pectin |
| Vitamin B6 | Goldenseal | Eucalyptus Oil |
| Vitamin B6 | Goldenseal | Peppermint Oil |
| Vitamin B6 | Goldenseal | Spearmint Oil |
| Vitamin B6 | Fenugreek | Mullein |
| Vitamin B6 | Fenugreek | Phenol |
| Vitamin B6 | Fenugreek | Camphor |
| Vitamin B6 | Fenugreek | Pectin |
| Vitamin B6 | Fenugreek | Eucalyptus Oil |
| Vitamin B6 | Fenugreek | Peppermint Oil |
| Vitamin B6 | Fenugreek | Spearmint Oil |
| Vitamin B6 | Mullein | Phenol |
| Vitamin B6 | Mullein | Camphor |
| Vitamin B6 | Mullein | Pectin |
| Vitamin B6 | Mullein | Eucalyptus Oil |
| Vitamin B6 | Mullein | Peppermint Oil |
| Vitamin B6 | Mullein | Spearmint Oil |

TABLE 3-continued

Three Ingredient Combinations

| First Ingredient | Second Ingredient | Third Ingredient |
|---|---|---|
| Vitamin B6 | Phenol | Camphor |
| Vitamin B6 | Phenol | Pectin |
| Vitamin B6 | Phenol | Eucalyptus Oil |
| Vitamin B6 | Phenol | Peppermint Oil |
| Vitamin B6 | Phenol | Spearmint Oil |
| Vitamin B6 | Camphor | Pectin |
| Vitamin B6 | Camphor | Eucalyptus Oil |
| Vitamin B6 | Camphor | Peppermint Oil |
| Vitamin B6 | Camphor | Spearmint Oil |
| Vitamin B6 | Pectin | Eucalyptus Oil |
| Vitamin B6 | Pectin | Peppermint Oil |
| Vitamin B6 | Pectin | Spearmint Oil |
| Vitamin B6 | Eucalyptus Oil | Peppermint Oil |
| Vitamin B6 | Eucalyptus Oil | Spearmint Oil |
| Vitamin B6 | Peppermint Oil | Spearmint Oil |
| Vitamin B7 | Vitamin B8 | Vitamin B9 |
| Vitamin B7 | Vitamin B8 | Vitamin B12 |
| Vitamin B7 | Vitamin B8 | Vitamin C |
| Vitamin B7 | Vitamin B8 | Vitamin E |
| Vitamin B7 | Vitamin B8 | Zinc |
| Vitamin B7 | Vitamin B8 | Magnesium |
| Vitamin B7 | Vitamin B8 | Selenium |
| Vitamin B7 | Vitamin B8 | Echinacea |
| Vitamin B7 | Vitamin B8 | Olive leaf |
| Vitamin B7 | Vitamin B8 | Wild indigo |
| Vitamin B7 | Vitamin B8 | Goldenseal |
| Vitamin B7 | Vitamin B8 | Fenugreek |
| Vitamin B7 | Vitamin B8 | Mullein |
| Vitamin B7 | Vitamin B8 | Phenol |
| Vitamin B7 | Vitamin B8 | Camphor |
| Vitamin B7 | Vitamin B8 | Pectin |
| Vitamin B7 | Vitamin B8 | Eucalyptus Oil |
| Vitamin B7 | Vitamin B8 | Peppermint Oil |
| Vitamin B7 | Vitamin B8 | Spearmint Oil |
| Vitamin B7 | Vitamin B9 | Vitamin B12 |
| Vitamin B7 | Vitamin B9 | Vitamin C |
| Vitamin B7 | Vitamin B9 | Vitamin E |
| Vitamin B7 | Vitamin B9 | Zinc |
| Vitamin B7 | Vitamin B9 | Magnesium |
| Vitamin B7 | Vitamin B9 | Selenium |
| Vitamin B7 | Vitamin B9 | Echinacea |
| Vitamin B7 | Vitamin B9 | Olive leaf |
| Vitamin B7 | Vitamin B9 | Wild indigo |
| Vitamin B7 | Vitamin B9 | Goldenseal |
| Vitamin B7 | Vitamin B9 | Fenugreek |
| Vitamin B7 | Vitamin B9 | Mullein |
| Vitamin B7 | Vitamin B9 | Phenol |
| Vitamin B7 | Vitamin B9 | Camphor |
| Vitamin B7 | Vitamin B9 | Pectin |
| Vitamin B7 | Vitamin B9 | Eucalyptus Oil |
| Vitamin B7 | Vitamin B9 | Peppermint Oil |
| Vitamin B7 | Vitamin B9 | Spearmint Oil |
| Vitamin B7 | Vitamin B12 | Vitamin C |
| Vitamin B7 | Vitamin B12 | Vitamin E |
| Vitamin B7 | Vitamin B12 | Zinc |
| Vitamin B7 | Vitamin B12 | Magnesium |
| Vitamin B7 | Vitamin B12 | Selenium |
| Vitamin B7 | Vitamin B12 | Echinacea |
| Vitamin B7 | Vitamin B12 | Olive leaf |
| Vitamin B7 | Vitamin B12 | Wild indigo |
| Vitamin B7 | Vitamin B12 | Goldenseal |
| Vitamin B7 | Vitamin B12 | Fenugreek |
| Vitamin B7 | Vitamin B12 | Mullein |
| Vitamin B7 | Vitamin B12 | Phenol |
| Vitamin B7 | Vitamin B12 | Camphor |
| Vitamin B7 | Vitamin B12 | Pectin |
| Vitamin B7 | Vitamin B12 | Eucalyptus Oil |
| Vitamin B7 | Vitamin B12 | Peppermint Oil |
| Vitamin B7 | Vitamin B12 | Spearmint Oil |
| Vitamin B7 | Vitamin C | Vitamin E |
| Vitamin B7 | Vitamin C | Zinc |
| Vitamin B7 | Vitamin C | Magnesium |
| Vitamin B7 | Vitamin C | Selenium |
| Vitamin B7 | Vitamin C | Echinacea |
| Vitamin B7 | Vitamin C | Olive leaf |
| Vitamin B7 | Vitamin C | Wild indigo |
| Vitamin B7 | Vitamin C | Goldenseal |
| Vitamin B7 | Vitamin C | Fenugreek |
| Vitamin B7 | Vitamin C | Mullein |
| Vitamin B7 | Vitamin C | Phenol |
| Vitamin B7 | Vitamin C | Camphor |
| Vitamin B7 | Vitamin C | Pectin |
| Vitamin B7 | Vitamin C | Eucalyptus Oil |
| Vitamin B7 | Vitamin C | Peppermint Oil |
| Vitamin B7 | Vitamin C | Spearmint Oil |
| Vitamin B7 | Vitamin E | Zinc |
| Vitamin B7 | Vitamin E | Magnesium |
| Vitamin B7 | Vitamin E | Selenium |
| Vitamin B7 | Vitamin E | Echinacea |
| Vitamin B7 | Vitamin E | Olive leaf |
| Vitamin B7 | Vitamin E | Wild indigo |
| Vitamin B7 | Vitamin E | Goldenseal |
| Vitamin B7 | Vitamin E | Fenugreek |
| Vitamin B7 | Vitamin E | Mullein |
| Vitamin B7 | Vitamin E | Phenol |
| Vitamin B7 | Vitamin E | Camphor |
| Vitamin B7 | Vitamin E | Pectin |
| Vitamin B7 | Vitamin E | Eucalyptus Oil |
| Vitamin B7 | Vitamin E | Peppermint Oil |
| Vitamin B7 | Vitamin E | Spearmint Oil |
| Vitamin B7 | Zinc | Magnesium |
| Vitamin B7 | Zinc | Selenium |
| Vitamin B7 | Zinc | Echinacea |
| Vitamin B7 | Zinc | Olive leaf |
| Vitamin B7 | Zinc | Wild indigo |
| Vitamin B7 | Zinc | Goldenseal |
| Vitamin B7 | Zinc | Fenugreek |
| Vitamin B7 | Zinc | Mullein |
| Vitamin B7 | Zinc | Phenol |
| Vitamin B7 | Zinc | Camphor |
| Vitamin B7 | Zinc | Pectin |
| Vitamin B7 | Zinc | Eucalyptus Oil |
| Vitamin B7 | Zinc | Peppermint Oil |
| Vitamin B7 | Zinc | Spearmint Oil |
| Vitamin B7 | Magnesium | Selenium |
| Vitamin B7 | Magnesium | Echinacea |
| Vitamin B7 | Magnesium | Olive leaf |
| Vitamin B7 | Magnesium | Wild indigo |
| Vitamin B7 | Magnesium | Goldenseal |
| Vitamin B7 | Magnesium | Fenugreek |
| Vitamin B7 | Magnesium | Mullein |
| Vitamin B7 | Magnesium | Phenol |
| Vitamin B7 | Magnesium | Camphor |
| Vitamin B7 | Magnesium | Pectin |
| Vitamin B7 | Magnesium | Eucalyptus Oil |
| Vitamin B7 | Magnesium | Peppermint Oil |
| Vitamin B7 | Magnesium | Spearmint Oil |
| Vitamin B7 | Selenium | Echinacea |
| Vitamin B7 | Selenium | Olive leaf |
| Vitamin B7 | Selenium | Wild indigo |
| Vitamin B7 | Selenium | Goldenseal |
| Vitamin B7 | Selenium | Fenugreek |
| Vitamin B7 | Selenium | Mullein |
| Vitamin B7 | Selenium | Phenol |
| Vitamin B7 | Selenium | Camphor |
| Vitamin B7 | Selenium | Pectin |
| Vitamin B7 | Selenium | Eucalyptus Oil |
| Vitamin B7 | Selenium | Peppermint Oil |
| Vitamin B7 | Selenium | Spearmint Oil |
| Vitamin B7 | Echinacea | Olive leaf |
| Vitamin B7 | Echinacea | Wild indigo |
| Vitamin B7 | Echinacea | Goldenseal |
| Vitamin B7 | Echinacea | Fenugreek |
| Vitamin B7 | Echinacea | Mullein |
| Vitamin B7 | Echinacea | Phenol |
| Vitamin B7 | Echinacea | Camphor |
| Vitamin B7 | Echinacea | Pectin |
| Vitamin B7 | Echinacea | Eucalyptus Oil |
| Vitamin B7 | Echinacea | Peppermint Oil |
| Vitamin B7 | Echinacea | Spearmint Oil |
| Vitamin B7 | Olive leaf | Wild indigo |
| Vitamin B7 | Olive leaf | Goldenseal |

TABLE 3-continued

Three Ingredient Combinations

| First Ingredient | Second Ingredient | Third Ingredient |
|---|---|---|
| Vitamin B7 | Olive leaf | Fenugreek |
| Vitamin B7 | Olive leaf | Mullein |
| Vitamin B7 | Olive leaf | Phenol |
| Vitamin B7 | Olive leaf | Camphor |
| Vitamin B7 | Olive leaf | Pectin |
| Vitamin B7 | Olive leaf | Eucalyptus Oil |
| Vitamin B7 | Olive leaf | Peppermint Oil |
| Vitamin B7 | Olive leaf | Spearmint Oil |
| Vitamin B7 | Wild indigo | Goldenseal |
| Vitamin B7 | Wild indigo | Fenugreek |
| Vitamin B7 | Wild indigo | Mullein |
| Vitamin B7 | Wild indigo | Phenol |
| Vitamin B7 | Wild indigo | Camphor |
| Vitamin B7 | Wild indigo | Pectin |
| Vitamin B7 | Wild indigo | Eucalyptus Oil |
| Vitamin B7 | Wild indigo | Peppermint Oil |
| Vitamin B7 | Wild indigo | Spearmint Oil |
| Vitamin B7 | Goldenseal | Fenugreek |
| Vitamin B7 | Goldenseal | Mullein |
| Vitamin B7 | Goldenseal | Phenol |
| Vitamin B7 | Goldenseal | Camphor |
| Vitamin B7 | Goldenseal | Pectin |
| Vitamin B7 | Goldenseal | Eucalyptus Oil |
| Vitamin B7 | Goldenseal | Peppermint Oil |
| Vitamin B7 | Goldenseal | Spearmint Oil |
| Vitamin B7 | Fenugreek | Mullein |
| Vitamin B7 | Fenugreek | Phenol |
| Vitamin B7 | Fenugreek | Camphor |
| Vitamin B7 | Fenugreek | Pectin |
| Vitamin B7 | Fenugreek | Eucalyptus Oil |
| Vitamin B7 | Fenugreek | Peppermint Oil |
| Vitamin B7 | Fenugreek | Spearmint Oil |
| Vitamin B7 | Mullein | Phenol |
| Vitamin B7 | Mullein | Camphor |
| Vitamin B7 | Mullein | Pectin |
| Vitamin B7 | Mullein | Eucalyptus Oil |
| Vitamin B7 | Mullein | Peppermint Oil |
| Vitamin B7 | Mullein | Spearmint Oil |
| Vitamin B7 | Phenol | Camphor |
| Vitamin B7 | Phenol | Pectin |
| Vitamin B7 | Phenol | Eucalyptus Oil |
| Vitamin B7 | Phenol | Peppermint Oil |
| Vitamin B7 | Phenol | Spearmint Oil |
| Vitamin B7 | Camphor | Pectin |
| Vitamin B7 | Camphor | Eucalyptus Oil |
| Vitamin B7 | Camphor | Peppermint Oil |
| Vitamin B7 | Camphor | Spearmint Oil |
| Vitamin B7 | Pectin | Eucalyptus Oil |
| Vitamin B7 | Pectin | Peppermint Oil |
| Vitamin B7 | Pectin | Spearmint Oil |
| Vitamin B7 | Eucalyptus Oil | Peppermint Oil |
| Vitamin B7 | Eucalyptus Oil | Spearmint Oil |
| Vitamin B7 | Peppermint Oil | Spearmint Oil |
| Vitamin B8 | Vitamin B9 | Vitamin B12 |
| Vitamin B8 | Vitamin B9 | Vitamin C |
| Vitamin B8 | Vitamin B9 | Vitamin E |
| Vitamin B8 | Vitamin B9 | Zinc |
| Vitamin B8 | Vitamin B9 | Magnesium |
| Vitamin B8 | Vitamin B9 | Selenium |
| Vitamin B8 | Vitamin B9 | Echinacea |
| Vitamin B8 | Vitamin B9 | Olive leaf |
| Vitamin B8 | Vitamin B9 | Wild indigo |
| Vitamin B8 | Vitamin B9 | Goldenseal |
| Vitamin B8 | Vitamin B9 | Fenugreek |
| Vitamin B8 | Vitamin B9 | Mullein |
| Vitamin B8 | Vitamin B9 | Phenol |
| Vitamin B8 | Vitamin B9 | Camphor |
| Vitamin B8 | Vitamin B9 | Pectin |
| Vitamin B8 | Vitamin B9 | Eucalyptus Oil |
| Vitamin B8 | Vitamin B9 | Peppermint Oil |
| Vitamin B8 | Vitamin B9 | Spearmint Oil |
| Vitamin B8 | Vitamin B12 | Vitamin C |
| Vitamin B8 | Vitamin B12 | Vitamin E |
| Vitamin B8 | Vitamin B12 | Zinc |
| Vitamin B8 | Vitamin B12 | Magnesium |
| Vitamin B8 | Vitamin B12 | Selenium |
| Vitamin B8 | Vitamin B12 | Echinacea |
| Vitamin B8 | Vitamin B12 | Olive leaf |
| Vitamin B8 | Vitamin B12 | Wild indigo |
| Vitamin B8 | Vitamin B12 | Goldenseal |
| Vitamin B8 | Vitamin B12 | Fenugreek |
| Vitamin B8 | Vitamin B12 | Mullein |
| Vitamin B8 | Vitamin B12 | Phenol |
| Vitamin B8 | Vitamin B12 | Camphor |
| Vitamin B8 | Vitamin B12 | Pectin |
| Vitamin B8 | Vitamin B12 | Eucalyptus Oil |
| Vitamin B8 | Vitamin B12 | Peppermint Oil |
| Vitamin B8 | Vitamin B12 | Spearmint Oil |
| Vitamin B8 | Vitamin C | Vitamin E |
| Vitamin B8 | Vitamin C | Zinc |
| Vitamin B8 | Vitamin C | Magnesium |
| Vitamin B8 | Vitamin C | Selenium |
| Vitamin B8 | Vitamin C | Echinacea |
| Vitamin B8 | Vitamin C | Olive leaf |
| Vitamin B8 | Vitamin C | Wild indigo |
| Vitamin B8 | Vitamin C | Goldenseal |
| Vitamin B8 | Vitamin C | Fenugreek |
| Vitamin B8 | Vitamin C | Mullein |
| Vitamin B8 | Vitamin C | Phenol |
| Vitamin B8 | Vitamin C | Camphor |
| Vitamin B8 | Vitamin C | Pectin |
| Vitamin B8 | Vitamin C | Eucalyptus Oil |
| Vitamin B8 | Vitamin C | Peppermint Oil |
| Vitamin B8 | Vitamin C | Spearmint Oil |
| Vitamin B8 | Vitamin E | Zinc |
| Vitamin B8 | Vitamin E | Magnesium |
| Vitamin B8 | Vitamin E | Selenium |
| Vitamin B8 | Vitamin E | Echinacea |
| Vitamin B8 | Vitamin E | Olive leaf |
| Vitamin B8 | Vitamin E | Wild indigo |
| Vitamin B8 | Vitamin E | Goldenseal |
| Vitamin B8 | Vitamin E | Fenugreek |
| Vitamin B8 | Vitamin E | Mullein |
| Vitamin B8 | Vitamin E | Phenol |
| Vitamin B8 | Vitamin E | Camphor |
| Vitamin B8 | Vitamin E | Pectin |
| Vitamin B8 | Vitamin E | Eucalyptus Oil |
| Vitamin B8 | Vitamin E | Peppermint Oil |
| Vitamin B8 | Vitamin E | Spearmint Oil |
| Vitamin B8 | Zinc | Magnesium |
| Vitamin B8 | Zinc | Selenium |
| Vitamin B8 | Zinc | Echinacea |
| Vitamin B8 | Zinc | Olive leaf |
| Vitamin B8 | Zinc | Wild indigo |
| Vitamin B8 | Zinc | Goldenseal |
| Vitamin B8 | Zinc | Fenugreek |
| Vitamin B8 | Zinc | Mullein |
| Vitamin B8 | Zinc | Phenol |
| Vitamin B8 | Zinc | Camphor |
| Vitamin B8 | Zinc | Pectin |
| Vitamin B8 | Zinc | Eucalyptus Oil |
| Vitamin B8 | Zinc | Peppermint Oil |
| Vitamin B8 | Zinc | Spearmint Oil |
| Vitamin B8 | Magnesium | Selenium |
| Vitamin B8 | Magnesium | Echinacea |
| Vitamin B8 | Magnesium | Olive leaf |
| Vitamin B8 | Magnesium | Wild indigo |
| Vitamin B8 | Magnesium | Goldenseal |
| Vitamin B8 | Magnesium | Fenugreek |
| Vitamin B8 | Magnesium | Mullein |
| Vitamin B8 | Magnesium | Phenol |
| Vitamin B8 | Magnesium | Camphor |
| Vitamin B8 | Magnesium | Pectin |
| Vitamin B8 | Magnesium | Eucalyptus Oil |
| Vitamin B8 | Magnesium | Peppermint Oil |
| Vitamin B8 | Magnesium | Spearmint Oil |
| Vitamin B8 | Selenium | Echinacea |
| Vitamin B8 | Selenium | Olive leaf |
| Vitamin B8 | Selenium | Wild indigo |
| Vitamin B8 | Selenium | Goldenseal |
| Vitamin B8 | Selenium | Fenugreek |
| Vitamin B8 | Selenium | Mullein |

TABLE 3-continued

Three Ingredient Combinations

| First Ingredient | Second Ingredient | Third Ingredient |
| --- | --- | --- |
| Vitamin B8 | Selenium | Phenol |
| Vitamin B8 | Selenium | Camphor |
| Vitamin B8 | Selenium | Pectin |
| Vitamin B8 | Selenium | Eucalyptus Oil |
| Vitamin B8 | Selenium | Peppermint Oil |
| Vitamin B8 | Selenium | Spearmint Oil |
| Vitamin B8 | Echinacea | Olive leaf |
| Vitamin B8 | Echinacea | Wild indigo |
| Vitamin B8 | Echinacea | Goldenseal |
| Vitamin B8 | Echinacea | Fenugreek |
| Vitamin B8 | Echinacea | Mullein |
| Vitamin B8 | Echinacea | Phenol |
| Vitamin B8 | Echinacea | Camphor |
| Vitamin B8 | Echinacea | Pectin |
| Vitamin B8 | Echinacea | Eucalyptus Oil |
| Vitamin B8 | Echinacea | Peppermint Oil |
| Vitamin B8 | Echinacea | Spearmint Oil |
| Vitamin B8 | Olive leaf | Wild indigo |
| Vitamin B8 | Olive leaf | Goldenseal |
| Vitamin B8 | Olive leaf | Fenugreek |
| Vitamin B8 | Olive leaf | Mullein |
| Vitamin B8 | Olive leaf | Phenol |
| Vitamin B8 | Olive leaf | Camphor |
| Vitamin B8 | Olive leaf | Pectin |
| Vitamin B8 | Olive leaf | Eucalyptus Oil |
| Vitamin B8 | Olive leaf | Peppermint Oil |
| Vitamin B8 | Olive leaf | Spearmint Oil |
| Vitamin B8 | Wild indigo | Goldenseal |
| Vitamin B8 | Wild indigo | Fenugreek |
| Vitamin B8 | Wild indigo | Mullein |
| Vitamin B8 | Wild indigo | Phenol |
| Vitamin B8 | Wild indigo | Camphor |
| Vitamin B8 | Wild indigo | Pectin |
| Vitamin B8 | Wild indigo | Eucalyptus Oil |
| Vitamin B8 | Wild indigo | Peppermint Oil |
| Vitamin B8 | Wild indigo | Spearmint Oil |
| Vitamin B8 | Goldenseal | Fenugreek |
| Vitamin B8 | Goldenseal | Mullein |
| Vitamin B8 | Goldenseal | Phenol |
| Vitamin B8 | Goldenseal | Camphor |
| Vitamin B8 | Goldenseal | Pectin |
| Vitamin B8 | Goldenseal | Eucalyptus Oil |
| Vitamin B8 | Goldenseal | Peppermint Oil |
| Vitamin B8 | Goldenseal | Spearmint Oil |
| Vitamin B8 | Fenugreek | Mullein |
| Vitamin B8 | Fenugreek | Phenol |
| Vitamin B8 | Fenugreek | Camphor |
| Vitamin B8 | Fenugreek | Pectin |
| Vitamin B8 | Fenugreek | Eucalyptus Oil |
| Vitamin B8 | Fenugreek | Peppermint Oil |
| Vitamin B8 | Fenugreek | Spearmint Oil |
| Vitamin B8 | Mullein | Phenol |
| Vitamin B8 | Mullein | Camphor |
| Vitamin B8 | Mullein | Pectin |
| Vitamin B8 | Mullein | Eucalyptus Oil |
| Vitamin B8 | Mullein | Peppermint Oil |
| Vitamin B8 | Mullein | Spearmint Oil |
| Vitamin B8 | Phenol | Camphor |
| Vitamin B8 | Phenol | Pectin |
| Vitamin B8 | Phenol | Eucalyptus Oil |
| Vitamin B8 | Phenol | Peppermint Oil |
| Vitamin B8 | Phenol | Spearmint Oil |
| Vitamin B8 | Camphor | Pectin |
| Vitamin B8 | Camphor | Eucalyptus Oil |
| Vitamin B8 | Camphor | Peppermint Oil |
| Vitamin B8 | Camphor | Spearmint Oil |
| Vitamin B8 | Pectin | Eucalyptus Oil |
| Vitamin B8 | Pectin | Peppermint Oil |
| Vitamin B8 | Pectin | Spearmint Oil |
| Vitamin B8 | Eucalyptus Oil | Peppermint Oil |
| Vitamin B8 | Eucalyptus Oil | Spearmint Oil |
| Vitamin B8 | Peppermint Oil | Spearmint Oil |
| Vitamin B9 | Vitamin B12 | Vitamin C |
| Vitamin B9 | Vitamin B12 | Vitamin E |
| Vitamin B9 | Vitamin B12 | Zinc |
| Vitamin B9 | Vitamin B12 | Magnesium |
| Vitamin B9 | Vitamin B12 | Selenium |
| Vitamin B9 | Vitamin B12 | Echinacea |
| Vitamin B9 | Vitamin B12 | Olive leaf |
| Vitamin B9 | Vitamin B12 | Wild indigo |
| Vitamin B9 | Vitamin B12 | Goldenseal |
| Vitamin B9 | Vitamin B12 | Fenugreek |
| Vitamin B9 | Vitamin B12 | Mullein |
| Vitamin B9 | Vitamin B12 | Phenol |
| Vitamin B9 | Vitamin B12 | Camphor |
| Vitamin B9 | Vitamin B12 | Pectin |
| Vitamin B9 | Vitamin B12 | Eucalyptus Oil |
| Vitamin B9 | Vitamin B12 | Peppermint Oil |
| Vitamin B9 | Vitamin B12 | Spearmint Oil |
| Vitamin B9 | Vitamin C | Vitamin E |
| Vitamin B9 | Vitamin C | Zinc |
| Vitamin B9 | Vitamin C | Magnesium |
| Vitamin B9 | Vitamin C | Selenium |
| Vitamin B9 | Vitamin C | Echinacea |
| Vitamin B9 | Vitamin C | Olive leaf |
| Vitamin B9 | Vitamin C | Wild indigo |
| Vitamin B9 | Vitamin C | Goldenseal |
| Vitamin B9 | Vitamin C | Fenugreek |
| Vitamin B9 | Vitamin C | Mullein |
| Vitamin B9 | Vitamin C | Phenol |
| Vitamin B9 | Vitamin C | Camphor |
| Vitamin B9 | Vitamin C | Pectin |
| Vitamin B9 | Vitamin C | Eucalyptus Oil |
| Vitamin B9 | Vitamin C | Peppermint Oil |
| Vitamin B9 | Vitamin C | Spearmint Oil |
| Vitamin B9 | Vitamin E | Zinc |
| Vitamin B9 | Vitamin E | Magnesium |
| Vitamin B9 | Vitamin E | Selenium |
| Vitamin B9 | Vitamin E | Echinacea |
| Vitamin B9 | Vitamin E | Olive leaf |
| Vitamin B9 | Vitamin E | Wild indigo |
| Vitamin B9 | Vitamin E | Goldenseal |
| Vitamin B9 | Vitamin E | Fenugreek |
| Vitamin B9 | Vitamin E | Mullein |
| Vitamin B9 | Vitamin E | Phenol |
| Vitamin B9 | Vitamin E | Camphor |
| Vitamin B9 | Vitamin E | Pectin |
| Vitamin B9 | Vitamin E | Eucalyptus Oil |
| Vitamin B9 | Vitamin E | Peppermint Oil |
| Vitamin B9 | Vitamin E | Spearmint Oil |
| Vitamin B9 | Zinc | Magnesium |
| Vitamin B9 | Zinc | Selenium |
| Vitamin B9 | Zinc | Echinacea |
| Vitamin B9 | Zinc | Olive leaf |
| Vitamin B9 | Zinc | Wild indigo |
| Vitamin B9 | Zinc | Goldenseal |
| Vitamin B9 | Zinc | Fenugreek |
| Vitamin B9 | Zinc | Mullein |
| Vitamin B9 | Zinc | Phenol |
| Vitamin B9 | Zinc | Camphor |
| Vitamin B9 | Zinc | Pectin |
| Vitamin B9 | Zinc | Eucalyptus Oil |
| Vitamin B9 | Zinc | Peppermint Oil |
| Vitamin B9 | Zinc | Spearmint Oil |
| Vitamin B9 | Magnesium | Selenium |
| Vitamin B9 | Magnesium | Echinacea |
| Vitamin B9 | Magnesium | Olive leaf |
| Vitamin B9 | Magnesium | Wild indigo |
| Vitamin B9 | Magnesium | Goldenseal |
| Vitamin B9 | Magnesium | Fenugreek |
| Vitamin B9 | Magnesium | Mullein |
| Vitamin B9 | Magnesium | Phenol |
| Vitamin B9 | Magnesium | Camphor |
| Vitamin B9 | Magnesium | Pectin |
| Vitamin B9 | Magnesium | Eucalyptus Oil |
| Vitamin B9 | Magnesium | Peppermint Oil |
| Vitamin B9 | Magnesium | Spearmint Oil |
| Vitamin B9 | Selenium | Echinacea |
| Vitamin B9 | Selenium | Olive leaf |
| Vitamin B9 | Selenium | Wild indigo |
| Vitamin B9 | Selenium | Goldenseal |
| Vitamin B9 | Selenium | Fenugreek |

TABLE 3-continued

Three Ingredient Combinations

| First Ingredient | Second Ingredient | Third Ingredient |
|---|---|---|
| Vitamin B9 | Selenium | Mullein |
| Vitamin B9 | Selenium | Phenol |
| Vitamin B9 | Selenium | Camphor |
| Vitamin B9 | Selenium | Pectin |
| Vitamin B9 | Selenium | Eucalyptus Oil |
| Vitamin B9 | Selenium | Peppermint Oil |
| Vitamin B9 | Selenium | Spearmint Oil |
| Vitamin B9 | Echinacea | Olive leaf |
| Vitamin B9 | Echinacea | Wild indigo |
| Vitamin B9 | Echinacea | Goldenseal |
| Vitamin B9 | Echinacea | Fenugreek |
| Vitamin B9 | Echinacea | Mullein |
| Vitamin B9 | Echinacea | Phenol |
| Vitamin B9 | Echinacea | Camphor |
| Vitamin B9 | Echinacea | Pectin |
| Vitamin B9 | Echinacea | Eucalyptus Oil |
| Vitamin B9 | Echinacea | Peppermint Oil |
| Vitamin B9 | Echinacea | Spearmint Oil |
| Vitamin B9 | Olive leaf | Wild indigo |
| Vitamin B9 | Olive leaf | Goldenseal |
| Vitamin B9 | Olive leaf | Fenugreek |
| Vitamin B9 | Olive leaf | Mullein |
| Vitamin B9 | Olive leaf | Phenol |
| Vitamin B9 | Olive leaf | Camphor |
| Vitamin B9 | Olive leaf | Pectin |
| Vitamin B9 | Olive leaf | Eucalyptus Oil |
| Vitamin B9 | Olive leaf | Peppermint Oil |
| Vitamin B9 | Olive leaf | Spearmint Oil |
| Vitamin B9 | Wild indigo | Goldenseal |
| Vitamin B9 | Wild indigo | Fenugreek |
| Vitamin B9 | Wild indigo | Mullein |
| Vitamin B9 | Wild indigo | Phenol |
| Vitamin B9 | Wild indigo | Camphor |
| Vitamin B9 | Wild indigo | Pectin |
| Vitamin B9 | Wild indigo | Eucalyptus Oil |
| Vitamin B9 | Wild indigo | Peppermint Oil |
| Vitamin B9 | Wild indigo | Spearmint Oil |
| Vitamin B9 | Goldenseal | Fenugreek |
| Vitamin B9 | Goldenseal | Mullein |
| Vitamin B9 | Goldenseal | Phenol |
| Vitamin B9 | Goldenseal | Camphor |
| Vitamin B9 | Goldenseal | Pectin |
| Vitamin B9 | Goldenseal | Eucalyptus Oil |
| Vitamin B9 | Goldenseal | Peppermint Oil |
| Vitamin B9 | Goldenseal | Spearmint Oil |
| Vitamin B9 | Fenugreek | Mullein |
| Vitamin B9 | Fenugreek | Phenol |
| Vitamin B9 | Fenugreek | Camphor |
| Vitamin B9 | Fenugreek | Pectin |
| Vitamin B9 | Fenugreek | Eucalyptus Oil |
| Vitamin B9 | Fenugreek | Peppermint Oil |
| Vitamin B9 | Fenugreek | Spearmint Oil |
| Vitamin B9 | Mullein | Phenol |
| Vitamin B9 | Mullein | Camphor |
| Vitamin B9 | Mullein | Pectin |
| Vitamin B9 | Mullein | Eucalyptus Oil |
| Vitamin B9 | Mullein | Peppermint Oil |
| Vitamin B9 | Mullein | Spearmint Oil |
| Vitamin B9 | Phenol | Camphor |
| Vitamin B9 | Phenol | Pectin |
| Vitamin B9 | Phenol | Eucalyptus Oil |
| Vitamin B9 | Phenol | Peppermint Oil |
| Vitamin B9 | Phenol | Spearmint Oil |
| Vitamin B9 | Camphor | Pectin |
| Vitamin B9 | Camphor | Eucalyptus Oil |
| Vitamin B9 | Camphor | Peppermint Oil |
| Vitamin B9 | Camphor | Spearmint Oil |
| Vitamin B9 | Pectin | Eucalyptus Oil |
| Vitamin B9 | Pectin | Peppermint Oil |
| Vitamin B9 | Pectin | Spearmint Oil |
| Vitamin B9 | Eucalyptus Oil | Peppermint Oil |
| Vitamin B9 | Eucalyptus Oil | Spearmint Oil |
| Vitamin B9 | Peppermint Oil | Spearmint Oil |
| Vitamin B12 | Vitamin C | Vitamin E |
| Vitamin B12 | Vitamin C | Zinc |
| Vitamin B12 | Vitamin C | Magnesium |
| Vitamin B12 | Vitamin C | Selenium |
| Vitamin B12 | Vitamin C | Echinacea |
| Vitamin B12 | Vitamin C | Olive leaf |
| Vitamin B12 | Vitamin C | Wild indigo |
| Vitamin B12 | Vitamin C | Goldenseal |
| Vitamin B12 | Vitamin C | Fenugreek |
| Vitamin B12 | Vitamin C | Mullein |
| Vitamin B12 | Vitamin C | Phenol |
| Vitamin B12 | Vitamin C | Camphor |
| Vitamin B12 | Vitamin C | Pectin |
| Vitamin B12 | Vitamin C | Eucalyptus Oil |
| Vitamin B12 | Vitamin C | Peppermint Oil |
| Vitamin B12 | Vitamin C | Spearmint Oil |
| Vitamin B12 | Vitamin E | Zinc |
| Vitamin B12 | Vitamin E | Magnesium |
| Vitamin B12 | Vitamin E | Selenium |
| Vitamin B12 | Vitamin E | Echinacea |
| Vitamin B12 | Vitamin E | Olive leaf |
| Vitamin B12 | Vitamin E | Wild indigo |
| Vitamin B12 | Vitamin E | Goldenseal |
| Vitamin B12 | Vitamin E | Fenugreek |
| Vitamin B12 | Vitamin E | Mullein |
| Vitamin B12 | Vitamin E | Phenol |
| Vitamin B12 | Vitamin E | Camphor |
| Vitamin B12 | Vitamin E | Pectin |
| Vitamin B12 | Vitamin E | Eucalyptus Oil |
| Vitamin B12 | Vitamin E | Peppermint Oil |
| Vitamin B12 | Vitamin E | Spearmint Oil |
| Vitamin B12 | Zinc | Magnesium |
| Vitamin B12 | Zinc | Selenium |
| Vitamin B12 | Zinc | Echinacea |
| Vitamin B12 | Zinc | Olive leaf |
| Vitamin B12 | Zinc | Wild indigo |
| Vitamin B12 | Zinc | Goldenseal |
| Vitamin B12 | Zinc | Fenugreek |
| Vitamin B12 | Zinc | Mullein |
| Vitamin B12 | Zinc | Phenol |
| Vitamin B12 | Zinc | Camphor |
| Vitamin B12 | Zinc | Pectin |
| Vitamin B12 | Zinc | Eucalyptus Oil |
| Vitamin B12 | Zinc | Peppermint Oil |
| Vitamin B12 | Zinc | Spearmint Oil |
| Vitamin B12 | Magnesium | Selenium |
| Vitamin B12 | Magnesium | Echinacea |
| Vitamin B12 | Magnesium | Olive leaf |
| Vitamin B12 | Magnesium | Wild indigo |
| Vitamin B12 | Magnesium | Goldenseal |
| Vitamin B12 | Magnesium | Fenugreek |
| Vitamin B12 | Magnesium | Mullein |
| Vitamin B12 | Magnesium | Phenol |
| Vitamin B12 | Magnesium | Camphor |
| Vitamin B12 | Magnesium | Pectin |
| Vitamin B12 | Magnesium | Eucalyptus Oil |
| Vitamin B12 | Magnesium | Peppermint Oil |
| Vitamin B12 | Magnesium | Spearmint Oil |
| Vitamin B12 | Selenium | Echinacea |
| Vitamin B12 | Selenium | Olive leaf |
| Vitamin B12 | Selenium | Wild indigo |
| Vitamin B12 | Selenium | Goldenseal |
| Vitamin B12 | Selenium | Fenugreek |
| Vitamin B12 | Selenium | Mullein |
| Vitamin B12 | Selenium | Phenol |
| Vitamin B12 | Selenium | Camphor |
| Vitamin B12 | Selenium | Pectin |
| Vitamin B12 | Selenium | Eucalyptus Oil |
| Vitamin B12 | Selenium | Peppermint Oil |
| Vitamin B12 | Selenium | Spearmint Oil |
| Vitamin B12 | Echinacea | Olive leaf |
| Vitamin B12 | Echinacea | Wild indigo |
| Vitamin B12 | Echinacea | Goldenseal |
| Vitamin B12 | Echinacea | Fenugreek |
| Vitamin B12 | Echinacea | Mullein |
| Vitamin B12 | Echinacea | Phenol |
| Vitamin B12 | Echinacea | Camphor |
| Vitamin B12 | Echinacea | Pectin |
| Vitamin B12 | Echinacea | Eucalyptus Oil |

TABLE 3-continued

Three Ingredient Combinations

| First Ingredient | Second Ingredient | Third Ingredient |
|---|---|---|
| Vitamin B12 | Echinacea | Peppermint Oil |
| Vitamin B12 | Echinacea | Spearmint Oil |
| Vitamin B12 | Olive leaf | Wild indigo |
| Vitamin B12 | Olive leaf | Goldenseal |
| Vitamin B12 | Olive leaf | Fenugreek |
| Vitamin B12 | Olive leaf | Mullein |
| Vitamin B12 | Olive leaf | Phenol |
| Vitamin B12 | Olive leaf | Camphor |
| Vitamin B12 | Olive leaf | Pectin |
| Vitamin B12 | Olive leaf | Eucalyptus Oil |
| Vitamin B12 | Olive leaf | Peppermint Oil |
| Vitamin B12 | Olive leaf | Spearmint Oil |
| Vitamin B12 | Wild indigo | Goldenseal |
| Vitamin B12 | Wild indigo | Fenugreek |
| Vitamin B12 | Wild indigo | Mullein |
| Vitamin B12 | Wild indigo | Phenol |
| Vitamin B12 | Wild indigo | Camphor |
| Vitamin B12 | Wild indigo | Pectin |
| Vitamin B12 | Wild indigo | Eucalyptus Oil |
| Vitamin B12 | Wild indigo | Peppermint Oil |
| Vitamin B12 | Wild indigo | Spearmint Oil |
| Vitamin B12 | Goldenseal | Fenugreek |
| Vitamin B12 | Goldenseal | Mullein |
| Vitamin B12 | Goldenseal | Phenol |
| Vitamin B12 | Goldenseal | Camphor |
| Vitamin B12 | Goldenseal | Pectin |
| Vitamin B12 | Goldenseal | Eucalyptus Oil |
| Vitamin B12 | Goldenseal | Peppermint Oil |
| Vitamin B12 | Goldenseal | Spearmint Oil |
| Vitamin B12 | Fenugreek | Mullein |
| Vitamin B12 | Fenugreek | Phenol |
| Vitamin B12 | Fenugreek | Camphor |
| Vitamin B12 | Fenugreek | Pectin |
| Vitamin B12 | Fenugreek | Eucalyptus Oil |
| Vitamin B12 | Fenugreek | Peppermint Oil |
| Vitamin B12 | Fenugreek | Spearmint Oil |
| Vitamin B12 | Mullein | Phenol |
| Vitamin B12 | Mullein | Camphor |
| Vitamin B12 | Mullein | Pectin |
| Vitamin B12 | Mullein | Eucalyptus Oil |
| Vitamin B12 | Mullein | Peppermint Oil |
| Vitamin B12 | Mullein | Spearmint Oil |
| Vitamin B12 | Phenol | Camphor |
| Vitamin B12 | Phenol | Pectin |
| Vitamin B12 | Phenol | Eucalyptus Oil |
| Vitamin B12 | Phenol | Peppermint Oil |
| Vitamin B12 | Phenol | Spearmint Oil |
| Vitamin B12 | Camphor | Pectin |
| Vitamin B12 | Camphor | Eucalyptus Oil |
| Vitamin B12 | Camphor | Peppermint Oil |
| Vitamin B12 | Camphor | Spearmint Oil |
| Vitamin B12 | Pectin | Eucalyptus Oil |
| Vitamin B12 | Pectin | Peppermint Oil |
| Vitamin B12 | Pectin | Spearmint Oil |
| Vitamin B12 | Eucalyptus Oil | Peppermint Oil |
| Vitamin B12 | Eucalyptus Oil | Spearmint Oil |
| Vitamin B12 | Peppermint Oil | Spearmint Oil |
| Vitamin C | Vitamin E | Zinc |
| Vitamin C | Vitamin E | Magnesium |
| Vitamin C | Vitamin E | Selenium |
| Vitamin C | Vitamin E | Echinacea |
| Vitamin C | Vitamin E | Olive leaf |
| Vitamin C | Vitamin E | Wild indigo |
| Vitamin C | Vitamin E | Goldenseal |
| Vitamin C | Vitamin E | Fenugreek |
| Vitamin C | Vitamin E | Mullein |
| Vitamin C | Vitamin E | Phenol |
| Vitamin C | Vitamin E | Camphor |
| Vitamin C | Vitamin E | Pectin |
| Vitamin C | Vitamin E | Eucalyptus Oil |
| Vitamin C | Vitamin E | Peppermint Oil |
| Vitamin C | Vitamin E | Spearmint Oil |
| Vitamin C | Zinc | Magnesium |
| Vitamin C | Zinc | Selenium |
| Vitamin C | Zinc | Echinacea |
| Vitamin C | Zinc | Olive leaf |
| Vitamin C | Zinc | Wild indigo |
| Vitamin C | Zinc | Goldenseal |
| Vitamin C | Zinc | Fenugreek |
| Vitamin C | Zinc | Mullein |
| Vitamin C | Zinc | Phenol |
| Vitamin C | Zinc | Camphor |
| Vitamin C | Zinc | Pectin |
| Vitamin C | Zinc | Eucalyptus Oil |
| Vitamin C | Zinc | Peppermint Oil |
| Vitamin C | Zinc | Spearmint Oil |
| Vitamin C | Magnesium | Selenium |
| Vitamin C | Magnesium | Echinacea |
| Vitamin C | Magnesium | Olive leaf |
| Vitamin C | Magnesium | Wild indigo |
| Vitamin C | Magnesium | Goldenseal |
| Vitamin C | Magnesium | Fenugreek |
| Vitamin C | Magnesium | Mullein |
| Vitamin C | Magnesium | Phenol |
| Vitamin C | Magnesium | Camphor |
| Vitamin C | Magnesium | Pectin |
| Vitamin C | Magnesium | Eucalyptus Oil |
| Vitamin C | Magnesium | Peppermint Oil |
| Vitamin C | Magnesium | Spearmint Oil |
| Vitamin C | Selenium | Echinacea |
| Vitamin C | Selenium | Olive leaf |
| Vitamin C | Selenium | Wild indigo |
| Vitamin C | Selenium | Goldenseal |
| Vitamin C | Selenium | Fenugreek |
| Vitamin C | Selenium | Mullein |
| Vitamin C | Selenium | Phenol |
| Vitamin C | Selenium | Camphor |
| Vitamin C | Selenium | Pectin |
| Vitamin C | Selenium | Eucalyptus Oil |
| Vitamin C | Selenium | Peppermint Oil |
| Vitamin C | Selenium | Spearmint Oil |
| Vitamin C | Echinacea | Olive leaf |
| Vitamin C | Echinacea | Wild indigo |
| Vitamin C | Echinacea | Goldenseal |
| Vitamin C | Echinacea | Fenugreek |
| Vitamin C | Echinacea | Mullein |
| Vitamin C | Echinacea | Phenol |
| Vitamin C | Echinacea | Camphor |
| Vitamin C | Echinacea | Pectin |
| Vitamin C | Echinacea | Eucalyptus Oil |
| Vitamin C | Echinacea | Peppermint Oil |
| Vitamin C | Echinacea | Spearmint Oil |
| Vitamin C | Olive leaf | Wild indigo |
| Vitamin C | Olive leaf | Goldenseal |
| Vitamin C | Olive leaf | Fenugreek |
| Vitamin C | Olive leaf | Mullein |
| Vitamin C | Olive leaf | Phenol |
| Vitamin C | Olive leaf | Camphor |
| Vitamin C | Olive leaf | Pectin |
| Vitamin C | Olive leaf | Eucalyptus Oil |
| Vitamin C | Olive leaf | Peppermint Oil |
| Vitamin C | Olive leaf | Spearmint Oil |
| Vitamin C | Wild indigo | Goldenseal |
| Vitamin C | Wild indigo | Fenugreek |
| Vitamin C | Wild indigo | Mullein |
| Vitamin C | Wild indigo | Phenol |
| Vitamin C | Wild indigo | Camphor |
| Vitamin C | Wild indigo | Pectin |
| Vitamin C | Wild indigo | Eucalyptus Oil |
| Vitamin C | Wild indigo | Peppermint Oil |
| Vitamin C | Wild indigo | Spearmint Oil |
| Vitamin C | Goldenseal | Fenugreek |
| Vitamin C | Goldenseal | Mullein |
| Vitamin C | Goldenseal | Phenol |
| Vitamin C | Goldenseal | Camphor |
| Vitamin C | Goldenseal | Pectin |
| Vitamin C | Goldenseal | Eucalyptus Oil |
| Vitamin C | Goldenseal | Peppermint Oil |
| Vitamin C | Goldenseal | Spearmint Oil |
| Vitamin C | Fenugreek | Mullein |
| Vitamin C | Fenugreek | Phenol |
| Vitamin C | Fenugreek | Camphor |

TABLE 3-continued

Three Ingredient Combinations

| First Ingredient | Second Ingredient | Third Ingredient |
|---|---|---|
| Vitamin C | Fenugreek | Pectin |
| Vitamin C | Fenugreek | Eucalyptus Oil |
| Vitamin C | Fenugreek | Peppermint Oil |
| Vitamin C | Fenugreek | Spearmint Oil |
| Vitamin C | Mullein | Phenol |
| Vitamin C | Mullein | Camphor |
| Vitamin C | Mullein | Pectin |
| Vitamin C | Mullein | Eucalyptus Oil |
| Vitamin C | Mullein | Peppermint Oil |
| Vitamin C | Mullein | Spearmint Oil |
| Vitamin C | Phenol | Camphor |
| Vitamin C | Phenol | Pectin |
| Vitamin C | Phenol | Eucalyptus Oil |
| Vitamin C | Phenol | Peppermint Oil |
| Vitamin C | Phenol | Spearmint Oil |
| Vitamin C | Camphor | Pectin |
| Vitamin C | Camphor | Eucalyptus Oil |
| Vitamin C | Camphor | Peppermint Oil |
| Vitamin C | Camphor | Spearmint Oil |
| Vitamin C | Pectin | Eucalyptus Oil |
| Vitamin C | Pectin | Peppermint Oil |
| Vitamin C | Pectin | Spearmint Oil |
| Vitamin C | Eucalyptus Oil | Peppermint Oil |
| Vitamin C | Eucalyptus Oil | Spearmint Oil |
| Vitamin C | Peppermint Oil | Spearmint Oil |
| Vitamin E | Zinc | Magnesium |
| Vitamin E | Zinc | Selenium |
| Vitamin E | Zinc | Echinacea |
| Vitamin E | Zinc | Olive leaf |
| Vitamin E | Zinc | Wild indigo |
| Vitamin E | Zinc | Goldenseal |
| Vitamin E | Zinc | Fenugreek |
| Vitamin E | Zinc | Mullein |
| Vitamin E | Zinc | Phenol |
| Vitamin E | Zinc | Camphor |
| Vitamin E | Zinc | Pectin |
| Vitamin E | Zinc | Eucalyptus Oil |
| Vitamin E | Zinc | Peppermint Oil |
| Vitamin E | Zinc | Spearmint Oil |
| Vitamin E | Magnesium | Selenium |
| Vitamin E | Magnesium | Echinacea |
| Vitamin E | Magnesium | Olive leaf |
| Vitamin E | Magnesium | Wild indigo |
| Vitamin E | Magnesium | Goldenseal |
| Vitamin E | Magnesium | Fenugreek |
| Vitamin E | Magnesium | Mullein |
| Vitamin E | Magnesium | Phenol |
| Vitamin E | Magnesium | Camphor |
| Vitamin E | Magnesium | Pectin |
| Vitamin E | Magnesium | Eucalyptus Oil |
| Vitamin E | Magnesium | Peppermint Oil |
| Vitamin E | Magnesium | Spearmint Oil |
| Vitamin E | Selenium | Echinacea |
| Vitamin E | Selenium | Olive leaf |
| Vitamin E | Selenium | Wild indigo |
| Vitamin E | Selenium | Goldenseal |
| Vitamin E | Selenium | Fenugreek |
| Vitamin E | Selenium | Mullein |
| Vitamin E | Selenium | Phenol |
| Vitamin E | Selenium | Camphor |
| Vitamin E | Selenium | Pectin |
| Vitamin E | Selenium | Eucalyptus Oil |
| Vitamin E | Selenium | Peppermint Oil |
| Vitamin E | Selenium | Spearmint Oil |
| Vitamin E | Echinacea | Olive leaf |
| Vitamin E | Echinacea | Wild indigo |
| Vitamin E | Echinacea | Goldenseal |
| Vitamin E | Echinacea | Fenugreek |
| Vitamin E | Echinacea | Mullein |
| Vitamin E | Echinacea | Phenol |
| Vitamin E | Echinacea | Camphor |
| Vitamin E | Echinacea | Pectin |
| Vitamin E | Echinacea | Eucalyptus Oil |
| Vitamin E | Echinacea | Peppermint Oil |
| Vitamin E | Echinacea | Spearmint Oil |
| Vitamin E | Olive leaf | Wild indigo |
| Vitamin E | Olive leaf | Goldenseal |
| Vitamin E | Olive leaf | Fenugreek |
| Vitamin E | Olive leaf | Mullein |
| Vitamin E | Olive leaf | Phenol |
| Vitamin E | Olive leaf | Camphor |
| Vitamin E | Olive leaf | Pectin |
| Vitamin E | Olive leaf | Eucalyptus Oil |
| Vitamin E | Olive leaf | Peppermint Oil |
| Vitamin E | Olive leaf | Spearmint Oil |
| Vitamin E | Wild indigo | Goldenseal |
| Vitamin E | Wild indigo | Fenugreek |
| Vitamin E | Wild indigo | Mullein |
| Vitamin E | Wild indigo | Phenol |
| Vitamin E | Wild indigo | Camphor |
| Vitamin E | Wild indigo | Pectin |
| Vitamin E | Wild indigo | Eucalyptus Oil |
| Vitamin E | Wild indigo | Peppermint Oil |
| Vitamin E | Wild indigo | Spearmint Oil |
| Vitamin E | Goldenseal | Fenugreek |
| Vitamin E | Goldenseal | Mullein |
| Vitamin E | Goldenseal | Phenol |
| Vitamin E | Goldenseal | Camphor |
| Vitamin E | Goldenseal | Pectin |
| Vitamin E | Goldenseal | Eucalyptus Oil |
| Vitamin E | Goldenseal | Peppermint Oil |
| Vitamin E | Goldenseal | Spearmint Oil |
| Vitamin E | Fenugreek | Mullein |
| Vitamin E | Fenugreek | Phenol |
| Vitamin E | Fenugreek | Camphor |
| Vitamin E | Fenugreek | Pectin |
| Vitamin E | Fenugreek | Eucalyptus Oil |
| Vitamin E | Fenugreek | Peppermint Oil |
| Vitamin E | Fenugreek | Spearmint Oil |
| Vitamin E | Mullein | Phenol |
| Vitamin E | Mullein | Camphor |
| Vitamin E | Mullein | Pectin |
| Vitamin E | Mullein | Eucalyptus Oil |
| Vitamin E | Mullein | Peppermint Oil |
| Vitamin E | Mullein | Spearmint Oil |
| Vitamin E | Phenol | Camphor |
| Vitamin E | Phenol | Pectin |
| Vitamin E | Phenol | Eucalyptus Oil |
| Vitamin E | Phenol | Peppermint Oil |
| Vitamin E | Phenol | Spearmint Oil |
| Vitamin E | Camphor | Pectin |
| Vitamin E | Camphor | Eucalyptus Oil |
| Vitamin E | Camphor | Peppermint Oil |
| Vitamin E | Camphor | Spearmint Oil |
| Vitamin E | Pectin | Eucalyptus Oil |
| Vitamin E | Pectin | Peppermint Oil |
| Vitamin E | Pectin | Spearmint Oil |
| Vitamin E | Eucalyptus Oil | Peppermint Oil |
| Vitamin E | Eucalyptus Oil | Spearmint Oil |
| Vitamin E | Peppermint Oil | Spearmint Oil |
| Zinc | Magnesium | Selenium |
| Zinc | Magnesium | Echinacea |
| Zinc | Magnesium | Olive leaf |
| Zinc | Magnesium | Wild indigo |
| Zinc | Magnesium | Goldenseal |
| Zinc | Magnesium | Fenugreek |
| Zinc | Magnesium | Mullein |
| Zinc | Magnesium | Phenol |
| Zinc | Magnesium | Camphor |
| Zinc | Magnesium | Pectin |
| Zinc | Magnesium | Eucalyptus Oil |
| Zinc | Magnesium | Peppermint Oil |
| Zinc | Magnesium | Spearmint Oil |
| Zinc | Selenium | Echinacea |
| Zinc | Selenium | Olive leaf |
| Zinc | Selenium | Wild indigo |
| Zinc | Selenium | Goldenseal |
| Zinc | Selenium | Fenugreek |
| Zinc | Selenium | Mullein |
| Zinc | Selenium | Phenol |
| Zinc | Selenium | Camphor |
| Zinc | Selenium | Pectin |

TABLE 3-continued

Three Ingredient Combinations

| First Ingredient | Second Ingredient | Third Ingredient |
|---|---|---|
| Zinc | Selenium | Eucalyptus Oil |
| Zinc | Selenium | Peppermint Oil |
| Zinc | Selenium | Spearmint Oil |
| Zinc | Echinacea | Olive leaf |
| Zinc | Echinacea | Wild indigo |
| Zinc | Echinacea | Goldenseal |
| Zinc | Echinacea | Fenugreek |
| Zinc | Echinacea | Mullein |
| Zinc | Echinacea | Phenol |
| Zinc | Echinacea | Camphor |
| Zinc | Echinacea | Pectin |
| Zinc | Echinacea | Eucalyptus Oil |
| Zinc | Echinacea | Peppermint Oil |
| Zinc | Echinacea | Spearmint Oil |
| Zinc | Olive leaf | Wild indigo |
| Zinc | Olive leaf | Goldenseal |
| Zinc | Olive leaf | Fenugreek |
| Zinc | Olive leaf | Mullein |
| Zinc | Olive leaf | Phenol |
| Zinc | Olive leaf | Camphor |
| Zinc | Olive leaf | Pectin |
| Zinc | Olive leaf | Eucalyptus Oil |
| Zinc | Olive leaf | Peppermint Oil |
| Zinc | Olive leaf | Spearmint Oil |
| Zinc | Wild indigo | Goldenseal |
| Zinc | Wild indigo | Fenugreek |
| Zinc | Wild indigo | Mullein |
| Zinc | Wild indigo | Phenol |
| Zinc | Wild indigo | Camphor |
| Zinc | Wild indigo | Pectin |
| Zinc | Wild indigo | Eucalyptus Oil |
| Zinc | Wild indigo | Peppermint Oil |
| Zinc | Wild indigo | Spearmint Oil |
| Zinc | Goldenseal | Fenugreek |
| Zinc | Goldenseal | Mullein |
| Zinc | Goldenseal | Phenol |
| Zinc | Goldenseal | Camphor |
| Zinc | Goldenseal | Pectin |
| Zinc | Goldenseal | Eucalyptus Oil |
| Zinc | Goldenseal | Peppermint Oil |
| Zinc | Goldenseal | Spearmint Oil |
| Zinc | Fenugreek | Mullein |
| Zinc | Fenugreek | Phenol |
| Zinc | Fenugreek | Camphor |
| Zinc | Fenugreek | Pectin |
| Zinc | Fenugreek | Eucalyptus Oil |
| Zinc | Fenugreek | Peppermint Oil |
| Zinc | Fenugreek | Spearmint Oil |
| Zinc | Mullein | Phenol |
| Zinc | Mullein | Camphor |
| Zinc | Mullein | Pectin |
| Zinc | Mullein | Eucalyptus Oil |
| Zinc | Mullein | Peppermint Oil |
| Zinc | Mullein | Spearmint Oil |
| Zinc | Phenol | Camphor |
| Zinc | Phenol | Pectin |
| Zinc | Phenol | Eucalyptus Oil |
| Zinc | Phenol | Peppermint Oil |
| Zinc | Phenol | Spearmint Oil |
| Zinc | Camphor | Pectin |
| Zinc | Camphor | Eucalyptus Oil |
| Zinc | Camphor | Peppermint Oil |
| Zinc | Camphor | Spearmint Oil |
| Zinc | Pectin | Eucalyptus Oil |
| Zinc | Pectin | Peppermint Oil |
| Zinc | Pectin | Spearmint Oil |
| Zinc | Eucalyptus Oil | Peppermint Oil |
| Zinc | Eucalyptus Oil | Spearmint Oil |
| Zinc | Peppermint Oil | Spearmint Oil |
| Magnesium | Selenium | Echinacea |
| Magnesium | Selenium | Olive leaf |
| Magnesium | Selenium | Wild indigo |
| Magnesium | Selenium | Goldenseal |
| Magnesium | Selenium | Fenugreek |
| Magnesium | Selenium | Mullein |
| Magnesium | Selenium | Phenol |
| Magnesium | Selenium | Camphor |
| Magnesium | Selenium | Pectin |
| Magnesium | Selenium | Eucalyptus Oil |
| Magnesium | Selenium | Peppermint Oil |
| Magnesium | Selenium | Spearmint Oil |
| Magnesium | Echinacea | Olive leaf |
| Magnesium | Echinacea | Wild indigo |
| Magnesium | Echinacea | Goldenseal |
| Magnesium | Echinacea | Fenugreek |
| Magnesium | Echinacea | Mullein |
| Magnesium | Echinacea | Phenol |
| Magnesium | Echinacea | Camphor |
| Magnesium | Echinacea | Pectin |
| Magnesium | Echinacea | Eucalyptus Oil |
| Magnesium | Echinacea | Peppermint Oil |
| Magnesium | Echinacea | Spearmint Oil |
| Magnesium | Olive leaf | Wild indigo |
| Magnesium | Olive leaf | Goldenseal |
| Magnesium | Olive leaf | Fenugreek |
| Magnesium | Olive leaf | Mullein |
| Magnesium | Olive leaf | Phenol |
| Magnesium | Olive leaf | Camphor |
| Magnesium | Olive leaf | Pectin |
| Magnesium | Olive leaf | Eucalyptus Oil |
| Magnesium | Olive leaf | Peppermint Oil |
| Magnesium | Olive leaf | Spearmint Oil |
| Magnesium | Wild indigo | Goldenseal |
| Magnesium | Wild indigo | Fenugreek |
| Magnesium | Wild indigo | Mullein |
| Magnesium | Wild indigo | Phenol |
| Magnesium | Wild indigo | Camphor |
| Magnesium | Wild indigo | Pectin |
| Magnesium | Wild indigo | Eucalyptus Oil |
| Magnesium | Wild indigo | Peppermint Oil |
| Magnesium | Wild indigo | Spearmint Oil |
| Magnesium | Goldenseal | Fenugreek |
| Magnesium | Goldenseal | Mullein |
| Magnesium | Goldenseal | Phenol |
| Magnesium | Goldenseal | Camphor |
| Magnesium | Goldenseal | Pectin |
| Magnesium | Goldenseal | Eucalyptus Oil |
| Magnesium | Goldenseal | Peppermint Oil |
| Magnesium | Goldenseal | Spearmint Oil |
| Magnesium | Fenugreek | Mullein |
| Magnesium | Fenugreek | Phenol |
| Magnesium | Fenugreek | Camphor |
| Magnesium | Fenugreek | Pectin |
| Magnesium | Fenugreek | Eucalyptus Oil |
| Magnesium | Fenugreek | Peppermint Oil |
| Magnesium | Fenugreek | Spearmint Oil |
| Magnesium | Mullein | Phenol |
| Magnesium | Mullein | Camphor |
| Magnesium | Mullein | Pectin |
| Magnesium | Mullein | Eucalyptus Oil |
| Magnesium | Mullein | Peppermint Oil |
| Magnesium | Mullein | Spearmint Oil |
| Magnesium | Phenol | Camphor |
| Magnesium | Phenol | Pectin |
| Magnesium | Phenol | Eucalyptus Oil |
| Magnesium | Phenol | Peppermint Oil |
| Magnesium | Phenol | Spearmint Oil |
| Magnesium | Camphor | Pectin |
| Magnesium | Camphor | Eucalyptus Oil |
| Magnesium | Camphor | Peppermint Oil |
| Magnesium | Camphor | Spearmint Oil |
| Magnesium | Pectin | Eucalyptus Oil |
| Magnesium | Pectin | Peppermint Oil |
| Magnesium | Pectin | Spearmint Oil |
| Magnesium | Eucalyptus Oil | Peppermint Oil |
| Magnesium | Eucalyptus Oil | Spearmint Oil |
| Magnesium | Peppermint Oil | Spearmint Oil |
| Selenium | Echinacea | Olive leaf |
| Selenium | Echinacea | Wild indigo |
| Selenium | Echinacea | Goldenseal |
| Selenium | Echinacea | Fenugreek |
| Selenium | Echinacea | Mullein |

TABLE 3-continued

Three Ingredient Combinations

| First Ingredient | Second Ingredient | Third Ingredient |
|---|---|---|
| Selenium | Echinacea | Phenol |
| Selenium | Echinacea | Camphor |
| Selenium | Echinacea | Pectin |
| Selenium | Echinacea | Eucalyptus Oil |
| Selenium | Echinacea | Peppermint Oil |
| Selenium | Echinacea | Spearmint Oil |
| Selenium | Olive leaf | Wild indigo |
| Selenium | Olive leaf | Goldenseal |
| Selenium | Olive leaf | Fenugreek |
| Selenium | Olive leaf | Mullein |
| Selenium | Olive leaf | Phenol |
| Selenium | Olive leaf | Camphor |
| Selenium | Olive leaf | Pectin |
| Selenium | Olive leaf | Eucalyptus Oil |
| Selenium | Olive leaf | Peppermint Oil |
| Selenium | Olive leaf | Spearmint Oil |
| Selenium | Wild indigo | Goldenseal |
| Selenium | Wild indigo | Fenugreek |
| Selenium | Wild indigo | Mullein |
| Selenium | Wild indigo | Phenol |
| Selenium | Wild indigo | Camphor |
| Selenium | Wild indigo | Pectin |
| Selenium | Wild indigo | Eucalyptus Oil |
| Selenium | Wild indigo | Peppermint Oil |
| Selenium | Wild indigo | Spearmint Oil |
| Selenium | Goldenseal | Fenugreek |
| Selenium | Goldenseal | Mullein |
| Selenium | Goldenseal | Phenol |
| Selenium | Goldenseal | Camphor |
| Selenium | Goldenseal | Pectin |
| Selenium | Goldenseal | Eucalyptus Oil |
| Selenium | Goldenseal | Peppermint Oil |
| Selenium | Goldenseal | Spearmint Oil |
| Selenium | Fenugreek | Mullein |
| Selenium | Fenugreek | Phenol |
| Selenium | Fenugreek | Camphor |
| Selenium | Fenugreek | Pectin |
| Selenium | Fenugreek | Eucalyptus Oil |
| Selenium | Fenugreek | Peppermint Oil |
| Selenium | Fenugreek | Spearmint Oil |
| Selenium | Mullein | Phenol |
| Selenium | Mullein | Camphor |
| Selenium | Mullein | Pectin |
| Selenium | Mullein | Eucalyptus Oil |
| Selenium | Mullein | Peppermint Oil |
| Selenium | Mullein | Spearmint Oil |
| Selenium | Phenol | Camphor |
| Selenium | Phenol | Pectin |
| Selenium | Phenol | Eucalyptus Oil |
| Selenium | Phenol | Peppermint Oil |
| Selenium | Phenol | Spearmint Oil |
| Selenium | Camphor | Pectin |
| Selenium | Camphor | Eucalyptus Oil |
| Selenium | Camphor | Peppermint Oil |
| Selenium | Camphor | Spearmint Oil |
| Selenium | Pectin | Eucalyptus Oil |
| Selenium | Pectin | Peppermint Oil |
| Selenium | Pectin | Spearmint Oil |
| Selenium | Eucalyptus Oil | Peppermint Oil |
| Selenium | Eucalyptus Oil | Spearmint Oil |
| Selenium | Peppermint Oil | Spearmint Oil |
| Echinacea | Olive leaf | Wild indigo |
| Echinacea | Olive leaf | Goldenseal |
| Echinacea | Olive leaf | Fenugreek |
| Echinacea | Olive leaf | Mullein |
| Echinacea | Olive leaf | Phenol |
| Echinacea | Olive leaf | Camphor |
| Echinacea | Olive leaf | Pectin |
| Echinacea | Olive leaf | Eucalyptus Oil |
| Echinacea | Olive leaf | Peppermint Oil |
| Echinacea | Olive leaf | Spearmint Oil |
| Echinacea | Wild indigo | Goldenseal |
| Echinacea | Wild indigo | Fenugreek |
| Echinacea | Wild indigo | Mullein |
| Echinacea | Wild indigo | Phenol |
| Echinacea | Wild indigo | Camphor |
| Echinacea | Wild indigo | Pectin |
| Echinacea | Wild indigo | Eucalyptus Oil |
| Echinacea | Wild indigo | Peppermint Oil |
| Echinacea | Wild indigo | Spearmint Oil |
| Echinacea | Goldenseal | Fenugreek |
| Echinacea | Goldenseal | Mullein |
| Echinacea | Goldenseal | Phenol |
| Echinacea | Goldenseal | Camphor |
| Echinacea | Goldenseal | Pectin |
| Echinacea | Goldenseal | Eucalyptus Oil |
| Echinacea | Goldenseal | Peppermint Oil |
| Echinacea | Goldenseal | Spearmint Oil |
| Echinacea | Fenugreek | Mullein |
| Echinacea | Fenugreek | Phenol |
| Echinacea | Fenugreek | Camphor |
| Echinacea | Fenugreek | Pectin |
| Echinacea | Fenugreek | Eucalyptus Oil |
| Echinacea | Fenugreek | Peppermint Oil |
| Echinacea | Fenugreek | Spearmint Oil |
| Echinacea | Mullein | Phenol |
| Echinacea | Mullein | Camphor |
| Echinacea | Mullein | Pectin |
| Echinacea | Mullein | Eucalyptus Oil |
| Echinacea | Mullein | Peppermint Oil |
| Echinacea | Mullein | Spearmint Oil |
| Echinacea | Phenol | Camphor |
| Echinacea | Phenol | Pectin |
| Echinacea | Phenol | Eucalyptus Oil |
| Echinacea | Phenol | Peppermint Oil |
| Echinacea | Phenol | Spearmint Oil |
| Echinacea | Camphor | Pectin |
| Echinacea | Camphor | Eucalyptus Oil |
| Echinacea | Camphor | Peppermint Oil |
| Echinacea | Camphor | Spearmint Oil |
| Echinacea | Pectin | Eucalyptus Oil |
| Echinacea | Pectin | Peppermint Oil |
| Echinacea | Pectin | Spearmint Oil |
| Echinacea | Eucalyptus Oil | Peppermint Oil |
| Echinacea | Eucalyptus Oil | Spearmint Oil |
| Echinacea | Peppermint Oil | Spearmint Oil |
| Olive leaf | Wild indigo | Goldenseal |
| Olive leaf | Wild indigo | Fenugreek |
| Olive leaf | Wild indigo | Mullein |
| Olive leaf | Wild indigo | Phenol |
| Olive leaf | Wild indigo | Camphor |
| Olive leaf | Wild indigo | Pectin |
| Olive leaf | Wild indigo | Eucalyptus Oil |
| Olive leaf | Wild indigo | Peppermint Oil |
| Olive leaf | Wild indigo | Spearmint Oil |
| Olive leaf | Goldenseal | Fenugreek |
| Olive leaf | Goldenseal | Mullein |
| Olive leaf | Goldenseal | Phenol |
| Olive leaf | Goldenseal | Camphor |
| Olive leaf | Goldenseal | Pectin |
| Olive leaf | Goldenseal | Eucalyptus Oil |
| Olive leaf | Goldenseal | Peppermint Oil |
| Olive leaf | Goldenseal | Spearmint Oil |
| Olive leaf | Fenugreek | Mullein |
| Olive leaf | Fenugreek | Phenol |
| Olive leaf | Fenugreek | Camphor |
| Olive leaf | Fenugreek | Pectin |
| Olive leaf | Fenugreek | Eucalyptus Oil |
| Olive leaf | Fenugreek | Peppermint Oil |
| Olive leaf | Fenugreek | Spearmint Oil |
| Olive leaf | Mullein | Phenol |
| Olive leaf | Mullein | Camphor |
| Olive leaf | Mullein | Pectin |
| Olive leaf | Mullein | Eucalyptus Oil |
| Olive leaf | Mullein | Peppermint Oil |
| Olive leaf | Mullein | Spearmint Oil |
| Olive leaf | Phenol | Camphor |
| Olive leaf | Phenol | Pectin |
| Olive leaf | Phenol | Eucalyptus Oil |
| Olive leaf | Phenol | Peppermint Oil |
| Olive leaf | Phenol | Spearmint Oil |
| Olive leaf | Camphor | Pectin |

TABLE 3-continued

Three Ingredient Combinations

| First Ingredient | Second Ingredient | Third Ingredient |
|---|---|---|
| Olive leaf | Camphor | Eucalyptus Oil |
| Olive leaf | Camphor | Peppermint Oil |
| Olive leaf | Camphor | Spearmint Oil |
| Olive leaf | Pectin | Eucalyptus Oil |
| Olive leaf | Pectin | Peppermint Oil |
| Olive leaf | Pectin | Spearmint Oil |
| Olive leaf | Eucalyptus Oil | Peppermint Oil |
| Olive leaf | Eucalyptus Oil | Spearmint Oil |
| Olive leaf | Peppermint Oil | Spearmint Oil |
| Wild indigo | Goldenseal | Fenugreek |
| Wild indigo | Goldenseal | Mullein |
| Wild indigo | Goldenseal | Phenol |
| Wild indigo | Goldenseal | Camphor |
| Wild indigo | Goldenseal | Pectin |
| Wild indigo | Goldenseal | Eucalyptus Oil |
| Wild indigo | Goldenseal | Peppermint Oil |
| Wild indigo | Goldenseal | Spearmint Oil |
| Wild indigo | Fenugreek | Mullein |
| Wild indigo | Fenugreek | Phenol |
| Wild indigo | Fenugreek | Camphor |
| Wild indigo | Fenugreek | Pectin |
| Wild indigo | Fenugreek | Eucalyptus Oil |
| Wild indigo | Fenugreek | Peppermint Oil |
| Wild indigo | Fenugreek | Spearmint Oil |
| Wild indigo | Mullein | Phenol |
| Wild indigo | Mullein | Camphor |
| Wild indigo | Mullein | Pectin |
| Wild indigo | Mullein | Eucalyptus Oil |
| Wild indigo | Mullein | Peppermint Oil |
| Wild indigo | Mullein | Spearmint Oil |
| Wild indigo | Phenol | Camphor |
| Wild indigo | Phenol | Pectin |
| Wild indigo | Phenol | Eucalyptus Oil |
| Wild indigo | Phenol | Peppermint Oil |
| Wild indigo | Phenol | Spearmint Oil |
| Wild indigo | Camphor | Pectin |
| Wild indigo | Camphor | Eucalyptus Oil |
| Wild indigo | Camphor | Peppermint Oil |
| Wild indigo | Camphor | Spearmint Oil |
| Wild indigo | Pectin | Eucalyptus Oil |
| Wild indigo | Pectin | Peppermint Oil |
| Wild indigo | Pectin | Spearmint Oil |
| Wild indigo | Eucalyptus Oil | Peppermint Oil |
| Wild indigo | Eucalyptus Oil | Spearmint Oil |
| Wild indigo | Peppermint Oil | Spearmint Oil |
| Goldenseal | Fenugreek | Mullein |
| Goldenseal | Fenugreek | Phenol |
| Goldenseal | Fenugreek | Camphor |
| Goldenseal | Fenugreek | Pectin |
| Goldenseal | Fenugreek | Eucalyptus Oil |
| Goldenseal | Fenugreek | Peppermint Oil |
| Goldenseal | Fenugreek | Spearmint Oil |
| Goldenseal | Mullein | Phenol |
| Goldenseal | Mullein | Camphor |
| Goldenseal | Mullein | Pectin |
| Goldenseal | Mullein | Eucalyptus Oil |
| Goldenseal | Mullein | Peppermint Oil |
| Goldenseal | Mullein | Spearmint Oil |
| Goldenseal | Phenol | Camphor |
| Goldenseal | Phenol | Pectin |
| Goldenseal | Phenol | Eucalyptus Oil |
| Goldenseal | Phenol | Peppermint Oil |
| Goldenseal | Phenol | Spearmint Oil |
| Goldenseal | Camphor | Pectin |
| Goldenseal | Camphor | Eucalyptus Oil |
| Goldenseal | Camphor | Peppermint Oil |
| Goldenseal | Camphor | Spearmint Oil |
| Goldenseal | Pectin | Eucalyptus Oil |
| Goldenseal | Pectin | Peppermint Oil |
| Goldenseal | Pectin | Spearmint Oil |
| Goldenseal | Eucalyptus Oil | Peppermint Oil |
| Goldenseal | Eucalyptus Oil | Spearmint Oil |
| Goldenseal | Peppermint Oil | Spearmint Oil |
| Fenugreek | Mullein | Phenol |
| Fenugreek | Mullein | Camphor |
| Fenugreek | Mullein | Pectin |
| Fenugreek | Mullein | Eucalyptus Oil |
| Fenugreek | Mullein | Peppermint Oil |
| Fenugreek | Mullein | Spearmint Oil |
| Fenugreek | Phenol | Camphor |
| Fenugreek | Phenol | Pectin |
| Fenugreek | Phenol | Eucalyptus Oil |
| Fenugreek | Phenol | Peppermint Oil |
| Fenugreek | Phenol | Spearmint Oil |
| Fenugreek | Camphor | Pectin |
| Fenugreek | Camphor | Eucalyptus Oil |
| Fenugreek | Camphor | Peppermint Oil |
| Fenugreek | Camphor | Spearmint Oil |
| Fenugreek | Pectin | Eucalyptus Oil |
| Fenugreek | Pectin | Peppermint Oil |
| Fenugreek | Pectin | Spearmint Oil |
| Fenugreek | Eucalyptus Oil | Peppermint Oil |
| Fenugreek | Eucalyptus Oil | Spearmint Oil |
| Fenugreek | Peppermint Oil | Spearmint Oil |
| Mullein | Phenol | Camphor |
| Mullein | Phenol | Pectin |
| Mullein | Phenol | Eucalyptus Oil |
| Mullein | Phenol | Peppermint Oil |
| Mullein | Phenol | Spearmint Oil |
| Mullein | Camphor | Pectin |
| Mullein | Camphor | Eucalyptus Oil |
| Mullein | Camphor | Peppermint Oil |
| Mullein | Camphor | Spearmint Oil |
| Mullein | Pectin | Eucalyptus Oil |
| Mullein | Pectin | Peppermint Oil |
| Mullein | Pectin | Spearmint Oil |
| Mullein | Eucalyptus Oil | Peppermint Oil |
| Mullein | Eucalyptus Oil | Spearmint Oil |
| Mullein | Peppermint Oil | Spearmint Oil |
| Phenol | Camphor | Pectin |
| Phenol | Camphor | Eucalyptus Oil |
| Phenol | Camphor | Peppermint Oil |
| Phenol | Camphor | Spearmint Oil |
| Phenol | Pectin | Eucalyptus Oil |
| Phenol | Pectin | Peppermint Oil |
| Phenol | Pectin | Spearmint Oil |
| Phenol | Eucalyptus Oil | Peppermint Oil |
| Phenol | Eucalyptus Oil | Spearmint Oil |
| Phenol | Peppermint Oil | Spearmint Oil |
| Camphor | Pectin | Eucalyptus Oil |
| Camphor | Pectin | Peppermint Oil |
| Camphor | Pectin | Spearmint Oil |
| Camphor | Eucalyptus Oil | Peppermint Oil |
| Camphor | Eucalyptus Oil | Spearmint Oil |
| Camphor | Peppermint Oil | Spearmint Oil |
| Pectin | Eucalyptus Oil | Peppermint Oil |
| Pectin | Eucalyptus Oil | Spearmint Oil |
| Pectin | Peppermint Oil | Spearmint Oil |
| Eucalyptus Oil | Peppermint Oil | Spearmint Oil |

Kits

The invention also provides kits comprising one or more compositions, as described herein. For example, the kit can comprise one or more solid confections or lollipops in the shape of a human oral cavity, a pacifier, an octahedron or octagon. In various embodiments, the number of solid confections or lollipops in the kit is sufficient for administration to or consumption by the subject until the ear infection or blocked inner ear canal is cleared.

The kit may also contain instructions for effective administration of the composition in order to drain fluid and relieve pain of the inner ear. For example, the instructions may advise or illustrate a body posture or position for the subject to assume with the affected ear facing upward to allow the combined actions of gravity and sucking to produce negative pressure within the oral cavity to release excess fluid from the inner ear canal.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating an ear infection comprising:
   administering an effective amount of an antibiotic-free salivary-producing hard candy composition to an individual suffering from an ear infection,
   wherein said composition comprises:
   a sweetening agent;
   a natural flavoring agent;
   an extract; and
   citric acid; and
   wherein said hard candy composition is shaped to include a first surface that is convex and a second surface that is flat,
   wherein said first surface is configured to fit within an oral cavity of the individual and to contact a roof of the individual's oral cavity, and
   wherein the second surface is configured to contact the tongue of the individual, and
   wherein the first surface and the second surface are arranged such that when the individual sucks on the hard candy composition a negative pressure is formed within the individual's oral cavity that promotes drainage of fluid from the individual's Eustachian tube.

2. The method of claim 1, wherein the ear infection is acute otitis media (AOM).

3. The method of claim 1, wherein the sweetening agent comprises isomalt.

4. The method of claim 1, wherein said sweeting agent is xylitol.

5. The method of claim 1, wherein the natural flavoring agent comprises lemons.

6. The method of claim 1, wherein the natural flavoring agent comprises peppermint oil.

7. The method of claim 1, wherein said composition further comprises Mullein.

8. The method of claim 1, wherein said composition further comprises vitamin C.

9. The method of claim 1, wherein the extract comprises lemon oil.

10. The method of claim 1, wherein said composition further comprises a non-essential amino acid.

11. The method of claim 1, wherein said composition further comprises a non-steroidal anti-inflammatory agent.

12. The method of claim 11, wherein the non-steroidal anti-inflammatory agent comprises ibuprofen.

13. A method of treating ear pain, comprising:
    administering to an individual in need thereof an antibiotic-free salivary-producing hard candy composition, wherein said composition comprises:
    a sweetening agent;
    a natural flavoring agent;
    an extract; and
    citric acid,
    wherein the hard candy composition is shaped to include a first surface that is convex and a second surface that is flat; wherein said first surface is configured to fit within an oral cavity of the individual and to contact a roof of the individual's oral cavity; and wherein the second surface contacts the tongue of said individual, and
    wherein the administering causes the individual to suck on the hard candy composition in order to form a negative pressure within the individual's oral cavity that promotes pressure equalization in the middle ear.

14. The method of claim 13, wherein said pain is associated with acute otitis media (AOM).

15. The method of claim 13, wherein said pain is associated with pressure in an ear.

16. The method of claim 13, wherein said sweetening agent comprises isomalt.

17. The method of claim 13, wherein said sweeting agent is xylitol.

18. The method of claim 13, wherein said natural flavoring comprises peppermint oil.

19. The method of claim 13, wherein said composition further comprises Mullein.

20. The method of claim 13, wherein said extract comprises lemon oil.

* * * * *